United States Patent
Podbilewicz et al.

(10) Patent No.: US 9,468,660 B2
(45) Date of Patent: Oct. 18, 2016

(54) ANTINEMATODAL METHODS AND COMPOSITIONS

(75) Inventors: Benjamin Podbilewicz, Haifa (IL); Ori Avinoam, Haifa (IL); Judith M. White, Charlottesville, VA (US)

(73) Assignees: Technion Research and Development Foundation Ltd., Haifa (IL); University of Virginia Patent Foundation, Charlottesville, VA (US)

( * ) Notice: Subject to any disclaimer, the term of this patent is extended or adjusted under 35 U.S.C. 154(b) by 153 days.

(21) Appl. No.: 13/982,996

(22) PCT Filed: Jan. 31, 2012

(86) PCT No.: PCT/IL2012/000054
§ 371 (c)(1),
(2), (4) Date: Sep. 3, 2013

(87) PCT Pub. No.: WO2012/104837
PCT Pub. Date: Aug. 9, 2012

(65) Prior Publication Data
US 2013/0336939 A1 Dec. 19, 2013

Related U.S. Application Data

(60) Provisional application No. 61/438,274, filed on Feb. 1, 2011.

(51) Int. Cl.
| | | |
|---|---|---|
| *A01N 63/00* | (2006.01) | |
| *A61K 36/00* | (2006.01) | |
| *C07K 14/435* | (2006.01) | |
| *A61K 35/12* | (2015.01) | |
| *A61K 35/57* | (2015.01) | |
| *A61K 35/76* | (2015.01) | |

(52) U.S. Cl.
CPC ............... *A61K 36/00* (2013.01); *A01N 63/00* (2013.01); *A61K 35/12* (2013.01); *A61K 35/57* (2013.01); *A61K 35/76* (2013.01); *C07K 14/4354* (2013.01); *C07K 14/43545* (2013.01)

(58) Field of Classification Search
CPC .................................................. C07K 14/4354
USPC ....................................................... 424/93.2
See application file for complete search history.

(56) References Cited

U.S. PATENT DOCUMENTS 7,402,409 B2 7/2008 Yu
8,088,976 B2 1/2012 Boukharov

FOREIGN PATENT DOCUMENTS

| CN | 1668335 | 9/2005 |
| CN | 1741818 | 3/2006 |
| EP | 1000934 | 5/2000 |
| WO | 99/24582 | 5/1999 |
| WO | 00/42855 | 7/2000 |
| WO | 2006/123157 | 11/2006 |

OTHER PUBLICATIONS

Podbilewicz et al., 2006, Developmental Cell, vol. 11, pp. 471-481.*
Shemer et al. (2004, Current Biology, vol. 14, pp. 1587-1591).*
Luukkonen et al., (1973) Lipids of cultured mosquito cells (Aedes albopictus). Comparison with cultured mammalian fibroblasts (BHK 21 cells). Biochim Biophys Acta 326(2): 256-61.
Marheineke et al., (1998) Lipid composition of Spodoptera frugiperda (Sf9) and Trichoplusia ni (Tn) insect cells used for baculovirus infection. FEBS Lett 441(1): 49-52.
Avinoam et al., (2011) Conserved eukaryotic fusogens can fuse viral envelopes to cells. Science 332(6029): 589-592.
Avinoam et al., (2011) Supporting online material for conserved eukaryotic fusogens can fuse viral envelopes to cells. Science pp. 1-24.
Chen et al., (2007) Cell-cell fusion. FEBS Lett 581(11): 2181-2193.
del Campo et al., (2005) Fusogenic activity of EFF-1 is regulated via dynamic localization in fusing somatic cells of C. elegans. Curr Biol 15(5): 413-423.
Gottesman et al., (2010) V-fusion: a convenient, nontoxic method for cell fusion. Biotechniques 49(4): 747-750.
Hu et al., (2003) Fusion of cells by flipped SNAREs. Science 300(5626): 1745-1749.
Hugot et al., (2001) Biodiversity in helminths and nematodes as a field of study: an overview. Nematology 3(3): 199-208.
Kielian and Rey (2006) Virus membrane-fusion proteins: more than one way to make a hairpin. Nat Rev Microbiol 4(1): 67-76.
Köppen et al., (2001) Cooperative regulation of AJM-1 controls junctional integrity in Caenorhabditis elegans epithelia. Nat Cell Biol 3(11): 983-991.
Martens and McMahon (2008) Mechanisms of membrane fusion: disparate players and common principles. Nat Rev Mol Cell Biol 9(7): 543-556.
Mohler et al., (2002) The type I membrane protein EFF-1 is essential for developmental cell fusion. Dev Cell 2(3): 355-362.
Niwa et al., (1991) Efficient selection for high-expression transfectants with a novel eukaryotic vector. Gene 108(2): 193-199.
Oren-Suissa and Podbilewicz (2007) Cell fusion during development. Trends Cell Biol 17(11): 537-546.
Oren-Suissa et al., (2010) The fusogen EFF-1 controls sculpting of mechanosensory dendrites. Science 328(5983): 1285-1288.
Podbilewicz et al., (2006) The C. elegans developmental fusogen EFF-1 mediates homotypic fusion in heterologous cells and in vivo. Dev Cell 11(4): 471-481.
Sapir et al., (2007) AFF-1, a FOS-1-regulated fusogen, mediates fusion of the anchor cell in C. elegans. Dev Cell 12 (5): 683-698.
Sapir et al., (2008) Viral and developmental cell fusion mechanisms: conservation and divergence. Dev Cell 14(1): 11-21.

(Continued)

*Primary Examiner* — Anoop Singh
*Assistant Examiner* — David A Montanari
(74) *Attorney, Agent, or Firm* — Rodney J. Fuller; Booth Udall Fuller, PLC

(57) ABSTRACT

There are provided methods and compositions useful in cell-cell fusion using Fusion Family (FF) proteins of nematode origin. There are further provided antinematodal methods and compositions, utilizing fusogenic proteins of the nematode Fusion Family.

2 Claims, 15 Drawing Sheets

(56) References Cited

OTHER PUBLICATIONS

Schornberg et al., (2006) Role of endosomal cathepsins in entry mediated by the Ebola virus glycoprotein. J Virol 80 (8): 4174-4178.
Shemer et al., (2004) EFF-1 is sufficient to initiate and execute tissue-specific cell fusion in C. elegans. Curr Biol 14 (17): 1587-1591.
Takada et al., (1997) A system for functional analysis of Ebola virus glycoprotein. Proc Natl Acad Sci U S A 94(26): 14764-14769.

White et al., (2008) Structures and mechanisms of viral membrane fusion proteins: multiple variations on a common theme. Crit Rev Biochem Mol Biol 43(3): 189-219.

Wickner and Schekman (2008) Membrane fusion. Nat Struct Mol Biol 15(7): 658-664.

William A. Mohler, "Cell-Cell Fusion: Transient Channels Leading to Plasma Membrane Merger", Cell-Cell Channels, 298-316 (2006).

* cited by examiner

Figs. 2A-C 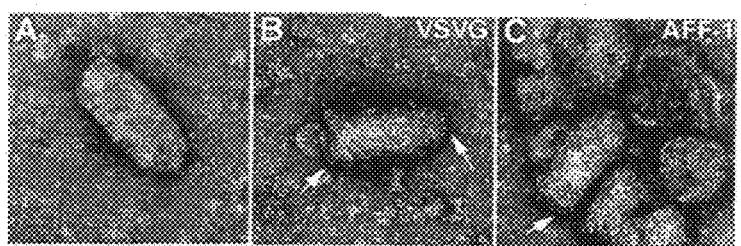
Figs. 2D-E 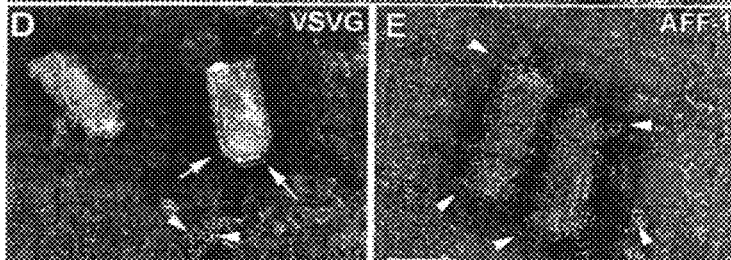
Figs. 2F-H 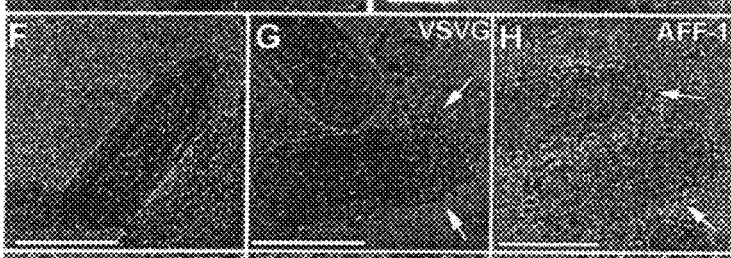
Figs. 2I-K 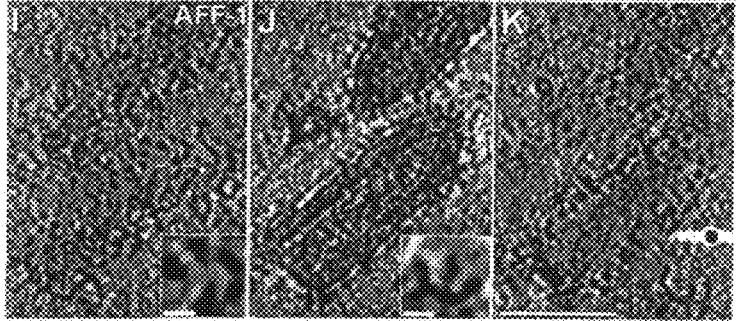
Figs. 2L-M 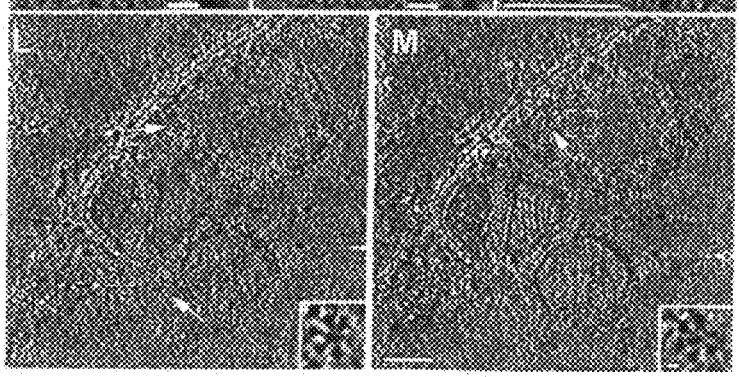

Panel A

Panel B

Panel C

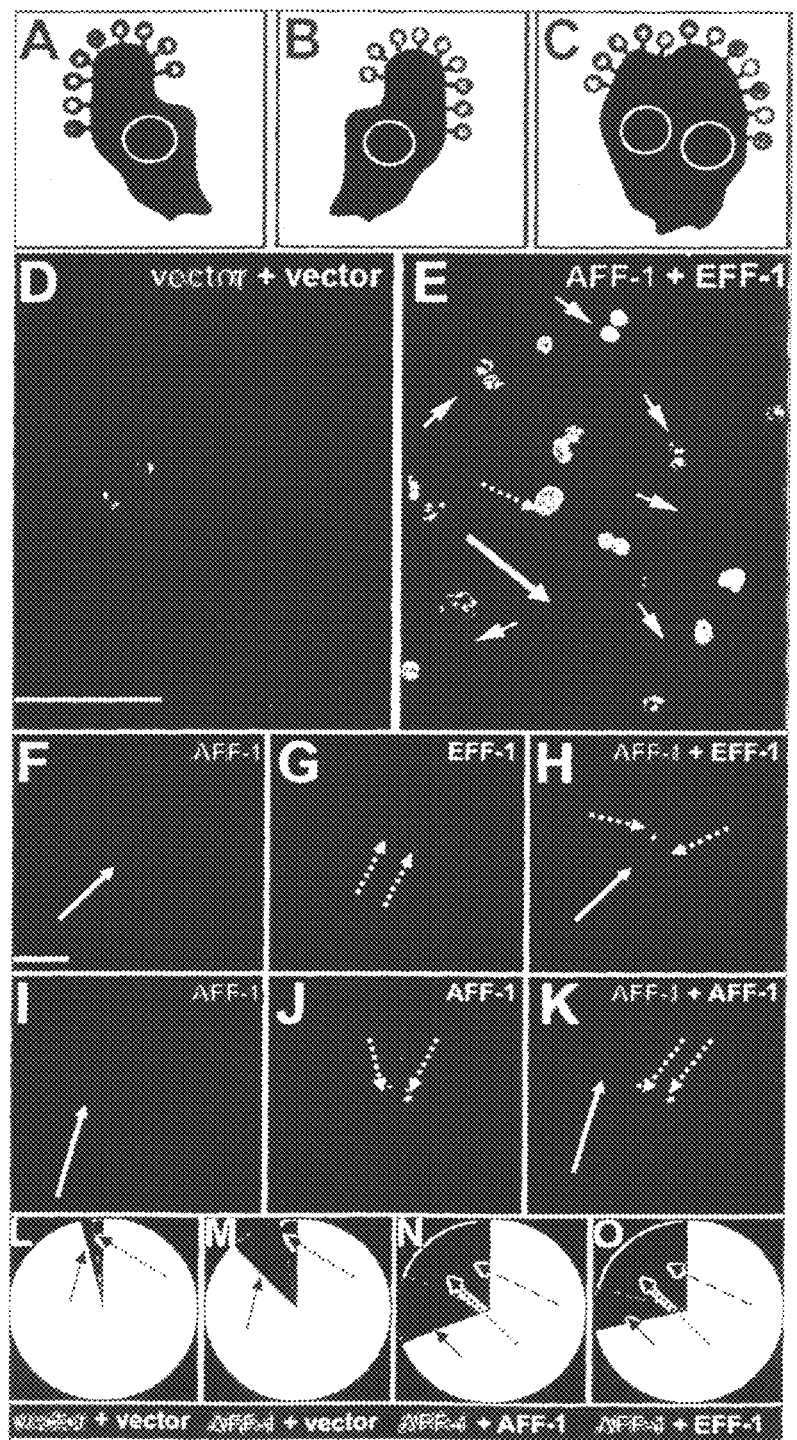
FIG.3A-O

Figs. 4B-E
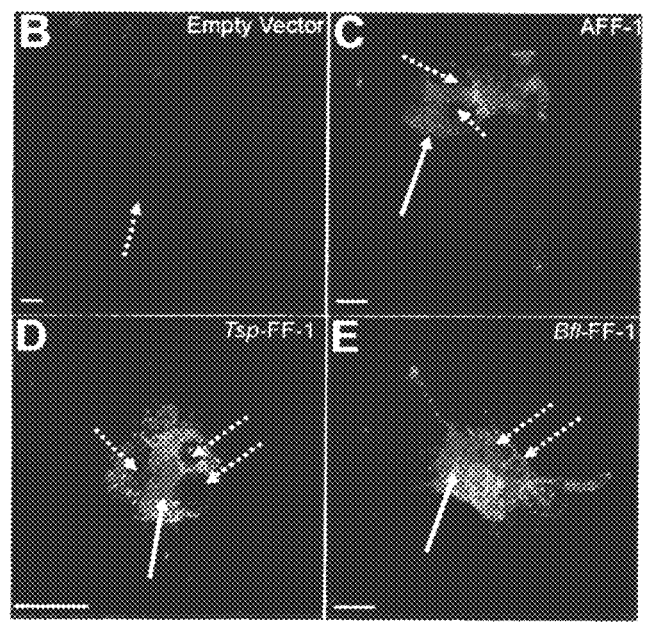
Fig. 4F
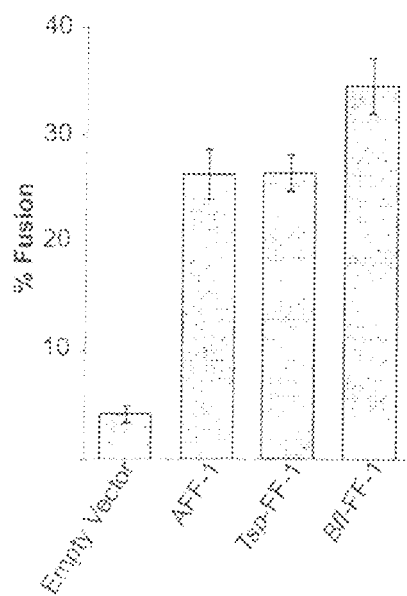

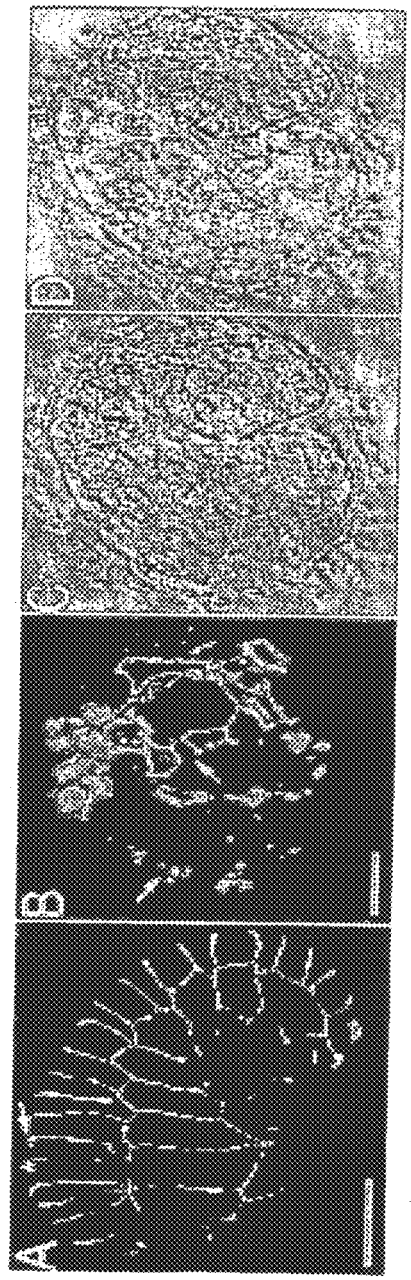
Figs. 7A-D

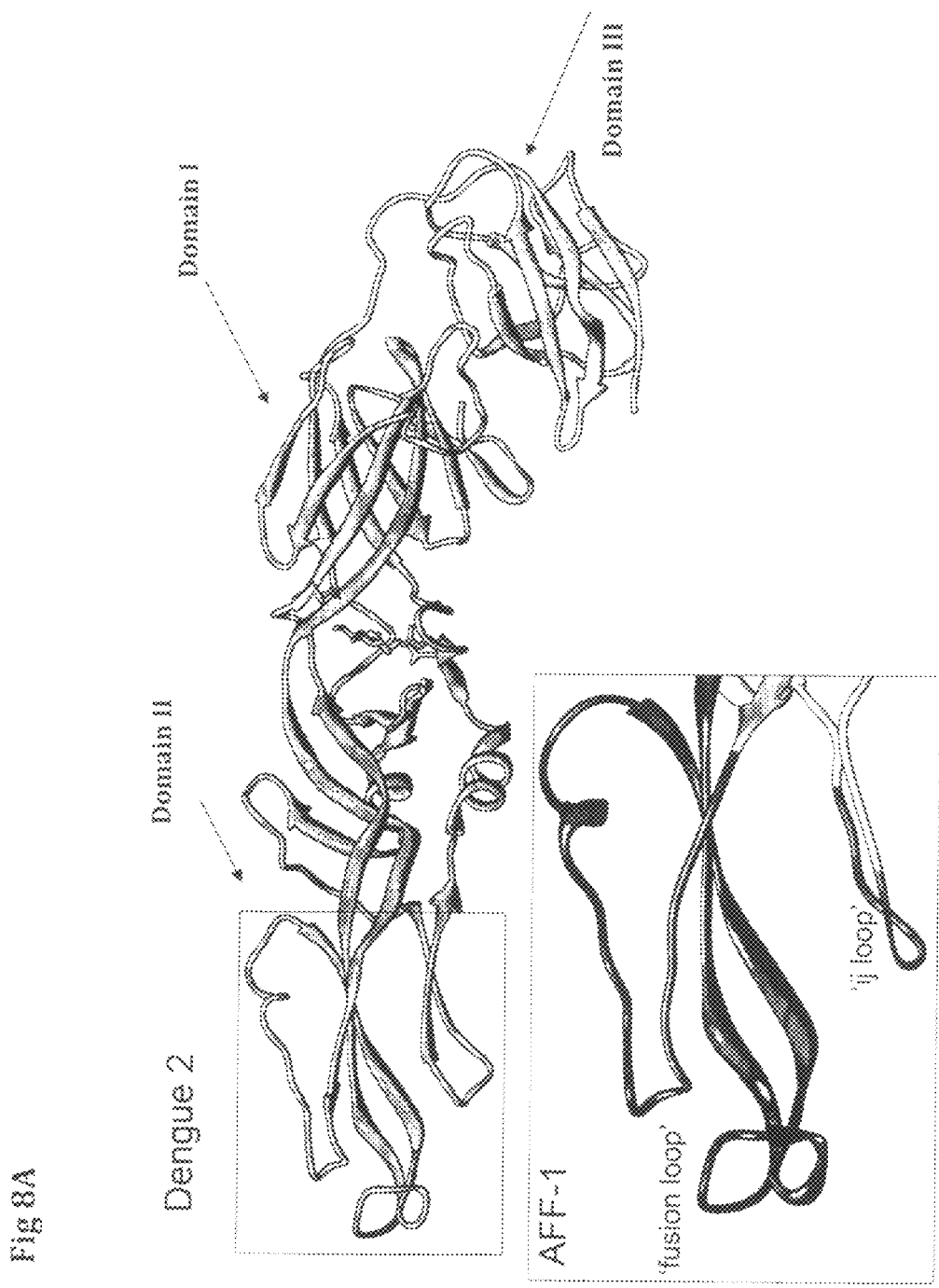

ANTINEMATODAL METHODS AND COMPOSITIONS

RELATED APPLICATION DATA

This application is the U.S. National Stage of International Application No. PCT/IL2012/000054, filed Jan. 31, 2012, which claims the benefit of U.S. Provisional Application No. 61/438,274, filed Feb. 1, 2011, the contents of each of which are herein expressly incorporated by reference for all purposes.

GOVERNMENTAL SUPPORT OF APPLICATION

This invention was made with government support under AI022470 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 54,715 byte ASCII (text) file named "Seq_List" created on Jul. 31, 2013.

FIELD OF THE INVENTION

The present invention relates to methods and compositions useful in cell-cell fusion using Fusion Family proteins of nematodes. There are further provided antinematodal methods and compositions, utilizing fusogenic proteins of the nematode Fusion Family.

BACKGROUND OF THE INVENTION

Virtually all membranes can fuse, ranging from small intracellular vesicles and organelles to entire cells. Consequently, membrane fusion is critical for many biological processes such as fertilization, embryonic and postembryonic development, intracellular trafficking and viral infection (1-6). Exoplasmic cell fusion process involves the merger of plasma membranes. This process can be either transient, as in the case of sperm-egg fusion, resulting in a diploid cell that continues to divide, or permanent, resulting in the formation of syncytia multinuclear cells. Such syncytia serve as essential components of several somatic tissues in metazoans, including the myotubes in muscle formation, osteoclasts in bone formation and syncytial trophoblasts in the formation of the mammalian placenta. Exoplasmic cell fusion also takes place during specific viral infections, as enveloped viruses (such as, for example, influenza, HIV and rabies) fuse their membrane with the host's plasma or endosomal membrane. Similar to exoplasmic cell-cell fusion, viral-cell fusion takes place between the external layers of the fusing membranes and, as such, differs in many aspects from endoplasmic fusion events that occur within a cell (for example, vesicular membrane transport between organelles).

Existing models of the molecular mechanisms of membrane fusion rely on experimental and biophysical analyses performed mainly on viral and intercellular fusion-mediating proteins (known as fusogens). However, how well these models correspond to the mechanisms of action of cell-cell fusogens is unknown (4, 5). For example, U.S. Pat. No. 7,402,409 is directed to cell fusion method. Another cell fusion method is described, for example, by Gottesman et. al. (18).

AFF-1 (Anchor-cell Fusion Failure-1) and EFF-1 (Epithelial Fusion Failure-1) proteins from the nematode *C. elegans* are the first identified and therefore the founding members of a family of fusogens (that is, proteins mediating cell to cell fusion through fusion of the lipid bi-layers of the cells), conserved in nematodes (4). The *C. elegans* FF proteins (CeFF's) were shown to induce fusion in heterologous insect cells (for example, references 7-11). aff-1 and eff-1 mutants are viable, but have severe body deformities and reproductive defects associated with cell fusion failure (9,10). EFF-1's function as a fusogen requires its expression in both fusion partners (8). The Fusion Family (FF) family of proteins is very well conserved among nematodes. FF members were identified in various nematode species, suggesting that the FF family is conserved in the phylum Nematoda (4). Only a few members of the FF family have been identified outside nematodes, none of them in plants or in vertebrates.

Nematodes are the most diverse phylum of pseudocoelomates, and one of the most diverse of all animals. Over 28,000 Nematode species have been described (12) and about 16,000 of the nematodes are parasitic. The nematodes have adapted to nearly every, known ecosystem.

Infection by nematodes in general and parasitic nematodes in particular may affect various hosts, such as, for example, livestock, humans, marine habitats, plants, and the like (13), resulting in health-related and financial consequences. Thus, effective control of infection would contribute significantly to agriculture, farming and medicine with a resultant financial implication. For example, the World Health Organization estimates that at least two billion people are infected by parasitic nematodes, while damage by plant parasitic nematodes is estimated at ~4-10 billion $ per year in losses in the U.S and over $80 billion per year in losses worldwide. Antinematodal agents (also known as antihelminthics, anhelmintics and vermicides), currently in use include mostly chemicals, pharmaceuticals or naturally occurring compounds that are designed to kill the parasite or expel it from its host. Nevertheless, most of these antinematodal agents are extremely toxic and if used in improper dosages are dangerous to humans. Furthermore, the continuous use of chemicals leads to the accumulation of resistant worms and inevitably to treatment failure. In addition, controlling pathogens such as parasitic nematodes can be extremely expensive.

Thus, there is an unmet need for new antihelminthic methods and compositions, that are specific, safe, non toxic, inexpensive and with minimal effect on the environment. The use of nematodal fusogens as exogenously expressed mediators for fusion of virus particles to cells or cell-cell fusion between cells of higher organisms of the plant and animal kingdom is neither taught nor suggested in the art.

SUMMARY OF THE INVENTION

The present invention provides methods and compositions for the fusion of cells including but not limited to mammalian cells, plant cells, avian cells, and the like, as well as fusion of cells with viral particles, using fusogenic proteins comprising at least the extracellular portion of a fusogen of nematode origin. The present invention further discloses antinematodal methods and compositions, methods for their preparation, and uses thereof.

The invention is based in part on the unexpected and surprising finding that conserved eukaryotic fusogens, such as, nematode fusogenic proteins of the Fusion Family proteins, can mediate fusion of viral envelopes to cells, by replacing the endogenous viral fusogenic protein(s). The invention is further based in part on the unexpected finding that the Fusion Family (FF) proteins are a family of membrane fusogens that may be interchangeable between species and even beyond the nematode phylum and hence homologs of the family can be used for fusion of non-insect cells, when expressed on the membranes of those cells. Such findings are surprising and unexpected since induced fusion in heterologous insect cells mediated by C. elegans FF proteins, does not indicate nor suggest that such fusion proteins are capable of replacing an endogenous viral fusogenic protein(s) or that the FF proteins are interchangeable between species and can be used for fusion of cells of higher, non-insect organisms.

According to some embodiments, a method is provided for a specific, protein mediated cell to cell fusion. The protein which mediates the fusion is a fusion protein, for example, of nematode origin, that is expressed on the surface of the cells and thereby allows/induces/mediates fusion of the cells. In some embodiments, the same fusogenic protein is expressed on the surface of both a first and a second cell. In some embodiments, each of the cells expresses a different fusion protein, both fusogenic proteins belong to the same family of fusogenic proteins (homotypic). In some embodiments, the fusogenic proteins are endogenously expressed proteins. In some embodiments, for at least one of the cells to be fused, the fusogenic protein is an exogenous protein. In some embodiments, the cells are of similar origin. For example, both cells may be mammalian cells. In some embodiments, the cells are of different origin. In some exemplary embodiments, the first cell is a pseudotyped enveloped virus and the other (second) cell is of nematode origin. In other exemplary embodiments, the first cell is a pseudotyped enveloped virus and the other (second) cell is of mammalian or plant origin. In some embodiments, at least one of the cells to be fused is not an insect cell. In some embodiments, the cells are of the higher animal or plant kingdom. Each possibility is a separate embodiment.

According to some embodiments, there is provided a method for fusing a first cell and a second cell to produce a fused, hybrid cell, the method comprising mixing/incubating/placing a first cell comprising a first exogenous nematode fusogenic protein with a second cell comprising a second exogenous nematode fusogenic protein; thereby fusing the first and the second cell. In some embodiments, the first cell and the second cell are of the same origin. In some embodiments when the first cell and the second cell are of the same origin, the cells are not insect cells (i.e. non-insect cells). In some embodiments, the first cell and/or the second cell are non-insect cells. In some embodiments, the first cell and the second cell are of the different origin. In some embodiments, the cells are selected from: virus (virus particle), plant cell, avian cell, animal cells or human cell. Each possibility is a separate embodiment. In some embodiments, the cells are non-insect cells. In some embodiments, the first fusogenic protein and the second fusogenic protein are identical. In other embodiments, the first fusogenic protein and the second fusogenic protein are different. In further embodiments, the first fusogenic protein and the second fusogenic protein are selected from AFF-1, EFF-1 or homologs thereof. In some embodiments, the expression of the first exogenous nematode fusogenic protein in the first cell and/or the second cell is transient. In some embodiments, the expression of the first exogenous nematode fusogenic protein in the first cell and/or the second cell is stable. In some embodiments, when the first cell and the second cell are of the same origin, the cells are not of nematode origin.

According to further embodiments, the method for the specific, protein mediated, cell to cell fusion may further be used for immunotherapy methods and vaccine production by fusing antigen-presenting cells to other cells, wherein both cells express a Fusion Family protein of a nematode origin.

According to further embodiments, the method for the specific, protein mediated, cell to cell fusion may further be used for the production of monoclonal antibodies by fusing cells to generate hybridomas using a physiological and less toxic alternative than currently used methods.

According to further embodiments, the method for the specific, protein mediated, cell to cell fusion may further be used for the study of the mechanism of cell-cell fusion in the field of cancer and stem cell research and therapy.

According to some embodiments, there is provided a composition comprising a non-insect cell or viral particle expressing an exogenous nematode fusogenic protein. In some embodiments, the non-insect cell is selected from mammalian, avian, and plant cells. In further embodiments, the fusogenic protein is capable of mediating fusion of the cell or viral particle to a second cell expressing a second nematode fusogenic protein. In other embodiments, the second cell is selected from a mammalian, an avian, and a plant cell exogenously expressing a second nematode fusogenic protein, or a nematode cell endogenously expressing a nematode fusogenic protein. According to yet further embodiments, the second nematode fusogenic protein is the same or different from the fusogen of the non-insect cell. Each possibility is a separate embodiment.

According to some embodiments, there is provided a method for fusing a first cell and a second cell, the method comprising: incubating a first cell comprising a first exogenous nematode fusogenic protein with a second cell comprising a second exogenous nematode fusogenic protein; thereby fusing the first cell and the second cell to form a fused cell, wherein at least one of the cells is not of insect origin. In some embodiments, the first cell and the second cell are of the same origin. In other embodiments, the first cell and the second cell are of different origin. In some embodiments, the cells are selected from, plant, avian, animal, human, and viral particle. In additional embodiments, the first fusogenic protein and the second fusogenic protein are identical. In other embodiments, the first fusogenic protein and the second fusogenic protein are different. In some embodiments, the first fusogenic protein and the second fusogenic protein are selected from AFF-1, EFF-1 or homologs thereof. In other embodiments, the expression of the first exogenous nematode fusogenic protein in the first cell and/or the second cell is transient. In some embodiments, the expression of the exogenous nematode fusogenic protein in the first cell and/or the second cell is stable.

According to additional embodiments, the method for the specific, protein mediated cell to cell fusion, may be used to specifically target nematodes. The method includes fusing a nematode cell with a viral particle expressing a nematode fusogenic protein. The specific fusion of the viral particle and the nematode cell may lead to a desired effect on the nematode cell, wherein the effect may be achieved without the use of an additional antinematodal agent. A desired effect on the nematode cell, may include, for example, killing the cell, inhibiting growth of the cell, stunning the cell, and the like. In some embodiments, the mere fusion of cells may lead to the death of the cells. Each possibility is a separate embodiment.

According to further embodiments, the method for the specific, protein mediated, cell to cell fusion, may be used to specifically target antinematodal agents to nematodes. In such embodiments, fusion of the cells is dependant on the expression of a fusogenic protein of nematode origin in the membranes of both fusing cells, wherein the fusogenic proteins may be identical or different. In some exemplary embodiments, one (first) cell is of nematode origin (endogenously expressing the fusion protein) and the other (second) cell is of different origin (such as, of plant origin, mammalian origin, avian origin, insect, enveloped pseudovirus, or the like), wherein the other (second) cell exogenously expresses a fusogenic protein of nematode origin. The other (second) cell may comprise one or more antinematodal agents, such as, for example: a chemical compound (such as, for example, but not limited to: organophospates, carbamates, imidazole derivatives, such as, for example, benzimidazole, Levamisole, Fumigant nematicides, macrolides, avermectin, milbemycin, tetanus toxin, and the like); a nucleic acid (such as, for example, antisense DNA molecules directed against nematode genes; siRNA or other dsRNA molecules directed against nematode genes, and the like); proteins (such as, for example, limited to: an enzyme capable of cleaving a nematode protein, an antibody directed against a nematode protein, a toxin, and the like), or combinations thereof. Upon the specific fusion of the cells, the antinematodal agent may exert an effect on the nematode. The effect may be, for example, kill, stun, and/or inhibit growth of the nematode.

According to further embodiments, the method for the specific, protein mediated, cell to cell fusion may thus be used for the treatment of parasitic nematode infections of plants, animals and humans.

According to some embodiments, there is provided a composition comprising a cell expressing an exogenous nematode fusogenic protein capable of mediating specific fusion of the cell to the nematode cell; wherein the cell comprises an antinematodal agent. The compositions may be used for killing a nematode cell. In some embodiments, the cell may be selected from a mammalian cell, (including any stem cell), avian cell, virus, and plant cell. The exogenous nematode fusogenic protein may be selected from AFF-1, EFF-1 and homologs thereof.

In some embodiments, the antinematodal agent may be selected from a chemical substance, a protein, a nucleic acid, a toxin and combinations thereof. In further embodiments, the antinematodal agent may expressed by the cell.

According to additional embodiments, the exogenous nematode fusogenic protein in the cell may be transient. In some embodiments, the expression of the exogenous nematode fusogenic protein in the cell may stable.

According to yet further embodiments, the nematode may be selected from, but not limited to: *Caenorhabditis elegans, Caenorhabditis briggsae, Caenorhabditis japonica, Caenorhabditis ramanei, Caenorhabditis brenneri, Caenorhabditis* sp5,7,9,11, *Trichinella spiralis, Trichinella pseudospiralis, Trichinella papuae, Pristionchus entomophagus, Pristionchus maupasi, Pristionchus pacificus, Meloidogyne incognita, Meloidogyne arenaria, Meloidogyne hapla, Globodera pallida, Ancylostoma caninum, Brugia Malayi, Haemonchus contortus, Ascaris suum, Oscheius tipulae, Dirofilaria immitis, Howardula aoronymphium, Litomosoides sigmodontis, Heterodera glycines, Romanomermis culicivorax, Trichuris muris, Strongyloids ratti, Onchocerca volvulus, Teladorsagia circumcincta, Wuchereria bancrofti*, and *Loa loa.*

According to some embodiments, there is provided a composition comprising a virus comprising/expressing a nematode fusion protein, wherein said fusogenic protein is capable of mediating fusion of the virus to a cell of the nematode; wherein said fusion induces killing of the nematode. In some embodiments, the nematode fusogenic protein is selected from AFF-1, EFF-1 and homologs thereof. The nematode may be selected from, but not limited to: *Caenorhabditis elegans, Caenorhabditis briggsae, Caenorhabditis japonica, Caenorhabditis ramanei, Caenorhabditis brenneri, Caenorhabditis* sp5,7,9,11, *Trichinella spiralis, Trichinella pseudospiralis, Trichinella papuae, Pristionchus entomophagus, Pristionchus maupasi, Pristionchus pacificus, Meloidogyne incognita, Meloidogyne arenaria, Meloidogyne hapla, Globodera pallida, Ancylostoma caninum, Brugia Malayi, Haemonchus contortus, Ascaris suum, Oscheius tipulae, Dirofilaria immitis, Howardula aoronymphium, Litomosoides sigmodontis, Heterodera glycines, Romanomermis culicivorax, Trichuris muris, Strongyloids ratti, Onchocerca volvulus, Teladorsagia circumcincta, Wuchereria bancrofti*, and *Loa loa*. Each possibility is a separate embodiment.

In some embodiments, the virus may be selected from Retrovirus, Hepadnavirus, Poxyvirus, Rhabdoviridae viruses, Paramyxoviruses, Herpes viruses and Coronavirus. Each possibility is a separate embodiment.

According to further embodiments, there is provide a method for the targeted killing of a nematode, the method comprising contacting the nematode with a cell comprising an antinematodal agent, wherein the cell further comprises an exogenous fusogenic protein capable of mediating fusion of the cell and a cell of the nematode; and wherein the fusion induces killing of the nematode. The cell may be selected from mammalian cell, stem cell, avian cell, virus, and plant cell. In some embodiments, the exogenous fusogenic protein is a nematode protein selected from AFF-1, EFF-1 and homologs thereof.

According to additional embodiments, the antinematodal agent may be selected from a chemical substance, a protein, a nucleic acid, a toxin and combinations thereof. The antinematodal agent may be expressed by the cell. Each possibility is a separate embodiment.

According to some embodiments, there is provided a method for the targeted killing of a nematode, the method comprising contacting the nematode with a virus comprising an exogenous nematode fusion protein, capable of mediating fusion of the virus to a cell of the nematode; wherein the fusion induces killing of the nematode. In some embodiments, the exogenous fusogenic protein is a nematode fusogenic protein selected from AFF-1, EFF-1 and homologs thereof. In some embodiments, the nematode may be selected from, but not limited to: *Caenorhabditis elegans, Caenorhabditis briggsae, Caenorhabditis japonica, Caenorhabditis ramanei, Caenorhabditis brenneri, Caenorhabditis* sp5,7,9,11, *Trichinella spiralis, Trichinella pseudospiralis, Trichinella papuae, Pristionchus entomophagus, Pristionchus maupasi, Pristionchus pacificus, Meloidogyne incognita, Meloidogyne arenaria, Meloidogyne hapla, Globodera pallida, Ancylostoma caninum, Brugia Haemonchus contortus, Ascaris suum, Oscheius tipulae, Dirofilaria immitis, Howardula aoronymphium, Litomosoides sigmodontis, Heterodera glycines, Romanomermis culicivorax, Trichuris muris, Strongyloids rata, Onchocerca volvulus, Teladorsagia circumcincta, Wuchereria bancrofti*, and *Loa loa*. The virus may be selected from retrovirus, Hepadnavirus, Poxyvirus, Rhabdoviridae viruses, Paramyxoviruses Herpes viruses and Coronavirus.

According to yet further embodiments, there is provided a method for the treatment of a nematode infection in a subject, the method comprising administering to the subject a composition comprising a cell expressing an exogenous nematode fusion protein, wherein fusion of said cell and a nematode cell infecting the subject induces death or inhibition of growth of the nematode. In some embodiments, the subject is human. In some embodiments, the subject is an animal. In some embodiments, the administering is selected from oral administration, injection, suppository and topical application. In further embodiments, the cell may further include an antinematodal agent, selected from a chemical substance, a protein, a nucleic acid, a toxin and combinations thereof. In additional embodiments, the cell may be selected from a mammalian cell, stem cell, avian cell, virus, and plant cell.

According to some embodiments, there is provided a transgenic plant stably expressing a fusogenic protein of the nematode family.

According to yet further embodiments, there is provided a viral vector for the expression of a nematode fusogenic protein on the surface of a virus.

According to additional embodiments, there is provided a recombinant cell expressing a polynucleotide encoding a polypeptide comprising an amino acid sequence at least 15% identical to the amino acid sequence of a nematode fusogenic protein. In some embodiments, the cell may be selected from mammalian cell, stem cell, avian cell, virus, and plant cell. In some exemplary embodiments, the nematode fusogenic protein is selected from Ce-AFF-1 (SEQ ID NO: 23), Ce-EFF-1 (SEQ IS NO:24), tsp-FF-1 (SEQ. ID. No. 25) and/or Bfl-FF-1 (SEQ ID No. 26). Each possibility is a separate embodiment.

According to yet additional embodiments, there is provided a composition for killing a nematode cell, the composition comprising: a recombinant cell expressing an exogenous polynucleotide encoding a polypeptide comprising an amino acid sequence at least 15% identical to the amino acid sequence of a nematode fusion protein, wherein said recombinant cell further comprises an anti nematodal agent.

According to some embodiments, there is further provided a kit comprising a composition comprising a recombinant cell expressing a fusogenic protein of nematode origin and; instructions for using said composition for the treatment of nematode infection.

These and additional benefits and features of the invention could better be understood by those skilled in the art with reference to the following detailed description taken in conjunction with the figures and non-limiting examples.

BRIEF DESCRIPTION OF THE DRAWINGS

The accompanying drawings, which are incorporated in and form a part of the specification, illustrate certain embodiments of the present invention, and together with the description serve to explain the principles of the invention. It is intended that the embodiments and figures disclosed herein are to be considered illustrative rather than restrictive. The figures are listed below.

FIG. 2A bald virus preparations (VSVΔG)

Anti AFF-1 polyclonal antibodies followed by immunogold labeling and negative stain of FIG. 2D—VSVΔG-G virus preparation, FIG. 2E—VSVΔG-AFF-1 pseudotype virus preparation.

Cryo TEM: FIG. 2F≠VSVΔG virus; FIG. 2G—VSVΔG-G; FIG. 2H VSVΔG-AFF-1.

FIGS. 2I-K—show Top (2I), Center (2J) and bottom (2K) slice from VSVΔG-AFF-1 tomogram, respectively.

FIGS. 2L-M show slices form cryoET of vesicles co-purified with VSVΔG-AFF-1 preparation displaying penta- or hexa-meric "flower" shaped complexes (Arrows). Scale bars are 100 nm and 10 nm for insets; Arrows: surface spike assemblies; Arrowheads: gold particles; White square: indicating area shown magnified in inset.

Figure 2N:
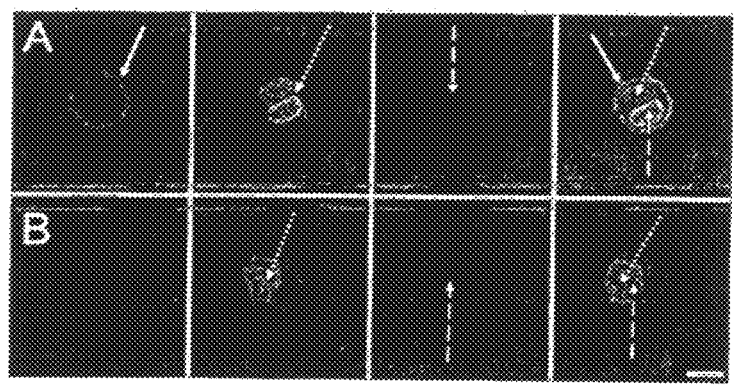
FIGS. 2A-P shows Electron Microscopy pictures of various Recombinant VSVΔGs or immunofluorescence of Sf9 cells expressing AFF-1. Negative stained vesicles were obtained from the following viruses.
FIG. 2B VSVΔG-G virus preparation.
FIG. 2C—VSVΔG-AFF-1 pseudotype virus preparations. Arrows point to surface particles.

FIG. 2N. Immunofluorescence in Sf9 cells expressing AFF-1-Flag (transfected with 3 μg/ml aff-1 plasmid (Table 2)) with either: Panel A—#8 mouse polyclonal antibodies against AFF-1, diluted 1:500 in TBST or Panel B—pre-immune serum. Secondary antibody—Alexa Fluor 568 goat anti mouse IgG (H+L, Invitrogen Cat#A11004) diluted 1:500 in TBST. Order of pictures in each panel, left to right: Panel A: AFF-1 (white, solid arrow (representing red)); Transfection marker nuclear/cytoplasmic (dashed arrow (representing green)); DAPI, DNA (Long dashed arrow (representing blue)); overly of staining. Panel B; pre-immune serum; Transfection marker nuclear/cytoplasmic (dashed arrow (representing green)); DAPI, DNA (long dashed arrow (representing blue)); overly of staining. Scale bar is 10 μm.

Figure 2O:
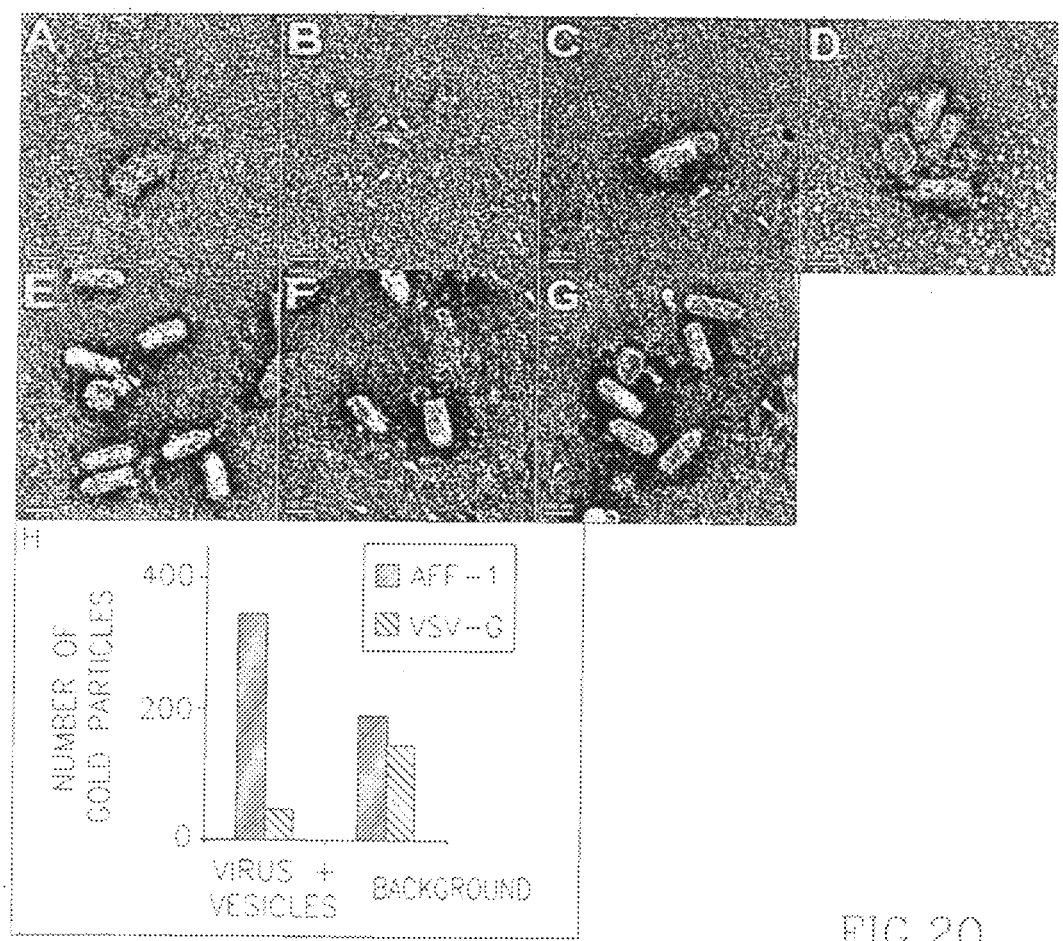
Figure 2P:
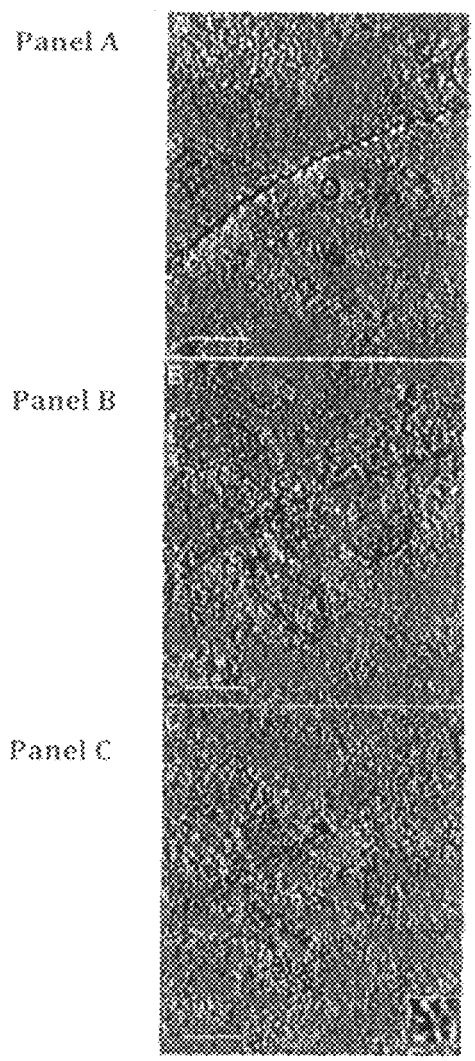

FIG. 2O (panels A-H) demonstrate quantification of immunogold labeling. Panel A—shows pictograms of immunogold labeled VSVΔG-AFF-1 (asterisk). Panel B shows pictograms of immunogold labeled vesicle isolated from VSVΔG-AFF-1 prep (asterisk) with some background staining (arrowheads). Panel C—shows pictograms of immunogold labeled VSVΔG-AFF-1 (center) with some background staining (arrowheads). Panel D—shows pictograms of immunogold labeled vesicles and VSVΔG-AFF-1 viruses. Panel E—shows pictograms of VSVΔG-G stained with anti AFF-1 (negative control) antibody showing some non specific immunogold labeling (arrowheads). Panel F—shows pictograms of VSVΔG-G (center) with some background staining (arrowheads). Panel G—shows pictograms of immunogold labeled vesicles isolated from VSVΔG-G prep (asterisk) with some background staining (arrowheads). Panel H—shows bar graphs representing number of gold particles (Y axis) recognizing viruses and vesicles versus background of VSVΔG-AFF-1 or VSVΔG-G samples stained with anti-AFF-1. Anti-AFF-1 show specific virus/vesicle recognition of VSVΔG-AFF-1 compared to control VSVΔG-G. The difference in background staining between VSVΔG-AFF-1 and VSVΔG-G grids is not statistically significant (P=0.4588; n=30 quantified images per virus);

FIG. 2P (panels A-C) shows slices from cryoET of vesicles that co-purified with VSVΔG-AFF-1. Panel A—Top; Panel B—center; Panel C—bottom of slice from cryoET of vesicle preparations displaying penta- or hexameric "flower" shaped assemblies, Scale bars are 100 nm and 10 nm for the inset; white box: magnified area shown in inset.

FIGS. 3A-O—Fusion of BHK-AFF-1 and BHK-EFF-1 cells. FIGS. 3A-C are schematic illustrations of experimental design of a color mixing assay. FIG. 3D is a pictogram showing Negative control. Mixed cells co-transfected with empty vector and a (red) cytoplasmic marker (RFPnes) or a (cyan) nuclear marker (CFPnls) showed no color mixing. Scale bar is 100 μm.

FIG. 3E is a pictogram showing BHK-AFF-1 expressing cells (solid arrow (representing Red)) and BHK-EFF-1 expressing cells (dashed arrow (representing Cyan)) that were mixed. Hybrids express cyan nuclei and red cytoplasm (as indicated by the solid, short arrow heads).

FIGS. 3F-H show pictograms of: FIG. 3F: AFF-1 expressing BHK cells with (red) cytoplasm (represented by solid arrow); FIG. 3G: EFF-1 expressing BHK cells with (cyan) nuclei (represented by dashed arrow); FIG. 3H: BHK cells with (red) cytoplasm (represented by solid arrow) surrounding, two (cyan) nuclei (represented by dashed arrows) appeared following expression of AFF-1 in BHK cells, expression of EFF-1 expression in BHK cells and mixing of the cells. (Scale bar is 10 μm.)

FIGS. 3I-K show pictograms of: FIG. 3I: AFF-1 expressing BHK cell with (red) cytoplasm (solid arrow, representing red cytoplasm); FIG. 3J: AFF-1 expressing BHK cell with (cyan) nuclei (dashed arrow, representing cyan nuclei); FIG. 3K: BHK cell with red cytoplasm (solid arrow, representing red cytoplasm) surrounding cyan nuclei (dashed arrow, representing cyan nuclei), which appeared following mixing of the cells.

FIGS. 3 L-O show quantification of the content mixing experiments in pie graphs, which represent the fraction of multinucleated cells (2 nuclei or higher). Results are mean of four independent experiments (n≥1000 total cells): FIG. 3L is a pie graph of quantity of cells transfected with Empty vectors. All multinucleated cells are bi-nucleated (total dividing cells 4%); FIG. 3M is a pie graph of quantity of AFF-1 expressing cells (solid arrow (representing red)) mixed with empty vector transfected cells (dashed arrow (representing cyan)). Elevation in multinucleation was only observed for AFF-1 expressing cells (solid arrow, 11%; dashed arrow, 3%). One cell with a single nucleus expressing both markers (red and cyan) was observed; FIG. 3N is a pie graph of quantity of AFF-1 expressing cells (solid arrow (representing red)) mixed with AFF-1 expressing cells (dashed arrow (representing cyan) resulting in four cell populations—mononucleated white and multinucleated red (represented by solid arrow, 13%), cyan (represented by dashed arrow, 12%) and mixed (represented by long dashed arrow (purple); 11%); FIG. 3O is a pie graph of quantity of AFF-1 expressing cells (solid arrow (representing red), 9%) mixed with EFF-1 expressing cells (dashed arrow (representing cyan), 11%). AFF-1 and EFF-1 expressing cells fuse (long dashed arrow (representing purple) 18%).

Figure 4A:
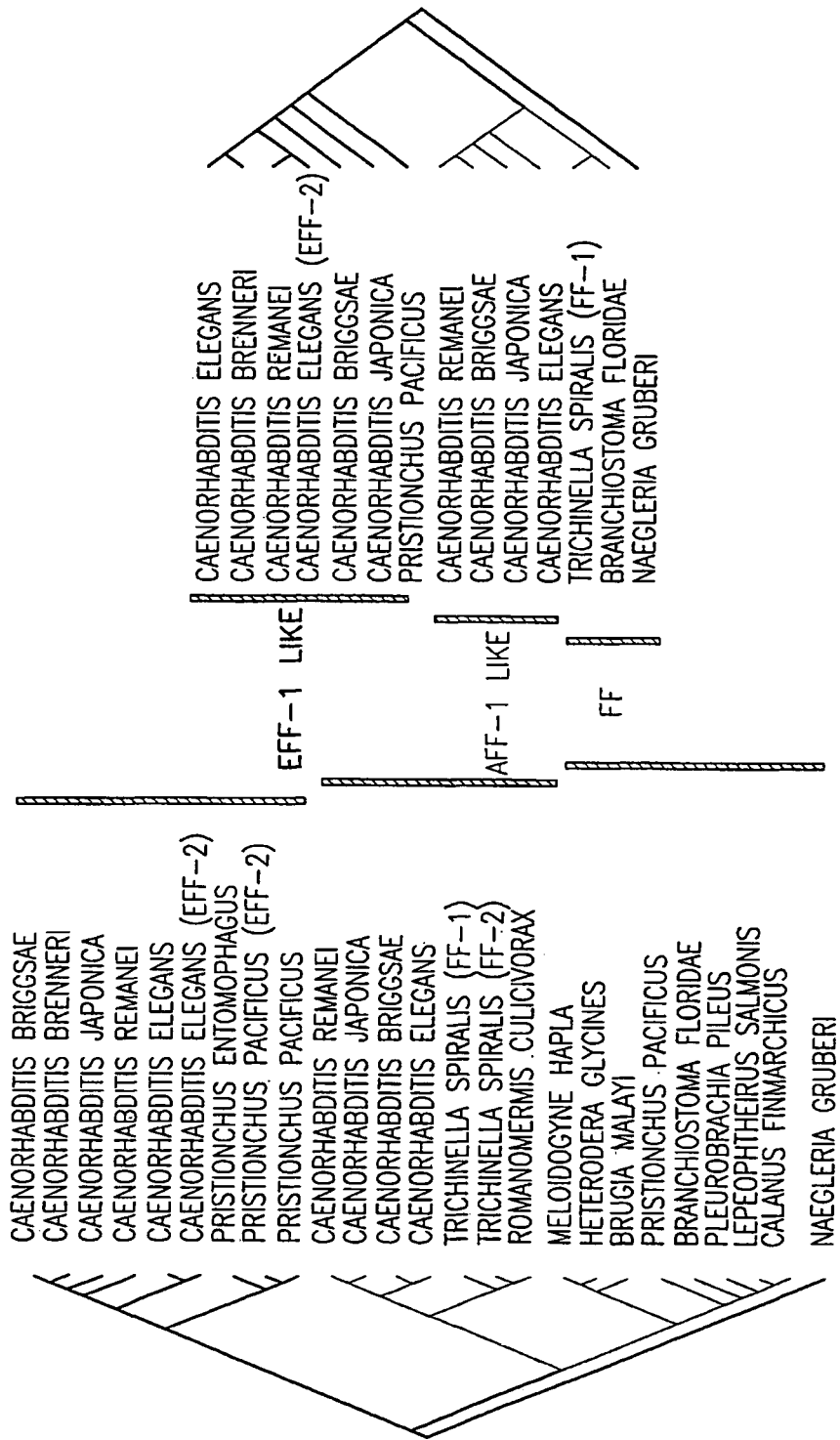

FIGS. 4A-F The FF Family of Eukaryotic Cell-Cell Fusogens: FIG. 4A shows scheme of two trees produced using maximum parsimony analysis. Phylogenic relationships of 25 taxa (left) and 14 taxa (right) based on either the TGFβ-RI like domain or the full length extracellular domain respectively, show classification of FF proteins into three subgroups (EFF-1-like, AFF-1-like and FF). FIG. 4B-E shows pictograms of immunofluorescence with anti-Flag antibodies (solid arrow (representing green)), and nuclei DAPI staining (dashed arrow (representing blue)) on BHK cells transfected with: FIG. 4B—empty vector; FIG. 4C—aff-1; FIG. 4D—Tsp-ff-1; and FIG. 4E—Bfl-ff-1. Co-transfection marker (original color—red). The images are representative of hundreds of fields in at least eight independent experiments. Scale bars represent 20 μm. For cells not expressing the construct (no red fluorescence) only the nuclei are visible. FIG. 4F shows bar graphs illustrating fusion index for transfected BHK cells expressing FF proteins and negative control. Data are means±SE. Empty vector, n=14, aff-1, n=14, Tsp-ff-1, n=8, n=9; n represents number of experiments.

Figure 5:
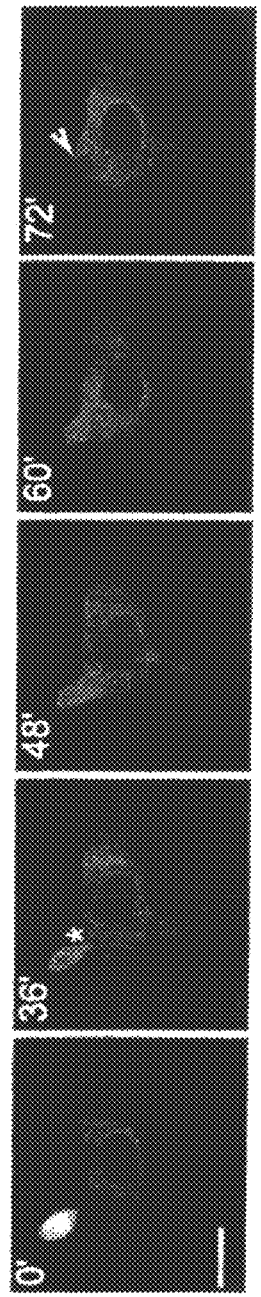

FIG. 5 shows time lapse images of AFF-1-mediated fusion of mammalian cells. BHK cells co-transfected with AFF-1 and pRFPnes (white). The cells fuse as indicated by the diffusion of the marker from the brighter cell (36 min, asterisk) to the larger cell. After 72 minutes the marker is homogenously distributed and excluded from the second nucleus (arrowhead). Scale bar 20 μm. n>3 experiments.

Figure 6A:
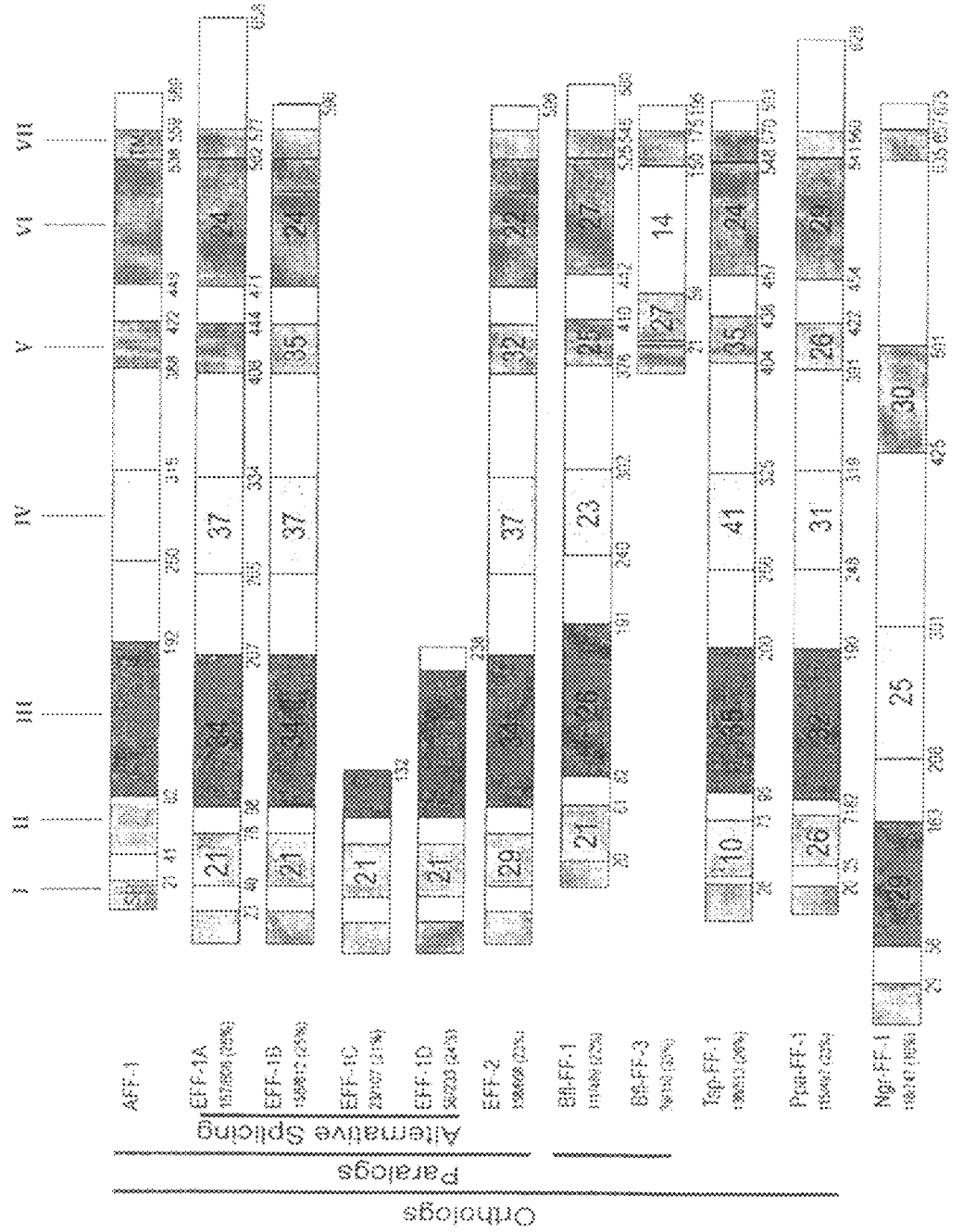
Figure 6B:
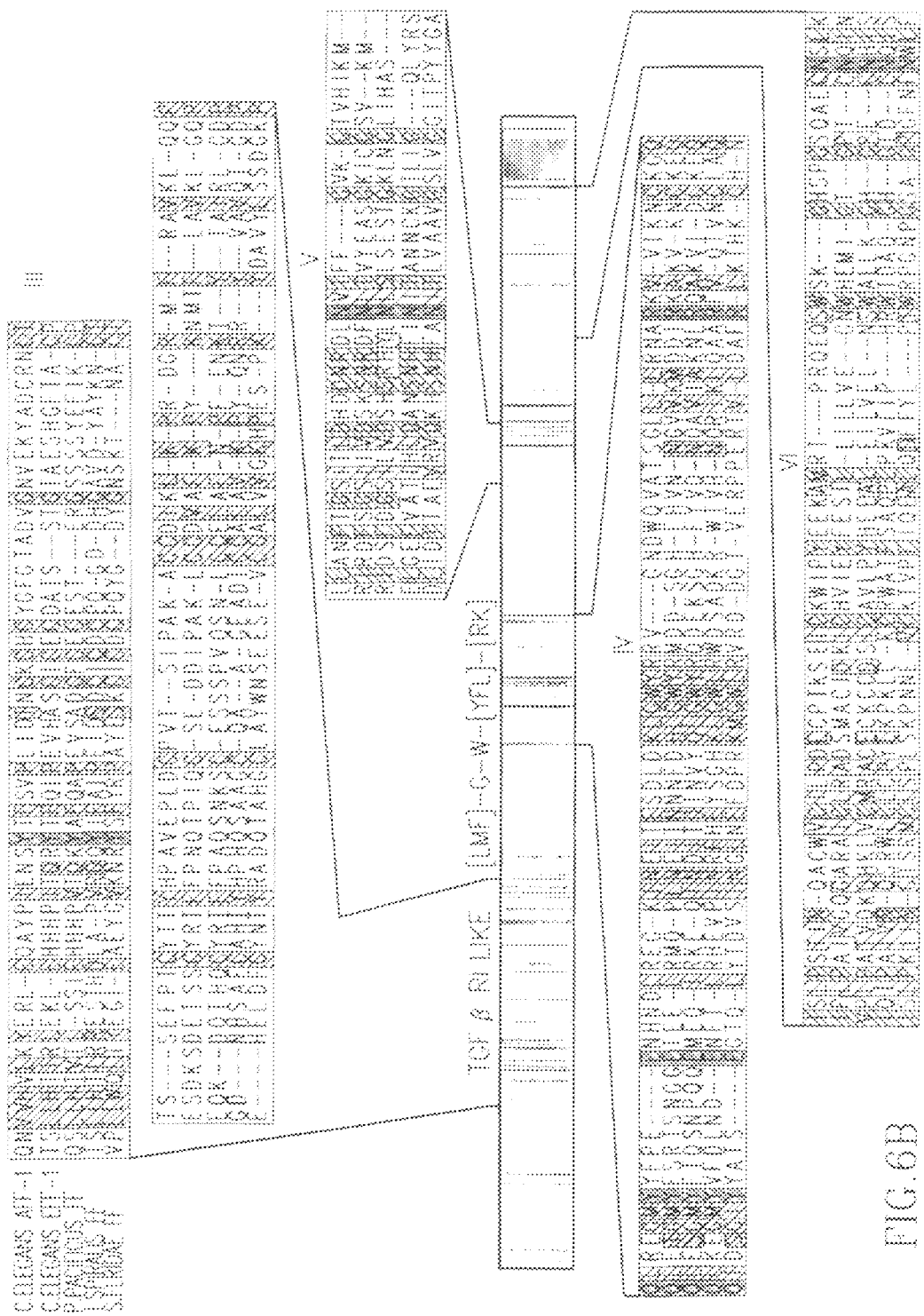
Figure 6C:
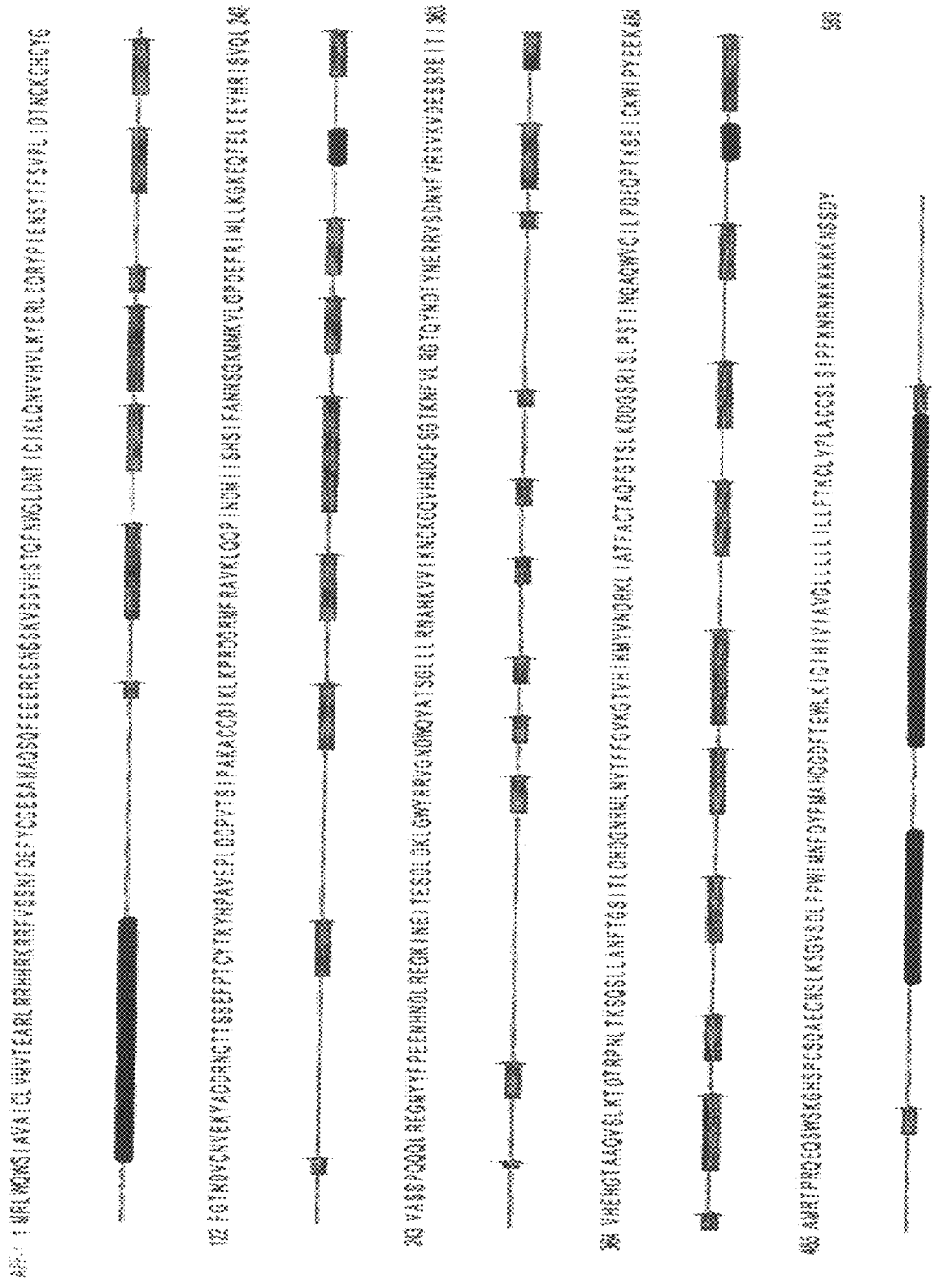

FIGS. 6A-C shows sequence analysis of FF proteins. FIG. 6A shows distribution of conserved sequence motifs in FF paralogs and orthologs. Sequence motifs are numbered (color coded): I (representing Green)—Signal peptide (SP);

II (representing Pink)—Pro-domain; III (representing Brown)—TGFβ-RI-like domain; IV (representing Yellow)—"[LMF]-G-W-[YFL]-[RK] motif"; V (representing Cyan)—Putative protein-protein interaction domain; VI (representing Purple)—Membrane proximal stem domain, VII (representing Ocher)—Transmembrane domain (TM). C. elegans paralogs are listed by gene name AFF-1, EFF-1, EFF-2 (C26D10.7). EFF-1 Alternative splicing variants (EFF-1 A-D) are also shown. Overall sequence identity to AFF-1 is indicated under the gene name. Local sequence identity to AFF-1 (%) is indicated within each domain. Sequence limits are indicated under the illustration unless it is identical to previously shown schematic as in the case for EFF-1 isoforms. Sequences retrieved from B. floridae v2.0 assembly are listed as Bf-FF-1 and FF-3 which correspond to protein model id's 104514 and 104513 respectively. T. spiralis (Tsp FF-1) and P. pacificus (Ppa FF-1) correspond to gi|162730680 and Contig235.2 of the PpaFreeze1.bases database. Sequences retrieved for N. gruberi (Ngr-FF-1) correspond to gi|284087402 (Table 4). Accession numbers/ database identifier of the various sequences are listed in Table 4. Annotation was preformed as previously described (2). FIG. 6B shows schematic representation of the multiple sequence alignment of FF proteins. Sequence alignment of conserved sequence motifs is shown. Alignment (color) code was according to the Clustal X color scheme with 40% conservation color increment in Jalview software (16). FIG. 6C shows schematic representation of secondary structure prediction of AFF-1 based on the multiple sequence alignment of FF proteins. The consensus prediction is shown— alpha helices are marked as tubes (originally represented by red tubes), and beta sheets as arrows (originally represented by green arrows).

FIGS. 7A-D—FF-1 protein from P. pacificus can fuse C. elegans cells. The gene Ppa-ff-1 (Table 2) was PCR amplified from P. pacificus genomic DNA and cloned downstream to a heat shock promoter (hsp16.2) from C. elegans. Transgenic worms were generated using microinjection of wild type stain (N2) and crossed to eff-1 (ok1021) (8). Ectopic cell fusion was visualized by following the disappearance of an apical junction marker from fusing membranes (AJM-1::GFP) using confocal Z series reconstruction (2, 8) (n=9 embryos). FIGS. 7 A-D shows pictograms of ectopic cell fusion of transgenic worms (FIGS. 7A-B are fluorescence images, FIG. 7C is bright field and FIG. 7D is a merger of images of FIGS. 7B and 7C). 1.5-fold stage embryos, anterior to the left and ventral down. The effect of ectopic cell fusion is lethal. Scale bars are 10 μm. FIG. 7A shows a wild type embryo, two dorsal hypodermal cells undergo normal fusion (represented by asterisk). Unfused junction is marked with an arrow. FIG. 7B-D—eff-1 mutant embryo expressing hsp::Ppa-ff-1 (SEQ ID NO:20) after heat shock. The disappearance of apical junctions between individual cells suggests that Ppa-FF-1 mediates fusion of the hypodermal cells in an eff-1 independent manner.

Figure 8B:
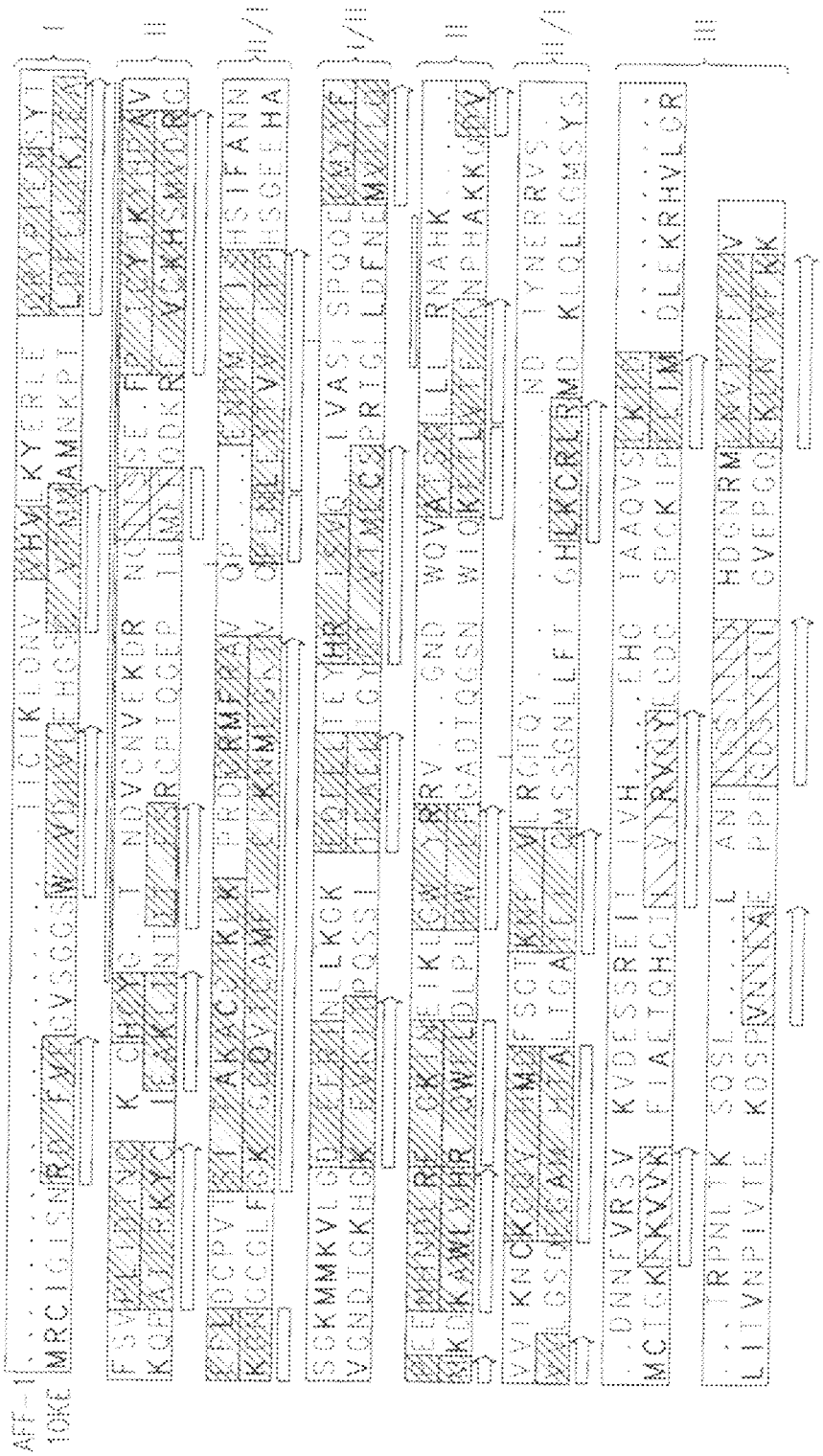

FIGS. 8A-B. shows a schematic model of predicted structural homology of AFF-1 to class II viral fusogens. FIG. 8A—Top: model of Dengue 2 envelope glycoprotein E (accession: GI: 34811077/8). The following domains are shown: (Domain II (representing pink), Domain I (representing gray), Domain III (representing yellow) of the resolved structure of Dengue 2 E protein (PDB:1oke)). Bottom (boxed)—Model of AFF-1 putative fusion ("fusion loop") and ij ("jl loop") loops.

FIG. 8B—(B) Structural alignment of the Dengue 2 E protein and of the predicted secondary structure of AFF-1. Fusion loop and ij loop are indicated by lines above the text. Alignment color is according to the Clustal X coloring scheme. Beta sheets—boxes and black arrows below text; Alpha helixes—boxes and black lines below text. Background: Domain II ((representing Pink), indicated by "II"), Domain I ((representing Gray), indicated by "I"), Domain III ((representing Yellow), indicated by "HI").

DETAILED DESCRIPTION OF THE INVENTION

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

The term "construct", as used herein, refers to an artificially assembled or isolated nucleic acid molecule which may include one or more nucleic acid sequences, wherein the nucleic acid sequences may include coding sequences (that is, sequence which encodes an end product), regulatory sequences, non-coding sequences, or any combination thereof. The term construct includes, for example, vector but should not be seen as being limited thereto.

"Expression vector" refers to constructs that have the ability to incorporate and express heterologous nucleic acid fragments (such as, for example, DNA), in a foreign cell. In other words, an expression vector comprises nucleic acid sequences/fragments (such as DNA, mRNA, tRNA, rRNA), capable of being transcribed. Many prokaryotic and eukaryotic expression vectors are known and/or commercially available. Selection of appropriate expression vectors is within the knowledge of those having skill in the art.

The term "expression", as used herein, refers to the production of a desired end-product molecule in a target cell. The end-product molecule may include, for example an RNA molecule; a peptide or a protein; a virus; and the like; or combinations thereof.

As used herein, the terms "introducing" and "transfection" may interchangeably be used and refer to the transfer of molecules, such as, for example, nucleic acids, polynucleotide molecules, vectors, and the dike into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. The transfection of the cell may be performed on any type of cell, of any origin, such as, for example, human cells, animal cells, plant cells, virus, nematode cell, stem cells, cancer cells, and the like. The cells may be selected from isolated cells, tissue, cultured cells, cell lines, cells present within an organism body, and the like.

As referred to herein, the terms "nucleic acid", "nucleic acid molecules" "oligonucleotide", "polynucleotide", and "nucleotide" may interchangeably be used herein. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, tRNA, shRNA, siRNA, miRNA, and the like. The terms further include oligonucleotides composed of naturally occurring bases, sugars, and covalent internucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "homology", "homologous" and "homologs" as used herein are directed to sequence similarity between different sequences of peptides or different sequences of nucleic acids. For example, if two or more proteins have highly similar amino acid sequences, it is likely that they are homologs. In some embodiments, homologs may include homologs within species, between species and/or between phyla. In some embodiments, the term homologs include orthologs and/or prologs.

As referred to herein, the term "exogenous gene" is directed to a gene (or any part thereof) which is introduced from the exterior into a cell. In some embodiments, the exogenous gene is inserted in the form of a polynucleotide (for example, DNA, RNA, and example, in the form of an expression vector. In some embodiments, the exogenous gene is capable of being expressed in the cell. In some embodiments, the exogenous gene is overexpressed within the cell.

As referred to herein, the term "Kill" with respect to a cell/cell population/organism is directed to include any type of manipulation that will lead to the death of that cell/cell population/organism.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a subject involves prevention of a particular disorder, or infection or adverse physiological event in a susceptible subject as well as treatment of a clinically symptomatic subject.

As referred to herein, the terms "anthelmintic(s)" or "antihelminthic(s)" or "anti-nematode" may interchangeably be used. The terms are directed to agents/compositions that are directed against helminths (parasitic round worms or nematodes). The agents/compositions may include various molecules, such as, for example, but not limited to chemical compound, drug, nucleic acid molecule (such as, for example, DNA, RNA, siRNA, ribozyme, modified nucleic acids and the like), a protein or a peptide (such as, for example, an enzyme, an antibody, and the like), a toxin, or combinations thereof. In various embodiments, the antihelminthic may be used to stun, inhibit/suppress growth, and/or kill helminths cells. In some embodiments, the term "anti-nematodal" relates to antihelminthic which are directed against nematodes. In some embodiments, the terms antihelminthic and antinematodal may interchangeably be used. In some embodiments, the antinematodal is nematocidal (that is an agent that is able to kill the nematode/nematode cell). In some embodiments, the antinematodal is nematostatic (that is an agent that is able to stun/inhibit/suppress growth of the nematode/nematode cell).

As referred to herein, the terms "fusion protein", "fusogen" and "fusogenic protein" may interchangeably be used. The terms are directed to a protein/peptide which is able to induce/mediate cell to cell fusion, for example, through fusion of the lipid bi-layers of the cells. In some embodiments, the fusogenic protein is an endogenous protein (that is, a protein encoded by the authentic genome of the cell and is usually expressed by an unmodified cell). In some embodiments, the fusogenic protein is an exogenous protein (that is, a protein which is encoded by a foreign gene introduced into the cell). In some embodiments, the fusogenic protein comprises a portion/domain of the full length fusogenic protein. The portion of the fusogenic protein may be any domain of the fusogenic portion or combinations of such domains, such as, for example, Signal peptide (SP) domain; Pro-domain; TGFβ-RI-like domain; "[LMF]-G-W-[YFL]-[RK] motif" domain; the Putative protein-protein interaction domain; Membrane proximal stem domain, Trans-membrane domain (TM), Fusion loop, and the like, or any desired peptide derived from the fusogenic protein sequence.

As referred to herein, the term "FF protein(s)" is directed to Fusion Family proteins. The term "CeFF proteins" is directed to FF proteins of *C. elegans* origin. Members of the FF proteins include, for example, AFF-1 and/or EFF-1 proteins and homologs thereof. Wherein said fusogenic protein of nematode origin it is meant to include members of the Fusion Family (FF) proteins as well as homologs thereof, wherein homologs may include homologs within species, between species and/or between phyla. In some embodiments, the term "homologs" include orthologs and/or paralogs. As referred to herein, homologs of the FF Family protein are proteins that share primary and/or secondary amino acid sequence signatures including a pattern of cysteins in the ectodomain of the type I membrane glycoprotein. To consider membership to the FF family the candidate protein is to share at least 15% identity or similarity with a known FF or protein of related secondary or tertiary structure (as further demonstrated in FIGS. 6A-C). In some embodiments, an FF protein may be selected from any of the FF proteins listed in Table 4 below herein. In some exemplary embodiments, FF proteins may be selected from, but no limited to: CeAFF-1 (SEQ ID NO: 23), CeEFF-1 (SEQ ID NO:24), tsp-FF-1 (SEQ. ID. NO: 25), Bfl-FF-1 (SEQ ID NO: 26), CeEFF-2, Cbr-aff-1, Cbr-eff-1, Cre-aff-1, Cre-eff-1, Cs5-AFF-1, Cs5-EFF-1, Cs7/9-AFF-1, Cs7/9-EFF-1, Cs11-FF, Ppa-FF-1, Ppa-FF-2, Ppa-FF-3, Pen-FF-1, Pma-FF-1, Tsp-ff-2, Tps-FF, Tpa-FF, Min-FF, Mar-FF, Mha-FF, Gpa-FF, Gpa-FFA, Gpa-FFB, Aca-FF, Bma-FF-1, Hco-FF, Asu-FF, Oti-FF, Oti-EFF-1, Dim-FF, Hao-FF, Lsi FF 1, Lsi-FF-2, Hgl-FF, Tmu-FF-1, Tmu-FF-2, Sra-FF-1, Sra-FF-2, Sra-FF-3, Ovo-FF, Tci-FF, Wba-FF, Llo-FF, Bfl-FF-3, Ppi-FF, Cfi-FF, Lsa-FF, Ngr-FF-1, Ngr-FF-2, Ngr-FF-3, Ngr-FF-4, Bxy-FF-1, Bxy-FF-2, Can-FF, Hba-FF-1, Hba-FF-2, Rcu-FF, Hpo-FF, Ana-FF-1, Ana-FF-2, Mle-FF-1A, Mle-FF-1B, Mle-FF-2, Mel-FF-3, Mel-FF-4, Mel-FF-5, Mel-FF-6 or any combination thereof. Each possibility is a separate embodiment.

As used herein, the term "pseudotyped virus" relates to a virus in which the endogenous viral envelope proteins have been replaced by envelope proteins from other sources, such as, for example, from other viruses, by exogenous proteins or peptides (for example, of nematode origin), and the like.

As referred to herein, the term "virus cell" is meant to include a virus, viral particle, viral envelope, viral vector and/or pseudotyped virus.

As used herein, the term "bald virus" relates to an enveloped viral particle or a pseudoviral particle lacking one or more viral envelope proteins.

As used herein, the term "homotypic" with respect to fusion is directed to fusion between cells that express the same fusion protein, or cells that express fusogenic protein of the same family.

As used herein, the term "non-insect cell" is directed to include cells which are not of insect origin. The term includes, for example, such cells as, mammalian cells, avian cells, plant cell, viral particle, human cells, animal cells, and the like.

As referred to herein, where a color is mentioned by name with respect to a figure (for example, "red", "cyan", "purple", "green", "pink", "yellow", etc.) it refers to the color as can be identified in the figure when reproduced in color scale. Where applicable, and as indicated in the brief description of the Figures, where a color is mentioned it is further indicated by an identifier, such as, arrow (solid, dash, long dash arrow head, and the like), asterisk, box, numerical or any other indication. The original figures reproduced in color can be found in publication by some of the inventors of the present application (Avinoam, et. al. (19), the contents of which is incorporated by reference herein in its entirety.

According to some embodiments, and as exemplified herein, nematode fusogenic proteins of the FF family and homologs thereof, such as for example, CeFF proteins, may be capable of mediating fusion of a virus to a cell (such as, for example, a mammalian cell), when the FF proteins are expressed and presented on the membranes of the virus and the cell. In some embodiments, the FF proteins expressed by the virus are replacing the endogenous fusogenic proteins of the virus. In some embodiments, the fusogenic protein expressed by the virus is the same fusogenic protein as that expressed by the cell. In some embodiments, the fusogenic protein expressed by the virus is not the same fusogenic protein as the fusogenic protein expressed by the cell, but rather a family member thereof. For example, the fusogenic protein expressed by both the virus and the cell is AFF-1 protein or homologs thereof. For example, as further shown below, the fusion protein expressed by the virus is AFF-1 whereas the fusion protein expressed by the cell is EFF-1, and vice versa. Accordingly, in some embodiments, a nematode fusogenic protein may replace the endogenous viral fusogen as the minimal fusogenic machinery. Moreover, the infection biology of the virus may be transformed from a mechanism in which the endogenous viral fusogen, (for example, VSVG), is required only in the virus, to a homotypic, fusion protein-dependent mode-of-action in which the fusogen(s) is expressed in the membranes of both the virus and the target cell.

According to some embodiments, the fusion family protein may be any member of the family of fusogenic proteins that may be of nematode origin, or even of other phylum, such as, for example, chordates. Sequence comparisons (ref. 4, and herein) identified putative FF members in thirty five nematode species, suggesting that the FF family is conserved in the phylum Nematoda (4). In addition, similar proteins were found in the arthropods *Calanus finmarchicus* and *Lepeophtheirus salmonis* (Crustacea), the ctenophore *Pkurobrachia pileus*, the chordate *Branchiostoma floridae* (order Amphioxi) and the protist *Naegleria gruberi*, (as shown in FIG. 4A and Table 4 below), suggesting that FF proteins are conserved in at least four animal phyla and one protist. Phylogenic analysis of full and partial FF sequences revealed that FF proteins may be classified into three subgroups (EFF-1-like, AFF-1-like and FF; FIG. 4A). To further characterize the molecular conservation of FF proteins, a multiple sequence alignment (FIG. 6A) was generated and determined that FF proteins share a common organization of putative conserved domains (FIG. 6B). For example, FF proteins share a pattern of cysteins in the TGFb-RI-like domain (Domain III in FIGS. 6A-C), suggesting they may be conserved at the level of protein structure. As shown in FIG. 6C, secondary structure predictions show that they may belong to the family of "mostly beta sheet super family"). Additionally, as further demonstrated hereinbelow, sequence structure analyses and comparisons of Hidden Markov models suggest that FF proteins may fold to resemble class II fusogens from alfa and flavi viruses.

According to some embodiments, and as further demonstrated below, FF proteins are a family of membrane fusogens in nematodes that may be interchangeable between species and even beyond the nematode phylum and hence homologs of the family can be used for fusion of cells, when expressed on the membranes of those cells. As exemplified hereinbelow (for example, in FIG. 4), various homologs of the CeFF proteins (such as, for example, Tsp-FF-1 of the *Trichinella spiralis* nematode species), EFF-1 homolog from the nematode *Pristionchus pacificu* and chordate *B. floridae* (Bfl-ff-1) of the chordates phylum) are able to fuse cells, when expressed by the cells.

According to some embodiments, Fusion Family proteins of nematode origin and homologs thereof can mediate homotypic or heterotypic fusion of a virus and a cell without additional membrane co-factors. The fusion of the virus and the cell results in infection of the cell by the virus.

According to other embodiments, the Fusion Family proteins of nematode origin and homologs thereof can mediate homotypic fusion of two cells (a first cell and a second cell), wherein the cells express the fusogenic protein of nematode origin. In some embodiments, the cells are not-insect cells. In some embodiments, at least one of the fused cells is not an insect cell. Each possibility is a separate embodiment.

According to some embodiments, the nematode may be any type of nematode. For example, the nematode may be selected from, but not limited to: *Caenorhabditis elegans, Caenorhabditis briggsae, Caenorhabditis japonica, Caenorhabditis ramanei, Caenorhabditis brenneri, Caenorhabditis sp5,7,9,11, Trichinella spiralis, Trichinella pseudospiralis, Trichinella papuae, Pristionchus entomophagus, Pristionchus maupasi, Pristionchus pacificus, Meloidogyne incognita, Meloidogyne arenaria, Meloidogyne hapla Globodera pallida, Ancylostoma caninum, Brugia Malayi, Haemonchus contortus, Ascaris suum, Oscheius tipulae, Dirofilaria immitis, Howardula aoronymphium, Litomosoides sigmodontis, Heterodera glycines, Romanomermis culicivorax, Trichuris muris, Strongyloids ratti, Onchocerca volvulus, Teladorsagia circumcincta, Wuchereria bancrofti, Loa loa*, and any other nematode known in the art. Each possibility is a separate embodiment.

According to some embodiments, in order to express an exogenous fusogenic protein in a cell, the cell may be introduced with a construct, such as, for example, an appropriate expression vector, encoding the desired fusion protein. The construct that encode for the fusogenic protein may include a plasmid, vector, viral construct, or others known in the art, used for replication and expression in the appropriate target cell (which may include, for example, mammalian cells, avian cell, plant cells, viruses, and the like). The construct may be used for transient transfection and/or stable transfection of the cells. Expression of the fusogenic protein can be regulated by any promoter known in the art to act in the target cell. Such promoters can be inducible or constitutive. Such promoters include, for example, but are not limited to: the SV40 early promoter region, the promoter contained in the 3' long terminal repeat of Rous sarcoma virus, the herpes thymidine kinase promoter, the regulatory sequences of the metallothionein gene, the viral CMV promoter, the human chorionic gonadotropin-beta promoter, and the like. Any type of plasmid, cosmid, YAC or viral vector can be used to prepare the construct which can be introduced directly into the cell, by any method known in the art. Alternatively, when the target cell is not a virus, viral vectors can be used which selectively infect the desired target cell. In some embodiments, expression of the fusogenic protein in the cell is transient. In other embodiments, expression of the fusogenic protein in the cell is chronic. In some embodiments, expression of the fusogenic protein in the cell may be inducible (that is, the fusogenic protein is expressed only under certain conditions).

According to some embodiments, there is thus provided a method for a specific, protein-mediated virus to cell fusion, wherein the virus and the cell express a fusogenic protein of the nematode family, or homologs thereof. The method includes placing/incubating/mixing the virus and the cell in close proximity, thereby allowing interaction of the fusogenic proteins which consequently may lead to fusion of the cells. According to some embodiments, the fusogenic protein is selected from AFF-1, EFF-1 and homologs thereof. In some exemplary embodiments, the fusogenic protein is a CeFF protein. In some embodiments, the same fusogenic protein is expressed on the surface of both the virus and the cell. In some embodiments, each of the virus and the cell express a different fusogenic protein, both fusogenic proteins belong to the family of Fusion Family proteins. In some embodiments, for at least one of the cells, the fusogenic protein is an exogenous protein. The method may be performed in-vitro and/or in vivo. When performed in vitro, the virus and the cell may be placed in the same growth medium and incubated under favorable conditions which allow the growth of the cells.

According to some embodiments, there is further provided a method for a targeted and specific fusion of a nematode cell and a virus expressing an exogenous fusogenic protein of nematode origin, wherein the exogenous fusogenic protein expressed by the virus replaces an endogenous fusogenic protein that may be expressed by the virus.

In some embodiments, the virus expressing the exogenous fusogenic protein of nematode origin may be any type of virus capable of fusing with other cells. In some embodiments, the native (unmodified) virus may be capable of inducing fusion by virtue of endogenous fusogenic proteins expressed by the unmodified virus. For example, but without limitation, the virus may be of the retrovirus family (for example, HIV, MLV); Hepadnavirus, Poxyvirus, Rhabdoviridae viruses (for example, Vesicular stomatitis virus (VSV)); Paramyxoviruses; Herpes viruses; Coronavirus, and the like, or combination thereof.

According to further embodiments, there is thus provided a method for the targeted killing or inhibition of a nematode/nematode cell, the method comprises contacting the nematode with a virus expressing an exogenous fusogenic protein of nematode origin, thereby allowing fusion of the virus to a cell of the nematode. Consequent to the fusion between the virus and the nematode cell, the virus may induce lysis of the nematode/nematode cell and/or inhibit the growth of the nematode/nematode cell. The nematode may further become unlivable if too many of its cells are killed.

According to further embodiments, there is provided a method for a specific, protein mediated, cell to cell fusion. The method includes having the cells express a fusogenic protein on their membranes and mixing/placing/incubating the cells in close proximity, thereby allowing interaction of the fusogenic proteins which may lead to fusion of the cells. The protein which mediates the fusion may be a fusogenic protein of nematode origin or homologs thereof, and is expressed on the surface of the cells and thereby allows fusion of the cells. According to some embodiments, the fusogenic protein is selected from AFF-1, EFF-1 and homologs thereof. In some embodiments, the fusogenic protein is a CeFF protein. In some embodiments, the same fusogenic protein is expressed on the surface of both cells. In some embodiments, each cell expresses a different fusion protein, both fusogenic proteins belong to the family of Fusion Family proteins. In some embodiments, the fusogenic proteins are endogenously expressed proteins. In some embodiments, for at least one of the cells, the fusogenic protein is an exogenous protein. In some embodiments, the cells are of similar origin. In some embodiments, the cells are of different origin. For example, the cells may be of human origin, animal origin, plant origin, avian origin, and the like. In some exemplary embodiments, both cells (i.e. the first cell and the second cell) express an exogenous Ce-AFF-1 protein. In some exemplary embodiments, both cells (i.e. the first cell and the second cell) express an exogenous Ce-EFF-1 protein. In some embodiments, the first cell expresses an exogenous Ce-AFF-1 protein and the second cell expresses a Ce-EFF-1 protein. In some embodiments, upon fusion of the cells (i.e. the first cell and the seconds cell), and hybrid cell is formed. In some embodiments, the hybrid cell contains two nucleus.

According to additional embodiments, the method for the specific, protein mediated, cell to cell fusion may be used to specifically target antinematodal agents to nematodes. In such embodiments, fusion of a nematode cell to a foreign cell is dependant on the expression of a fusogenic protein of nematode origin (or homologs thereof) in the membranes of both fusing cells, wherein the fusogenic proteins may be identical or different. In some exemplary embodiments, one cell is of nematode origin (endogenously expressing the fusion protein) and the second cell is of different/foreign origin (such as, for example, of viral origin, plant origin, mammalian origin, avian origin, insect origin), wherein the second cell exogenously expresses a fusogenic protein of nematode origin. The second cell may comprise one or more antinematodal agents that may include any antinematodal agent known in the art or to be developed/identified in the future. The antinematodal agent that is comprised in the cell may be further carried in a carrier within the cell, wherein the carrier is configured to protect the agent within the cell. The carrier may include, for example, such carriers as, liposomes, vacuoles, capsules, microspheres, micelles, and the like. In some embodiments, the antinematodal agent is encoded/produced by the cell. Upon specific fusion of the cells, the antinematodal agent may be released/expressed and exert an effect on the nematode. The effect may be, for example, kill, stun, and/or inhibit/suppress growth of the nematode.

According to some exemplary embodiments, the antinematodal agent may be selected from, but not limited to: a chemical compound (such as, for example, but not limited to: organophospates, carbamates, imidazole derivatives, such as, for example, benzimidazole, Levamisole, Fumigant nematicides, macrolides, avermectin, milbemycin and the like); a nucleic acid (such as, for example, antisense DNA molecules directed against nematode genes; siRNA molecules directed against nematode genes, and the like); proteins (such as, for example, but not limited to: an enzyme capable of cleaving a nematode protein, an antibody directed against a nematode protein); toxins, antibodies and combinations thereof.

According to further embodiments, the method for the specific, protein mediated, cell to cell fusion may thus be used for the treatment of parasitic nematode infection of various organisms (such as, for example, animals and humans) and plants. In some embodiments, the method may include inducing one or more cells of the organism/plant to be treated to express a fusogenic protein of a nematode origin and an antinematodal agent, whereby upon expression of the fusogenic protein by the cell, a nematode infecting the organism or plant is fused to said cell expressing the fusion protein, thereby exposing the nematode to the antinematodal agent.

In some embodiments, a transgenic plant is provided, in which at least some of the plant cells have been modified to express a fusogenic protein of the nematode family and optionally further express an antinematodal agent (such as, for example a protein or a peptide having antinematodal effect, nucleic acid sequence capable of exerting an antinematodal effect, and the like). Upon infection of the transgenic plant with a nematode, the nematode cells will fuse with the plant cells expressing the fusogenic proteins, and the antinematodal agent comprised/encoded by those cells may exert a deleterious effect on the nematode, such as, for example, kill the nematode and/or inhibit/suppress its growth. In some embodiments, the expression of the nematode fusogenic protein by plant cells is constitutive (that is, the cells constitutively express the nematode fusion protein). In some embodiments, the expression of the nematode fusogenic proteins by plant cells are induced under different conditions (such as, for example, different lighting conditions, different watering conditions, different temperatures, different humidity, and the like, or combinations thereof).

According to some embodiments, the stable or transient expression of a nematode fusogenic protein in plants may be achieved by stable or transient transfection of plant cells with a nucleic acid encoding a nematode fusogenic protein. In stable transformation, the nucleic acid molecule encoding a nematode fusogenic protein is integrated into the plant genome, and as such it represents a stable and inherited trait. In transient transformation, the nucleic acid molecule is expressed by the cell transformed but not integrated into the genome, and as such represents a transient trait.

There are various methods of introducing foreign genes into both monocotyledonous and dicotyledonous plants. The principal methods of the stable integration of exogenous DNA into plant genomic DNA include two main approaches: (i) *Agrobacterium*-mediated gene transfer, which includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation. A supplementary approach employs the *Agrobacterium* delivery system in combination with vacuum infiltration. The *Agrobacterium* system is especially useful for in the creation of transgenic dicotyledenous plants. (ii) Direct DNA uptake. There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

Following stable transformation, plant propagation then occurs. The most common method of plant propagation is by seed. Another method of regenerating a transformed plant is by micropropagation, which provides a rapid, consistent reproduction of the transformed plants.

Transient transformation of, for instance, leaf cells, meristematic cells, or the whole plant may also be used.

Transient transformation can be effected by any of the direct DNA transfer methods described above or by viral infection using modified plant viruses.

Viruses that useful for the transformation of plant hosts include, for example, cauliflower mosaic virus (CaMV), tobacco mosaic virus (TMV), and baculovirus (BV). In some embodiments, pseudotyped BD virus expressing FF proteins can also be used to deliver toxins, nucleic acids and other molecules.

In addition, the nucleic acid molecule encoding a nematode fusogenic protein can also be introduced into a chloroplast genome.

According to additional embodiments, treatment of parasitic nematode infection of organisms such as mammals, avians, rodents, and the like, may include providing the infected organism with a composition (such as, for example, a pharmaceutical composition), which includes a virus particle/viral vector, which is genetically engineered to express an exogenous fusogenic protein of the nematode family. In some embodiments, the virus does not express an endogenous fusogenic protein. In exemplary embodiments, the viral endogenous protein is replaced by a fusogenic protein of the nematode origin. The virus cell/viral vector of the composition does not affect any of the cells of the organism, and upon specific fusion with a nematode cell, can induce killing or inhibition of growth of the nematode. The composition may be formulated by any method known in the art, such as disclosed, for example in the latest edition of "Remington's Pharmaceutical Sciences," Mack Publishing Co., Easton, Pa., which is herein fully incorporated by reference. The composition may further include one or more excipients, as known in the art. The composition may be administered by any administration route, such as, for example, oral, rectal, transmucosal, especially trans-nasal, intestinal, or parenteral delivery, including intramuscular, subcutaneous, and intramedullary injections, as well as intrathecal, direct intraventricular, intravenous, intraperitoneal, intranasal, or intraocular injections. In some embodiments, the composition is formulated for veterinary use. In some embodiments, the composition is in form of a viral vector, wherein administration of viral vectors can be performed by, for example, intravenous or subcutaneous injection into the organism.

Following injection, the viral vectors can circulate until they recognize nematode cells, whereby they viral vector fuses to the nematode cells and induce their killing or suppression of their growth.

In some embodiments, the virus cell/viral vector, which is genetically engineered to express an exogenous fusogenic protein of the nematode family may be integrated into the genome of the treated organism.

In some embodiments, a transgenic animal is provided, in which at least some of the cells have been modified to express a fusogenic protein of the nematode family and optionally further express an antinematodal agent (such as, for example a protein or a peptide having antinematodal effect, nucleic acid sequence capable of exerting an antinematodal effect, and the like).

According to some embodiments, there is provided a method for treating a nematode infection in a subject, comprising administering to the subject a composition comprising a cell expressing an exogenous fusogenic protein of the nematode family, wherein fusion of said cell of the composition and a nematode cell infecting the subject, may lead to, the death and/or inhibition of growth of the nematode, thereby treating the nematode infection. In some embodiments, the subject is human. In some embodiments, the composition is a pharmaceutical composition that may be formulated by any method known in the art. In exemplary embodiments, the composition is formulated to be administered orally and to release the cell expressing the nematode fusogenic protein in the intestines.

In additional embodiments, there is provided a use of a composition comprising a cell expressing an exogenous nematode fusogenic protein and optionally an antinematodal agent, for the treatment of nematode infection in a subject in need.

According to some embodiments, there is provided a method for treating nematode infection in an animal, comprising administering to the animal a composition comprising a cell expressing an exogenous fusogenic protein of the nematode family, wherein fusion of said cell of the composition and a nematode cell may lead to the death and or inhibition of growth of the nematode, thereby treating the nematode infection in the animal. In some embodiments, the animal is a rodent, a mammal, an avian, and the like. In some exemplary embodiments, the animal is cattle, chicken, horse, canine, and the like, or any other animal that may be infected by nematode.

According to some embodiments, there is further provided a viral vector for the expression of a nematode fusogenic protein on the surface of a virus. The fusogenic protein may be selected from AFF-1, EFF-1 and homologs thereof.

According to further embodiments, there is provided a cell expressing an exogenous fusogenic protein of nematode origin, wherein said exogenous fusogenic protein is a Fusion Family protein member. The cell may be of any origin, such as, for example mammalian cell, avian cell, viral cell, plant cell, human cell, animal cell, and the like. In some embodiments, the cell is a non-insect cell. Each possibility is a separate embodiment.

In various embodiments, there are further provided kits for practicing antinematodal methods of various embodiments. The kits may include, for example, at least one or more of a virus expressing an exogenous nematode fusogenic protein; a cell expressing an exogenous nematode fusion protein, wherein the cell may optionally express an antinematodal agent; a vector for expressing a nematode fusogenic protein on the surface of a cell; and a viral vector expressing a nematode fusogenic protein. The kits may further include additional components, such as, for example, suitable containers, suitable growth medium, buffers, reagents, and the like. Additionally, the kit may further include instructions for using the components of the kit for practicing various embodiments, such as, for example, for the treatment of nematode infection.

According to various embodiments, it is to be emphasized that wherein said fusogenic protein of nematode origin, it also encompasses homologs thereof. In some embodiments, the fusogenic protein comprises any protein having at list 15% identity or similarity with a known FF or protein of related structure (as demonstrated, for, example, in FIG. 6).

The term comprising includes the term consisting of.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Materials and Methods

DNA Constructs

For transient expression of FF proteins, AFF-1::FLAG (SEQ ID NO:1), EFF-1::V5 (SEQ ID NO: 2), Tsp-FF-1::FLAG (SEQ ID NO: 3), and Bfl-FF-1::FLAG (SEQ ID NO: 4) were inserted into the pCAGGS mammalian expression vector (15) (Tables 2 and 4). Unless otherwise indicated, 5' KpnI and 3' NheI restrictions sites were used to clone into pCAGGS. To generate pOA20 (Table 2) the DNA encoded by pIZT-AFF-1 (10) was PCR amplified using primers OR55, OR56 (Table 3). To generate pOA19 (Table 2) the DNA encoded by pIZT-EFF-1A (9) was PCR amplified using primers OR54, OR55 (Table 3). To generate pOA35 (Table 2), DNA from a cDNA library (obtained from Nagano) was PCR amplified using nested primers OR100-OR103 (Table 3). The PCR product was ligated into pGEMT-easy as recommended by manufacturer (Promega) and then used as template for PCR amplification with primers OR111 and OR112 (Table 3). To generate pOA60 (Table 2), the cDNA sequence corresponding to accession gi|210090015| with Flanking 5' KpnI 3' NheI was optimized for expression and synthesized (GeneScript). To label cytoplasm, pRFPnes (16) was used. To label the nucleus, pCFPnls (SEQ ID NO. 21) encoding CFP with two tandem repeats of the nuclear localization signal (nls) from simian virus large T-antigen was used. To generate pCFPnls, primers OR147-148 (Table 3) were used with pCH44 (16) as template. The PCR product was cloned into the BamHI, EcoRI sites of pcDNA3.1 (+) (Invitrogen). To generate pOA6 P. pacificus genomic DNA (PS312) was used as template with primers OR-19 and OR-22 (Table 3). The PCR product was ligated into pPD49.78. To generate pRSETA-AFF1EC (SEQ. ID. NO: 27), primers AM66 and AM 67 (Table 3) were used with Ce-AFF-1 cDNA as template (10). The PCR product was cloned into the BglII, KpnI sites of pRSET-A (Invitrogen). All sequences were verified by sequencing.

TABLE 2

Plasmids used

| Plasmid Name | Description |
|---|---|
| pOA6 | *P. pacificus* eff-1 genomic sequence (SEQ ID NO: 20) in pPD49.78 (hsp 16.2) |
| pOA19 | *C. elegans* eff-1 fused to a C-terminal V5 tag (EFF-1::V5) (SEQ ID NO 2) in pCAGGS vector. (V5 tag nt. 1974-2049) |
| pOA20 | *C. elegans* aff-1 fused to a C-terminal FLAG tag (AFF-1::FLAG) (SEQ ID NO: 1) in pCAGGS vector |
| pOA35 | *T. spiralis* ff-1 with a kozak sequence fused to a C-terminal FLAG tag (Tsp-FF-1::FLAG) (SEQ ID NO: 3) in pCAGGS vector (FLAG-tag nt. 1779-1803 of SEQ ID NO: 3). |
| pOA60 | *B. floridae* ff-1 with a kozak sequence fused to a C-terminal FLAG tag (Bfl-FF-1::FLAG) (SEQ ID NO: 4) in pCAGGS vector (FLAG tag: nt. 1740-1764 of SEQ ID NO: 4) |
| pCFPnls | CFP with two tandem nuclear localization signals (SEQ ID NO: 21) |
| pCAGGS | A chicken beta-actin/rabbit beta-globin hybrid promoter with a human *cytomegalovirus* immediate early promoter (CMV-IE) enhancer |
| pCAGGS-Gind | VSV G Indiana strain (ref. 20) |
| pRFPnes | DsRed2 with a nuclear export signal (pCH19) (Ref. 16) |
| pRSETA-AFF1EC including 6His tags | The extracellular domain of Ce-AFF-1 including 6-His tag (SEQ ID NO: 27). (6XHis tags, nt. 1692-1710 of SEQ ID NO: 27). |

TABLE 3

Primers used

| Name | Sequence |
|---|---|
| OR-19 (SEQ ID NO: 5) | ATGATCTTCTCTTCTCTTCTACTGTATAC |
| OR-22 (SEQ ID NO: 6) | TCATACATAATCTCCAGGTAGAACATC |
| OR-54 (SEQ ID NO: 7) | TTAATTGGTACCACTATGGAACCGCCGTTTGAGTGG |
| OR-55 (SEQ ID NO: 8) | AATTAAGCTAGCTCAACCGGTACGCGTAGAATCGAGACC |
| OR-56 (SEQ ID NO: 9) | TTAATTGGTACCACTATGGTACTGTGGCAATGGTCAATAGCC |
| OR-100 (SEQ ID NO: 10) | ATGTTCTCACCACTTTTTTGTCTTCTTCTTCTGC |
| OR-101 (SEQ ID NO: 11) | AACTGCCTCGCCCAAGAATATGCC |
| OR-102 (SEQ ID NO: 12) | ATATTCTTGGGCGAGGCAGTTGACC |
| OR-103 (SEQ ID NO: 13) | TCACAATTTGTTAGCATTCGTTCTGCC |
| OR-111 (SEQ ID NO: 14) | TTAATTGGTACCATGTTCTCACCACTTTTTTGTCTTCTTCTTCTGC |
| OR-112 (SEQ ID NO: 15) | AATTAAGCTAGCTCATTTGTCATCGTCGTCCTTGTAGTCCAATTTGTTAGCATTCGTTCTGCCATTTCC |
| OR-147F (SEQ ID NO: 16) | AATTAAGGATCCATGGTGAGCAAGGGCGAGGAGCTG |
| OR-148R (SEQ ID NO: 17) | AATTAAGAATTCTTATACCTTTCTCTTCTTTTTTGGATCTACC |
| AM-66 (SEQ ID NO: 18) | TATGTCTTAGATCTCCAAAGTCTCATCAGTACACAGTACT |
| AM-67 (SEQ ID NO: 19) | TGTATCATGGTACCCTCTGTGAAATCCCCACCATGAGC |

Nematode Strains

Nematode strains were maintained according to standard protocols. In addition to the wild-type strain N2, the following strains were used LGII: BP347 eff-1 (ok1021) (9). LGIV: SU93 jcIs1[ajm-1::gfp, pRF4] (7), BP421 eff-1 (ok1021)II; hyEx161[ajm-1::gfp, (21) pOA6 (Ce-hsp::Ppa-ff-1) (SEQ ID NO 20). To drive Ppa-ff-1 ectopic expression in *C. elegans*, 10 ng/µl of pOA6 (Table 2) were co-injected with 10 ng/µl of the apical junction marker AJM-1: GFP (hyEx161).

Bioinformatics

Identification and Characterization of New Members of the FF Family

FF proteins in nematodes were identified as described in Reference 4. For the Chordate, Ctenophore and Arthropod sequences, the BLAST search provided by the National Center for Biotechnology Information (NCBI) was used. For annotation, the Augustus gene prediction software with the training set for *C. elegans* was used. In some cases, the gene model was manually corrected based on the multiple sequence alignment (for example, as shown in FIG. 6B). Accession numbers and databases are summarized in Table 4, hereinbelow.

Phylogeny of FF proteins (FIG. 4A)

Phylogenetic analyses were conducted in MEGA4. The evolutionary history was inferred using the Maximum Parsimony (MP) method. The MP tree was obtained using the Close-Neighbor-Interchange algorithm with search level 3 in which the initial trees were obtained with the random addition of sequences (10 replicates). All positions containing gaps and missing data were eliminated from the dataset (Complete Deletion option). The signal sequence was removed from the final dataset. Evolutionary relationships of 14 (right) and 25 (left) taxa is shown (FIG. 4A). For 14 taxa, the full length sequence of the extracellular domain was used Tree #1 out of 3 most parsimonious trees (length=1165) is shown. The consistency index is (0.926554), the retention index is (0.930667), and the composite index is 0.868356 (0.862313) for all sites and parsimony-informative sites (in parentheses). There were a total of 438 positions in the final dataset, out of which 344 were parsimony informative. For 25 taxa the amino acid sequences corresponding to the TGFβ-RI like domains (10) AFF-1 (84-192) (Residues 84-192 of SEQ ID NO: 23 were used; the sequence of the *N. gruberi* served as an outgroup. Tree #1 out of 9 most parsimonious trees (length=469) is shown. The consistency index is (0.727876), the retention index is (0.717241), and the composite index is 0.529138 (0.522063) for all sites and parsimony-informative sites (in parentheses). There were a total of 75 positions in the final dataset, out of which 60 were parsimony informative.

Secondary Structure Prediction (FIG. 6C)

Predictions were performed using the JNET method available from the web services of the Jalview 2.5 software.

Structural Homology (FIGS. 8A-B)

The multiple sequence alignment was used as query to scan the protein data bank (PDB) for homologues by sequence-structure comparison either using FUGUE v2.s.07 or HHpred. Searches identified several putative distant homologues belonging to the Class II family of viral fusogens (14). The most probable homology was to Dengue2 envelope glycoprotein (loke, lok8, (accession: GI: 34811077/8)) (FUGUE confidence 95% and HHpred probability 61%). In addition, Tick-Born Encephalitis envelope glycoprotein (lsvb), Semliki Forest Virus (lala), and Dengue 1 and 3 were identified with lower probabilities (lp58, luzg).

Cells and Reagents

All Baby Hamster Kidney cells (BHK) are BHK-21 (ATCC). BHK cells and their growth conditions were according to standard protocols. Dulbecco's modified Eagle's medium (DMEM), Penn/Strep, L-glutamine, and sodium pyruvate obtained from Gibco. Fetal Bovine Serum was obtained from Biological Industries, Kibbutz Beit Haemek, Israel. Experiments with Sf9 cells and their growth conditions were as described (9,10).

Cell-Cell Fusion Assay

BHK cells at ~70% confluence were transfected using Fugene6 (Roche) with 2 μg of pCAGGS DNA (including an insert (FF coding sequence as detailed above) or an empty vector) and 0.5 μg of pRFPnes DNA in 35 mm tissue culture dishes (Corning) containing a glass cover slip on the bottom (Knittel). At 14-24 hours post transfection the cells were fixed with 4% paraformaldehyde in PBS and processed for immunofluorescence. To assay multinucleated cells, cell nuclei was stained with Hoechst (1 μg/ml, H3570, Molecular Probes) or 1 μg/ml DAPI for 10 min at room temperature (9). The number of nuclei in expressing cells as marked by pRFPnes or antibody staining (see below), was counted using either a Zeiss Axiovert 200M inverted or a Nikon Eclipse E800 upright fluorescence microscope. The fusion indexes (shown as percentage of fusion) were defined as the ratio between the number of nuclei in multinucleated cells and the total number of nuclei in fused cells and expressing cells that were in contact but did not fuse. The fusion indexes are presented as means±standard errors of at least eight independent experiments. Each experiment consisted of at least two replicates of the same transfection (2, 3). Transfection efficiency was evaluated as 40-60% based on pRFPnes and antibody staining.

Color Mixing Assay

Cytoplasmic content mixing assays were performed as described (16) with some modifications. The cytoplasm of cells that express AFF-1 was marked with a red fluorescent protein by expressing RFPnes. The nuclei of cells that express EFF-1 were marked with a CFPnls. Fused hybrid cells could be distinguished by their red cytoplasm surrounding multiple blue nuclei. The percentages of fused hybrid cells (red and cyan; purple) and multinucleated cells (red or cyan alone) were calculated by dividing the mean number of red, cyan and purple cells by the mean number of cells from four independent experiments. Experiments were repeated at least five times yielding similar results independent of whether the co-transfection fluorescent marker was RFPnes or CFPnls.

Pseudoviruses Preparation

Recombinant viruses were recovered as described (17) with some modifications. BHK cells were grown to 70% confluence on 10 cm plates and then transfected with plasmids encoding pCAGGS empty vector, pOA19 or pOA20 (Table 3). Following 24 hour incubation at 37° C. in 5% $CO_2$, cells were infected with VSVG-complemented VSVΔG recombinant virus (VSVΔG-G) at a multiplicity of infection (MOI) of 2-5 for 1 hour at 37° C. in a 5% $CO_2$ incubator in serum free culture medium (DMEM). Virus infected cells were washed at least 3 times with serum-free DMEM or PBS to remove unabsorbed VSVΔG-G virus. Following a 24 hour incubation period at 37° C. the supernatant Wand cells containing the VSVΔG, VSVΔG-EFF-1, or VSVΔG-AFF-1 pseudoviruses were harvested and centrifuged at 600 g for 10 min at 4° C. to clear cell debris. Virions were removed from the supernatant by pelleting at 100,000 g through a 20% sucrose cushion and resuspended in 10% sucrose in Hepes/NaCl buffer (25 mM Hepes, 130 mM NaCl pH 7.4).

Titering VSV Pseudotype Viruses on BHK Cells

To determine the titer of each pseudovirus preparation, $3 \times 10^4$ BHK cells were plated into each well of a 96 well tissue culture plate (NUNC). For titering of VSVΔG-AFF-1 or VSVΔG-EFF-1, BHK cells were initially transfected with 1 μg/ml aff-1 or eff-1, pOA20 or pOA19, respectively. Cells transfected with empty vector served as control. Six serial dilutions of the virus were performed and added to cells. After 18-24 hours of incubation, GFP expressing cells were counted in at least two dilutions using a Zeiss Axiovert 200M fluorescence microscope. Each experiment was repeated at least three times with duplicates. Inoculation was performed in the presence of anti-VSVG antibody mAb I1 diluted 1:100 to inhibit infection due to residual, presence of VSVG. Results were also confirmed by FACS analysis. For FACS analysis BHK cells were grown to 70% confluence and transfected with 1 μg/ml of plasmid encoding aff-1 or eff-1 (plasmids pOA20 or pOA19, respectively). Following 24 hour incubation, cells were infected with VSVΔG-AFF-1 and incubated for 24 hours. To measure the titer cells were collected using EDTA and fixed in 4% paraformaldehyde. Samples were maintained on ice and examined for GFP expression using BD FACS Calibur (N=20,000 cells, FIG. 5).

Immunoblotting

Figure 1A:
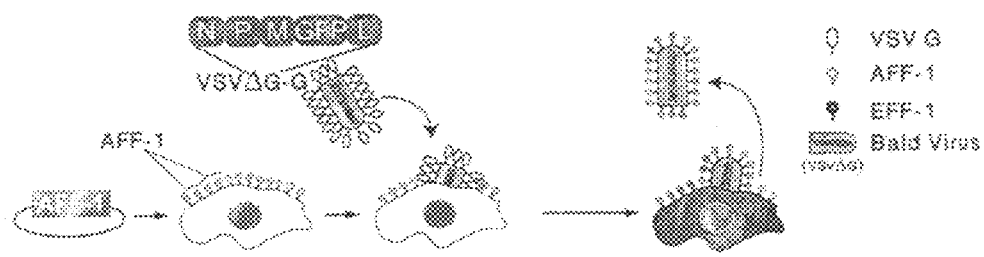
FIG. 1A shows a schematic illustration of the generation of recombinant single round infective VSVΔG-AFF-1 in vitro. BHK cells were transfected with a plasmid encoding aff-1 (Table 2, below) and expressed the protein on the cell surface. Cells were then infected with the G-complemented VSVΔG recombinant virus (VSVΔG-G). The viral genome encodes GFP in place of the fusogenic glycoprotein G. Infection results in viral induced expression of GFP by target cells (gray cytoplasm). VSVΔG-AFF-1 pseudoviruses were harvested from the supernatant.
Figure 1B:
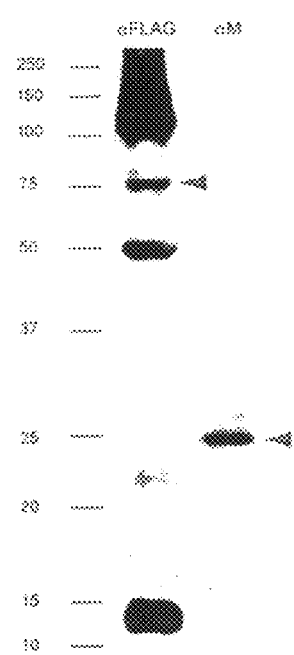
FIG. 1B shows a pictograph of Western Blot analysis of purified. VSVΔG-AFF-1 pseudoviruses demonstrating incorporation of AFF-1 into pseudotypes. Left Panel (A) depicts Mouse anti-Flag antibody recognizing bands of an apparent molecular weight (MW) of 75 kDa. The apparent MW of AFF-1 in Sf9 insect cells is 75 kDa (3). The theoretical MW of AFF-1 is 67 kDa (8). The extra bands reflect oligomers, processing and differential glycosylation of AFF-1 in BHK cells. Right panel (B) depicts Mouse anti-VSV M antibody, which identified a protein of an apparent molecular weight of 25 kDa corresponding to the predicted molecular weight of VSV-M (arrow head).

To detect proteins by Western blotting, samples were treated with SDS-PAGE sample buffer containing 10% of β-mercaptoethanol or RIPA buffer (50 mM Tris, 150 mM NaCl, 1% NP40, 5% Deoxycholate) for 20 min at 4° C. Samples were boiled in the presence of 20 mM DTT for 5 min and the protein profile was examined on an 8%, 10% or 12% SDS polyacrylamide gel. For AFF-1 expressing cells (BHK-AFF-1) and viruses (VSVΔG-AFF-1) bands were visualized using mouse anti-FLAG (M2, Sigma F3165) monoclonal antibody and mouse anti-M polyclonal antibody (FIG. 1B). For EFF-1 expressing cells (BHK-EFF-1) and viruses (VSVΔG-EFF-1) bands were visualized using mouse anti-V5 (Cat #46-0705 Invitrogen). In controls, rabbit anti-VSVG (Cat #V4888 Sigma-Aldrich) was used. As secondary antibodies goat anti-mouse antibodies conjugated with HRP (Cat #115-035-003 Jackson), were used. Bands were detected by chemoluminescence (EZ-ECL kit, Biological Industries, Kibbutz Beit Haemek, Israel) using a FUJI LAS 3000 with the Image Gauge V3.12 software package. Data shown are representative of at least three independent experiments.

Production of Mouse Anti-AFF-1 Polyclonal Antibodies

The extracellular domain of AFF-1 (AFF-1EC) was subcloned into pRSET-A that introduced 6×His at the N terminus (Table 2). The AFF-1EC::6×His (SEQ ID NO: 27) fusogenic protein was over-expressed in *E. coli* by adding 0.5 mM IPTG and incubating the culture overnight at 16° C. Rosetta and affinity purification with NiNTA beads (Qiagen Cat#30210) was according to the QIAexpressionist manual (06/2003, QIAGEN). The protein was eluted by adding four 0.5 ml aliquots of elution buffer A (8M urea, 100 mM $NaH_2PO_4$, 10 mM Tris-HCl, pH 5.9) followed by another four aliquots of elution buffer B (8M urea, 100 mM $NaH_2PO_4$, 10 mM Tris-HCl, pH 4.5). Mouse polyclonal antibodies were prepared using AFF-1EC as antigen (Adar Biotech Inc., Israel).

Immunofluorescence

BHK-21 cells were grown on tissue culture plates with glass cover slips on the bottom (Knittel). Cells were fixed with 4% paraformaldehyde in PBS, incubated in 40 mM $NH_4Cl$ to block free aldehydes, washed in PBS, permeabilized in 0.1% triton X-100 in PBS and blocked in 1% FBS in PBS. The cover slips were incubated 1 hour at 23° C. with either anti-V5 1:500 (Invitrogen) or anti-FLAG 1:2000 (Sigma) mouse monoclonal antibodies. The secondary antibodies were goat anti-mouse and goat anti-rabbit coupled to Alexa488, 633 or 643 (Molecular Probes/Invitrogen). Transfected cells expressed cytoplasmic RFP from the pRFPnes vector and nuclei were visualized with DAPI or Hoechst staining as described above.

Sere obtained from mice immunized with AFF-1EC were tested by immunofluorescence using Sf9 cells expressing AFF-1::Flag. Sera #8 diluted 1:500 showed membrane and intracellular vesicular staining (FIG. 2N, Panel A). Pre-immune sera (FIG. 2N, Panel B) or secondary antibodies alone (Alexa Fluor 568 goat anti-mouse IgG (H+L) 1:500) gave no staining.

Transmission Electron Microscopy (TEM)

Negative Staining-TEM

A 400-mesh carbon-coated grid was placed on a 20 µl sample drop for 2 min and blotted with a filter paper. The sample was chemically stained by placing the grid on a 20 µl drop of 2% uranyl acetate for 2 min followed by blotting with a filter paper and air-drying. Specimens were examined in a Tecnai T12 $G^2$ TEM (FEI) or in a Philips CM120 transmission electron microscopes operated at 120 kV. Images were recorded digitally on a Gatan UltraScan 1000 2k×2k camera or the Gatan 791 wide-angle camera using the DigitalMicrograph software (Gatan, U.K.)

Cryo Electron Microscopy

A 3-µl drop of the sample was placed on a glow-discharged holey carbon coated copper electron microscopy grid (C-flat, Protochips). The drop was blotted, and the sample was vitrified by plunging into liquid ethane (−183° C.). The specimen was then transferred to liquid nitrogen (−196° C.) for storage. Vitrified specimens were examined on a Tecnai F30 Polara TEM (FEI) operated at 300 kV and equipped with a GIF2002 postcolumn energy filter (Gatan) operated in zero loss mode. 2K×2K images were acquired at a calibrated magnification of 27,500×, resulting in a pixel size of 0.5 nm at the specimen level. Projection images were recorded at defocus settings between −4 µm to −6 µm using SerialEM. Alternatively, specimens were examined in a Tecnai T12 $G^2$ TEM (FEI) operated at 120 kV and images were recorded digitally on a Gatan UltraScan 1000 2K×2K camera using the DigitalMicrograph software (Gatan, U.K.).

Cryo Electron Tomography

A 4-µl aliquot of the pseudotyped virus preparations was pipetted onto a glow-discharged holey carbon coated copper electron microscopy grid (Cflat, Protochips). Colloidal 10 nm diameter gold particles coupled to bovine serum albumin (BSA) were added, excess liquid was absorbed using a filter paper and the grids were vitrified by plunge-freezing in liquid ethane. Vitrified grids were stored in liquid, nitrogen until examined on a Tecnai Polara TEM (FEI) operated at 300 kV and equipped with a GIF2002 or Tridem postcolumn energy filter (Gatan) operated in zero loss mode. 2K×2K images were acquired at a calibrated magnification of 27,500×, resulting in a pixel size of 0.5 nm at the specimen level. Tilt series were collected at a defocus of either −6 µm for the viral tomogram or −8 µm for the vesicle tomogram in two-degree increments covering an angular range from −60° to 60° using SerialEM. The total electron dose was kept below 100 electrons/$Å^2$. Tilt series were aligned using gold beads as fiducials. Three dimensional reconstructions were calculated from the tilt series in IMOD using weighted back projection. Slices for figures were prepared using Amira 5.2 (Visage Imaging).

Measurements

The width and length of the particles on the surface of viruses and vesicles were measured from images of negatively stained samples using ImageJ Software 1.410. The G glycoprotein was measured as control and the obtained size was compared to published dimensions. Unpaired t tests were performed ($P<0.0001$).

Immunogold Labeling

Virus samples were pipetted onto carbon-coated grids and incubated for 5 min and then blocked with 1% BSA in PBS for 30 min at room temperature. The grids were then placed on a 50 µl drop of anti-AFF-1 (#8 serum; see Immunofluorescence section above) diluted 1:100 in PBS containing 1% BSA and incubated overnight at 4° C. in a sealed humidified chamber. Excess antibody was removed by placing grids sequentially onto three 50 µl drops of 0.1% BSA in PBS for 2 min each time. The grids were then placed on a 20 µl drop of goat anti-mouse IgG conjugated with 12-nm gold particles (Jackson lab, 1:20) for 1 hour at room temperature. Unbound gold conjugates were removed by three sequential 2-min washes with PBS. Samples were fixed by placing the grids on a 50 µl drop of 0.1% glutaraldehyde in PBS for 5 min. The grids were washed twice in PBS for 2 min and were then negatively stained by incubating the grids for 2 min on a 20 µl drop of 2% phosphotungstic acid in water (pH 7). Excess stain was removed and the grids were air-dried. Images were recorded digitally as described above.

Example 1

CeFF Proteins are Capable of Mediating Virus-Cell Fusion

Figure 1C:
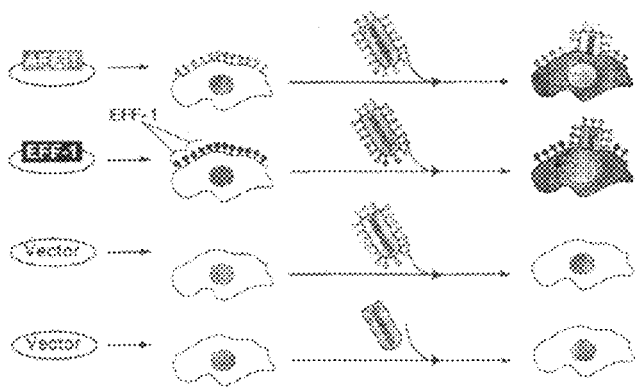
FIG. 1C shows a schematic illustration summarizing VSVΔG-AFF-1 infection of BHK cells. Cells were transfected with aff-1, eff-1 or vector plasmid and infected with VSVΔG-AFF-1. Cells transfected with empty vector and infected with bald particles served as negative controls.
Figure 1D:
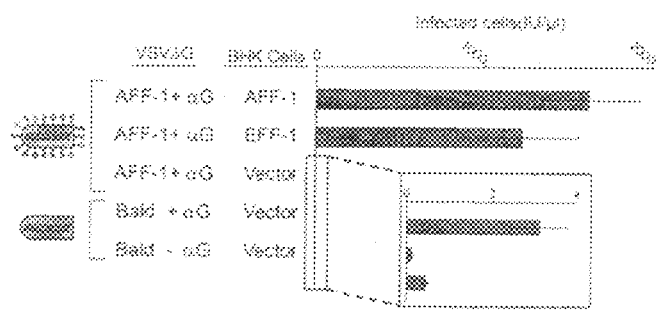
FIG. 1D shows bar graphs representing titers of VSVΔG pseudoviruses. The type of protein on the viral membrane (Bald or AFF-1) and on the BHK cell membrane (Vector, AFF-1 or EFF-1) is indicated. Anti-VSVG antibody (ΔG) was used to neutralize any, residual VSVΔG-G virus (shown in FIG. 1F, below). Titers are in infectious units (IU) representing the number of cells expressing. GFP per microliter 24 hours after virus inoculation. Data are mean+/−SE (n=3 experiments). The inset shows background infection.
Figure 1E:
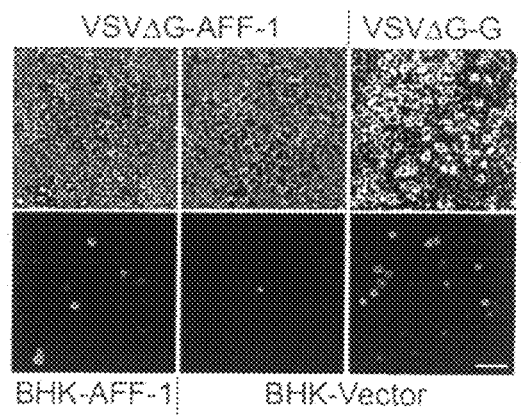
FIG. 1E shows images of infected BHK cells. Infection of BHK cells monitored as GFP expression; phase contrast (top panels) versus fluorescence (bottom panels). Scale bar is 50 μm.
Figure 1F:
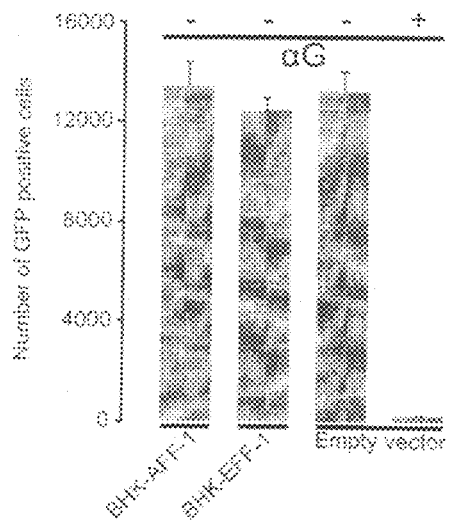
FIG. 1F shows a bar graph showing VSVΔG-G infection of cells expressing CeFFs and in the presence of anti-VSVG. Cells expressing AFF-1, EFF-1 or transfected with empty vector were infected with VSVΔG-G pseudo typed virus ($1.5 \times 10^7$ IU). Infection was preformed in the presence (+) or absence (−) of anti G antibodies (αG) (1:100). Cells were examined by FACS (total number of cells counted 20,000 cells) after 24 hours. Transfection/Expression of FF proteins did not affect infection efficiency of VSVΔG-G pseudo typed virus (The two-tailed P value equals 0.49-0.89). αG efficiently blocked infection of VSVΔG-G. Results are presented as mean of three independent experiments+/− standard error.

In order to test whether CeFF proteins are capable of mediating virus-cell fusion when presented on the membrane of Vesicular Stomatitis Virus (VSV), AFF-1 complemented VSVΔG pseudoviruses, in which the gene encoding the fusogenic glycoprotein (VSVG) was replaced by GFP (VSVΔG-AFF-1; scheme of FIG. 1A) were generated. Infection of Baby Hamster Kidney cells (BHK) expressing AFF-1 (BHK-AFF-1) on their surface with VSVΔG-AFF-1 showed a 600-fold increase in infection compared to control BHK cells (FIG. 1C to 1E). These results demonstrate that AFF-1 can replace the endogenous viral fusogen as the minimal fusogenic machinery that can mediate virus-cell binding and fusion. To explore whether EFF-1 and AFF-1 can heterotypically interact with each other, VSVΔG-AFF-1 was added to BHK expressing EFF-1 (BHK-EFF-1, Scheme of FIG. 1C) and vice versa. It was found that VSVΔG-AFF-1 was able to infect BHK-EFF-1 cells and that the efficiency of AFF-1-AFF-1 and AFF-1-EFF-1 mediated virus-cell fusion was not significantly different (FIG. 1D). Although infection due to residual VSVG complemented VSVΔG (VSVΔG-G) was negligible (FIG. 1D), inoculations in the presence of neutralizing anti-G antibody mAb I1 were performed to assure that only AFF-1-mediated infection was measured (FIG. 1F). The results further demonstrate that AFF-1 and EFF-1 can mediate homotypic virus-cell fusion without additional membrane co-factors and AFF 1-EFF-1 mediated fusion also resulted in infection.

Example 2

Structure-Function of AFF-1

To study the relationship between structure and function of AFF-1, transmission electron microscopy (TEM) was used. Negatively stained samples of VSVΔG to VSVG and AFF-1 complemented VSVΔG preparations were compared. VSVΔG virions have the typical VSV 'bullet' shape with a smooth membrane, hence termed bald, while both VSVΔG-G and VSVΔG-AFF-1 virions displayed distinct spikes on their envelopes (FIG. 2A to C). In negative stain (pH 5), VSVG form elongated spikes on VSVΔG-G (FIG. 2B), while VSVΔG-AFF-1 show bulkier spikes (FIG. 2C). The estimated average spike length of VSVG and AFF-1 as measured from the negative stain images were 145 Å and 110 Å respectively (Table 1). To confirm that the observed spikes were indeed AFF-1, immunogold labeling using anti-AFF-1 polyclonal antibodies was performed. A specific immunoreactivity on the surface of VSVΔG-AFF-1 is observed (FIGS. 2D, 2E, 2N and 2O). To further characterize the pseudoviruses at higher resolution and in a more native state they were imaged embedded in vitreous ice by cryo electron microscopy (cryoEM, FIG. 2F to H) and cryo electron tomography (cryoET, FIG. 2I to K). CryoEM projection images show that AFF-1 proteins uniformly coat the pseudoviruses. Individual spikes could be observed at central sections of the tomograms (FIG. 2J, inset). Higher order assemblies of AFF-1 in the form of penta- or hexamerit "flower" shaped complexes could be observed in computational slices through the tomogram oriented peripheral to the pseudotyped virus particles (FIG. 2I, inset). These assemblies were even better visible in slices through the tomograms of co-purified vesicles (FIGS. 2L, 2M and 2P). The order of these arrays may have a critical function in bending and deforming plasma membranes to mediate fusion.

TABLE 1

Measured size of AFF-1 and VSVG

| | VSVG | | AFF-1 | |
|---|---|---|---|---|
| | Length (nm) | Width (nm) | Length (nm) | Width (nm) |
| Mean Size | 14.5 | 8.7 | 10.9 | 6.0 |
| SEM | 0.5 | 0.4 | 0.5 | 0.3 |

TABLE 1-continued

Measured size of AFF-1 and VSVG

| | VSVG | | AFF-1 | |
|---|---|---|---|---|
| | Length (nm) | Width (nm) | Length (nm) | Width (nm) |
| N | 20 | | 32 | |
| Size (38) | 12.5 | 6.0 | | |

*SEM—Standard Error, N—number of measurements

Example 3

FF Proteins can Interact

To show that FF proteins can interact, cytoplasmic mixing between cells using a color mixing-assay (FIG. 3 A to C) was performed. aff-1 was coexpressed with a fluorescent protein (red) that contained a nuclear export signal (RFPnes; FIG. 3A) and the cells were mixed with cells co-expressing eff-1 and a fluorescent protein (cyan) that contained a nuclear localization signal (CFPnls; FIG. 3B). The two cell populations were co-cultured and multinucleated cells were observed, mostly dikaryons, expressing both markers (FIGS. 3 C, E to H and O). In contrast, no cells expressing both markers following mixing of cells transfected with empty vector (FIGS. 3 D and L) were observed. AFF-1-mediated mixing (FIG. 3I to K) occurred only when the protein was expressed in both cells (FIGS. 3 M and N); thus, cytoplasmic mixing during cell-cell fusion is dependent on the expression of AFF-1 in both fusing partners.

Example 4

Divergent FFs can Function as Fusogens

To determine whether divergent FFs can function as fusogens, Tsp-ff-1 was expressed in BHK cells and its activity was compared to AFF-1 (FIGS. 4 B and D). Using immunofluorescence 28±4% multinucleation was observed in cells transfected with Tsp-ff-1 compared to 26±2% and 4±3% multinucleation in cells that were transfected with aff-1 and empty vector, respectively (FIG. 4F). In addition, EFF-1 paralog from the nematode *Pristionchus pacificus* was expressed in *C. elegans* embryos to result in ectopic fusion of embryonic cells (FIG. 7). Additionally, expression of the FF ortholog identified in the chordate *B. floridae* (Bfl-ff-1), (FIGS. 6A and 6B and Table 4), in BHK cells resulted in 37±7% multinucleation (FIGS. 4 E and F).

Example 5

Identification and Characterization of New Members of the FF Family

FF proteins in nematodes were identified as described in (4). For the Chordate, Ctenophore and Arthropod sequences the BLAST search provided by the National Center for Biotechnology Information (NCBI) was used. For annotation, the Augustus gene prediction software with the training set for *C. elegans* was used. In some cases, the gene model was manually corrected based on the multiple sequence alignment (FIG. 6B). Accession numbers and databases are summarized in Table 4, hereinbelow.

TABLE 4

| Species | Sequence Identifier/Accession number |
|---|---|
| *Caenorhabditis elegans* | CeAFF-1 (SEQ ID NO: 23) (WP: CE41369)<br>CeEFF-1 (SEQ ID NO: 24) (WP: CE03028, WP: CE30881, WP: CE31159, WP: CE32594)<br>C26D10.7 (CeEFF-2) (WP: CE36985) |
| *Caenorhabditis briggsae* | Cbr-aff-1 (CBP17138)<br>Cbr-eff-1 (BP: CBP34546, BP: CBP37650) |
| *Caenorhabditis japonica* | CJA05978 (CJA05978/JA11265)<br>CJA03218 (CJA03218/JA03456) |
| *Caenorhabditis ramanei* | Cre-aff-1 (RP: RP19336)<br>Cre-eff-1 (RP: RP32670, RP: RP36929) |
| *Caenorhabditis brenneri* | Database: Caenorhabditis_ (CBN32067, CN35418, Database: Caenorhabditis_PB2801-4.0-contigs [Contig1645.2])<br>CBN17896 (CBN17896, CN30500, CN18501) |
| *Caenorhabditis sp5, 7, 9, 11* | Cs5-AFF-1(Database: Caeno_sp5_DRD-2008_JU800_2.fna, contig2451)<br>Cs5-EFF-1(Database: Caeno_sp5_DRD-2008_JU800_2.fna, contig6234)<br>Database: Caeno_sp5_DRD-2008_JU800_1.fna [contig_262626]<br>Database: Caeno_sp7_ju1286_454scaffolds_1.fna [scaffold00005]<br>Database: Caeno_sp9_ju1422_454scaffolds_1.fna [scaffold00235, scaffold00002]<br>Cs7/9-AFF-1 (Database: Caeno_sp7_ju1286_454scaffolds_1.fna scaffold00007; Database: Caeno_sp9_ju1422_454scaffolds_1.fna scaffold00001, scaffold00169)<br>Cs7/9-EFF-1 (Database: Caeno_sp7_ju1286_454scaffolds_1.fna scaffold00005; Database: Caeno_sp9_ju1422_454scaffolds_1.fna scaffold00002)<br>Cs7/9-EFF-1(Database: Caeno_sp9_ju1422_454scaffolds_1.fna scaffold00235)<br>Cs7/9-EFF-1(Database: Caeno_sp9_ju1422_454scaffolds_1.fna scaffold00235)<br>Cs11-FF (gi|319532004|gb|AEKS01003493.1|, Contig629.1546)<br>Database: Caeno_sp11_JU1373_454scaffolds_1.fna [scaffold01488] |
| *Pristionchus pacificus* | Ppa-FF-1 (Database: PpaFreeze1.bases Contig235.2)<br>Ppa-FF-2 (Database: PpaFreeze1.bases Contig162.2)<br>Ppa- FF-3 (Database: PpaFreeze1.bases Contig735.1 + Contig735.2) |
| *Pristionchus entomophagus* | Pen-FF-1 (Database: Pristionchus_entomophagus-3.0.bases Contig1225.3) |
| *Pristionchus maupasi* | Pma-FF-1 (Database: p. maup genome Contig3990.1) |
| *Trichinella spiralis* | gi|162730680 (Tsp-ff-1) (gi|339236477|ref|XP_003379793.1|)<br>gi|339234943|ref|XP_003379026.1|<br>gi|339234945|ref|XP_003379027.1| |
| *Trichinella pseudospiralis* | Tps-FF gi|149208398|gb|EF601568.1| (SEQ ID NO. |
| *Trichinella papuae* | Tpa-FF gi|149208399|gb|EF601569.1| |
| *Meloidogyne incognita* | Min-FF (gi|198718377|emb|CABB01003673.1| *Meloidogyne incognita*, whole genome shotgun sequence assembly, contig_3673, gi|19265127|gb|BM881383.1|BM881383 rb09d06.y1), gi|19265127| |
| *Meloidogyne arenaria* | Mar-FF (BI746953, rm34a12.y1) gi|15768755| |
| *Meloidogyne hapla* | Mha-FF (gi|207096946|gb|ABLG01001006.1| *Meloidogyne hapla* strain VW9 Mh10g200708_Contig1005, gi|207095745|gb|ABLG01002207.1| *Meloidogyne hapla* strain VW9 Mh10g200708_Contig2206) |
| *Globodera pallida* | Gpa-FF (gi|54548408|gb|CV578685.1|CV578685 kf14e11.y1)<br>Gpa-FFA (Database: gpal.201011.contigs.fasta [Sanger] Contig 1004319)<br>Gpa-FFB (Database: gpal.201011.contigs.fasta [Sanger] Contig 1004319) |
| *Ancylostoma caninum* | Aca-FF (gi|157997724|gb|EX544342.1|EX544342 AIAC-aaa88e02.g1)<br>Aca-FF (gi|158000776|gb|EX547394.1|EX547394 AIAC-aaa14c06.g1)<br>gi|157990577| |
| *Brugia Malayi* | Bma-FF-1 (gi|170576008|ref|XP_001893468.1| hypothetical protein Bm1_09975)<br>gi|170582744|ref|XP_001896266.1| hypothetical protein Bm1_24045<br>gi|170576006|ref|XP_001893467.1| hypothetical protein Bm1_09970<br>gi|154234139|gb|AAQA01001677.1| *Brugia malayi* ctg_62087<br>gi|154209490|gb|AAQA01025369.1| *Brugia malayi* ctg_35248<br>gi|154234539|gb|AAQA01001277.1| *Brugia malayi* ctg_54442<br>Bm1_09970 + Bm1_09975<br>Bm1_24045 |
| *Haemonchus contortus* | Hco-FF (gi|27320801|gb|CA869252.1|CA869252 px01a04.y1)<br>Hco-FF (Database: HAEM.contigs.fasta [Sanger] Contig 006057) |
| *Ascaris suum* | Asu-FF (gi|113050648|gb|ED245151.1|ED245151 AUAC-aag39g05.g1, gi|320312531|gb|AEUI01008540.1| *Ascaris suum* ASU_contig008540)<br>gi|320301910|gb|AEUI01019161.1| *Ascaris suum* ASU_contig019161<br>gi|320309474|gb|AEUI01011597.1| *Ascaris suum* ASU_contig011597<br>gi|320297040|gb|AEUI01024031.1| *Ascaris suum* ASU_contig024031 |
| *Oscheius tipulae* | Oti-FF (Database: Oscheius_tipulae_clc3_1.fna, contig 5292)<br>Oti-EFF-1 (Database: Oscheius_tipulae_clc3_1.fna, contig 4684)<br>Database: Oscheius_tipulae_clc3_1.fna [Contig 4684, contig 5292] |
| *Dirofilaria immitis* | Dim-FF (Database: Dirofilaria_immitis_v1.3_Maker_Transcripts.fna, DimmContig4043_DIMM48125; Database: |

TABLE 4-continued

Sequence identifiers/Accession numbers

| Species | Sequence Identifier/Accession number |
|---|---|
| | Dirofilaria_immitis_rnaseq_assembly_transabyss.v1.20110321.fna, k23_18675 1796 37333) |
| | Dim-FF (Database: Dirofilaria_immitis_rnaseq_assembly_transabyss.v1.20110321.fna, k27_51785 1538 23309, k31_119704 1392 19131) |
| | Database: Dirofilaria_immitis_clc_1.fna |
| Howardula aoronymphium | Hao-FF (Database: Howardula_aoronymphium_clc_1.fna, contig_147926) |
| | Hao-FF (Database: Howardula_aoronymphium_clc_1.fna, contig_103402) |
| | Database: Howardula_aoronymphium_clc_1.fna |
| Litomosoides sigmodontis | Lsi-FF-1 (Database: Litomosoides_sigmodontis_abyss_1.fna, 342875) |
| | Lsi-FF-2 (Database: Litomosoides_sigmodontis_abyss_1.fna, 344431, 332390) |
| | Database: Litomosoides_sigmodontis_abyss_1.fna |
| Heterodera glycines | Hgl-FF (gi\|170569983\|gb\|ABLA01000927.1\|) |
| Romanomermis culicivorax | contig05859, contig06497 (Kindly provided by W. Kelley Thomas) |
| Trichuris muris | Tmu-FF-1 (Database: T_muris_contigs.fasta [Sanger]; NODE_192365_length_12375_cov_11.496000) |
| | Tmu-FF-2 (Database: T_muris_contigs.fasta [Sanger]; NODE_99371_length_23257_cov_11.624845) |
| Strongyloids ratti | Sra-FF-1 (Database: RATTI.contigs.fasta [Sanger] Contig 75311) |
| | Sra-FF-2 (Database: RATTI.contigs.fasta [Sanger] Contig 74980) |
| | Sra-FF-3 (Database: RATTI.contigs.fasta [Sanger] Gontig 75430) |
| | Database: S.ratti.reads |
| Onchocerca volvulus | Ovo-FF (Database: O_volvulus_all454_contigs.fna [Sanger], contig25914) |
| Teladorsagia circumcincta | Tci-FF (Database: T_circumcincta_reads.fasta [Sanger] Supercontig_0000831) |
| Wuchereria bancrofti | Wba-FF (gi\|285840565\|gb\|ADBV01004176.1\| cont1.4176) GI: 285822425, GI: 285835743 |
| Loa loa | Llo-FF (gi\|285859024\|gb\|ADBU01000052.1\| contig1.52) |
| | GI: 285852521, GI: 285851695 |
| Branchiostoma floridae | Bfi-FF-1 (Database: fgenesh2_pg.scaffold_465000022; Protein ID: 104514)jgi\|Brafl1\|104514\|fgenesh2_pg.scaffold_465000022 (SEQ ID NO. 26) |
| | Bfl-FF-3 (Database: fgenesh2_pg.scaffold_46500002; Protein ID: 104513) jgi\|Brafl1\|104513\|fgenesh2_pg.scaffold_465000021 |
| Pleurobrachia pileus | Ppi-FF (gi\|167791107\|gb\|CU417832.1\|CU417832) |
| Calanus finmarchicus | Cfi-FF (gi\|190134016\|gb\|FG632618.1) |
| Lepeophtheirus salmonis | Lsa-FF (gi\|293020530\|gb\|ADND01294772.1\|) gi\|293020530\| |
| Naegleria gruberi | Ngr-FF-1 (gi\|284087402\|gb\|EFC41072.1\|) |
| | Ngr-FF-2 (gi\|284087338\|gb\|EFC41008.1\|) |
| | Ngr-FF-3 (gi\|284083966\|gb\|EFC37664.1\| NAEGRDRAFT_81886) |
| | Ngr-FF-4 (gi\|284083965\|gb\|EFC37663.1\| NAEGRDRAFT_81885) |
| | est's GI: 168534442; GI: 168542950 |
| Bursaphelenchus xylophilus | Bxy-FF-1 (gi\|351002770\|emb\|CADV01009240.1) |
| | Bxy-FF-2 (gi\|351002016\|emb\|CADV01009994.1\| |
| Caenorhabditis angaria | Can-FF (gi\|308940912\|gb\|AEHI01101512.1\|, contigRNAPATHr2484_10) |
| Heterorhabditis bacteriophora | Hba-FF-1 (gi\|343491313\|gb\|ACKM01000079.1\|, Contig56.1) |
| | Hba-FF-2 (gi\|343491313\|gb\|ACKM01000079.1\|, Contig56.1) |
| Romanomermis culicivorax | Rcu-FF |
| Heligmosomoides polygyrus | Hpo-FF (Database: Heligmosomoides_polygyrus_clc_1.fna, contig_126399) |
| | Hpo-FF (Database: Heligmosomoides_polygyrus_clc_1.fna, contig_372600) |
| | Hpo-FF (Database: Heligmosomoides_polygyrus_clc_1.fna, contig_376900) |
| Acrobeloides nanus | Ana-FF-1 |
| | Ana-FF-2 |
| Mnemiopsis leidyi | Mle-FF-1A (gi\|346671607\|gb\|AGCP01008927.1\| c605800073.Contig1) |
| | Mle-FF-1B (gi\|346671607\|gb\|AGCP01008927.1\| c605800073.Contig1) |
| | Mle-FF-2 (gi\|346671607\|gb\|AGCP01008927.1\| c605800073.Contig1) |
| | Mel-FF-3 (gi\|346680498\|gb\|AGCP01000036.1\| c600000000.Contig54) |
| | Mel-FF-4 (gi\|346673076\|gb\|AGCP01007458.1\| c605700043.Contig1) |
| | Mel-FF-5 (gi\|346661390\|gb\|AGCP01019144.1\| c601500011.Contig6) |
| | Mel-FF-6 (gi\|346674975\|gb\|AGCP01005559.1\| c606400022.Contig1) |

REFERENCES

1. W. Wickner, R. Schekman, *Nat Struct Mol Biol* 15, 658 (July, 2008). REV.
2. S. Martens, H. T. McMahon, *Nat Rev Mol Cell Biol* 9, 543 (July, 2008). REV.
3. J. M. White, S. E. Delos, M. Brecher, K. Schomberg, *Crit. Rev Biochem Mol Biol* 43, 189 (May-June, 2008). REV
4. A. Sapir, O. Avinoam, B. Podbilewicz, L. V. Chernomordik, *Dev Cell* 14, 11 (January, 2008).
5. M. Oren-Suissa, B. Podbilewicz, *Trends Cell Biol* 17, 537 (November, 2007).
6. E. H. Chen, E. Grote, W. Mohler, A. Vignery, *FEBS Lett*, (Mar. 21, 2007).
7. W. A. Mohler et al., *Dev Cell* 2, 355 (March, 2002).
8. G. Shemer et al., *Curr Biol* 14, 1587 (Sep. 7, 2004).
9. B. Podbilewicz et al., *Dev Cell* 11, 471 (2006).
10. A. Sapir et al., *Dev Cell* 12 683 (2007).
11. M. Oren-Suissa, D. H. Hall, M. Treinin, G. Shemer, B. Podbilewicz, *Science* 328, 1285 (June 4).
12. Hugot, J. P.; Baujard, P. & Morand, S. (2001): Biodiversity in helminths and nematodes as a field of study: an overview. Nematology 3: 199-208

13. Parasitology textbook Chitwood, B. G., and Chitwood, M. B. H. (1974). Introduction to Nematology (Baltimore, University Park Press).
14. M. Kielian, F. A. Rey, Nature Rev. Microbiol. 4, 67 (2006).
15. H. Niwa, K. Yamarnura, J. Miyazaki, *Gene* 108, 193 (1991).
16. C. Hu et al., *Science* 300, 1745 (2003).
17. K. Schornberg et al., *J Virol* 80, 4174 (2006).
18. Gottesman A., et. al., BioTechniques, Vol. 49, No. 4, 747-750 (2010)
19. Avinoam O. et. al., Science, 332, 589-92 (2011).
20. A. Takada et. al., Proc. Natl. Acad. Sci. USA, vol 94, pp. 14764-14769, (1997).
21. Köppen M, et. al., Nature Cell Biology Vol 3, pp. 983-991 (2001).

What we claim is:

1. A method for fusing a first mammalian cell and a second mammalian cell; comprising:
   (i) incubating a first mammalian cell expressing a nematode fusogenic protein with a second mammalian cell expressing a nematode fusogenic protein; and
   (ii) fusing the first and second mammalian cells, wherein the nematode fusogenic protein is selected from the group consisting of anchor-cell fusion failure 1 (AFF-1) and epithelial fusion failure 1 (EFF-1) and wherein the first and second mammalian cells are of the same species.

2. The method of claim 1, wherein expression of the nematode fusogenic protein is transient or stable.

* * * * *

SEQUENCE LISTING

```
<160> NUMBER OF SEQ ID NOS: 27

<210> SEQ ID NO 1
<211> LENGTH: 3584
<212> TYPE: DNA
<213> ORGANISM: Artificial Sequence
<220> FEATURE:
<223> OTHER INFORMATION: Synthetic polynucleotide

<400> SEQUENCE: 1
atgatcttct cttctcttct actgtataca atcatccttc ctcatctaat ctattcattc     60
cctcgttcat tcactcctca attcaaagta attcctcctc attgtatcaa gactccttcc    120
atcattgctc atccttccaa aggtattctc tatctttact ctcagatgtt agacagaatg    180
agatagaagg ggaataagag agacgcgtag gaagatgaag aggttcttca cactcttgtg    240
caatatcttc ggatatctca gctgatgaaa ctaactagag gatatttcac aagtgataag    300
atcaagtcta aaagaggaaa gatgtcatca atagttctcg tttctcacat tactcatctc    360
tctcattcct cattcctctc atcaactatc ctatcaatta cagtagttca aacatgggca    420
gagtaatggg aatggggtca ttcataactg attcaggaga aggatcactc aaatctctcg    480
agatgcattt ctctattgga ttgcatacaa ctgtctgttt ccgattagag gatacaaatg    540
ataattcgac tcaatccaat caatcattac ttcatacagt tactctatct agtatagaac    600
atcatcatcc agtgagtatt ctacccaatc tccccttctc tgtcttcctc tttatttttc    660
atcttctcag gtcacacaga aatacaactt cggtattcct gaagtaagtg cagattgttt    720
ctgtgaatgt gaatcaacag agagatgttc ttcttcctct tatgaattca ttaaatgtcc    780 agagggaaa gatcaggtaa ttcatttctt tctctctttc atcataatca atcaatctcg     840
actcatggtt gctatcgaac attcttcccc aatcaatcca ataaatcatg cgaaagttca    900
tctccaatgg gatcgaatct ctgttgtgaa ctcaagttca atcccttga ggtaggtcga     960 agagtatctt ccctctttct tctttcttta ctcattcact tctccgttcg aataaaaggg   1020
aggatgaatg gtcactccca ataggcgttt actcatcgtt cttcagtaat gaactcaata   1080
tactttcaga ataagacgta cactgcaatt agactgggag atccttccac attcgctatt   1140
ttcacttatg tttcctatga ttattctgga aattcatgga ttgagaggga taagaatacg   1200
attcgaattc aaatagatgg aagatctcag gaaaagtgag tcaatttcat gggaaatgga   1260
agagcttatc gggacttgga tcagtgcggt agattgtgag aaatgataag aataggaaga   1320
ttcccgcatt gagaaagagc taatttcaat ggaatgaaat ggttactgtc gatcgtattc   1380
tattcttgat tcttgcagta atcttgatag tagtggactt ctcaaattgg ttgtatctgc   1440
atggggaaga gtatcacatc aattggaaag tggaatgtat ttcactcaat caaatccagg   1500
aggagaaatg gaaggaataa gaaaggaaca aattaatgac atcaccgata ccaagtatgc   1560
ttttattgtc gttcattagc gctgattgat gtcaaatatg gctgctatta tttgtgaact   1620
tcgatgaatt ttgactaaaa attttttaatt tttgattgtt tgaatagaa ttttaattaa   1680
```

| | |
|---|---:|
| ttaattaaat taagtgttta tcaattggga tggtatcgac aagacgagaa aagtggacat | 1740 |
| ttctacgtac aaaatggagc agttattgca aagaatctgc atggggcaaa agttatcgac | 1800 |
| tgcaaggaac agagatattc atcctctctt gctgctaatt tctatgtaag aataccatct | 1860 |
| tattcaattt atttatccct tgtcttgctt tgaaaataag tactaatgag atgaattaag | 1920 |
| atgccaggtc gatttactct tcctccttac gtcgaggaac gtcatcattg gattgaaaga | 1980 |
| gcggcattct atgatggatc aatgagacaa gtcatcgtat ctcattctga aggaactaat | 2040 |
| ctatatatcg gactccatgt aagcaattcc taattcctaa atctcgaacg tcaatgattt | 2100 |
| cccttttcttt ctctctaatt tgatgaggag tgaatagctg ctgtccatta tcttcactcc | 2160 |
| tttctctcat tatctcacta gaatcatgga gagaaagata gggaaagttc ctcaccgttc | 2220 |
| tctccttctt ttcttttgtc acagggaagg atttcgaaaa tagatgactc acttatccca | 2280 |
| taagatttac aaccatcctg atagtaaatc ttttctgata tgtaatctta tggaaccagc | 2340 |
| ttttgttgaa taatcaagta cttgaaggtg tcgaaggat cagaaggaaa tgttgtcttc | 2400 |
| cttcacaatt catctcgaat tgattcattc gatggatcaa ttcttgttga ttctcattct | 2460 |
| cgtcattatc tcaatctttc actctccgaa tcgactggca aattgaatgg actcattcat | 2520 |
| gctagtgaat ccgttgcctc tcctcaggta aaatacaaat aagaataata tttaaaatca | 2580 |
| ccgtatctcg tccaaagtct atctcttctc cgttcctta gagggataaa gttggccttg | 2640 |
| tgaaatgggg acatcggctg tcaataggtg tcaatgagct actcttttta tccccttaga | 2700 |
| cactcatcaa gctctcccctt ctcttctaat tgagtcgatc acccttgagt ataaatcact | 2760 |
| taatgggggtt actctaagag ggaagtaatg aatgtgttca gattcatatg ttcacagtgt | 2820 |
| atgttcatga ggttgtgtct actaatcgat ctcttctcgt tccccttcct gctactgttg | 2880 |
| ataaaggaag gaaattagtt tgtatgagag cagaagaaga aaggaagaag attccatctg | 2940 |
| tgctgtactc ccatatcatg aagaagcact tgaggttaca caatttctaa tttgcgttgg | 3000 |
| gatttaattc aaaattaatt aatgtatgaa gaataagaag ggacacacac gaatgatgtt | 3060 |
| cacattatga taaattgata atttagattg acgtggagaa taattcgtgg agggaattaa | 3120 |
| agggtcgatg ccctgaatgt aatcacatca gttacaattc attcatcgat aatctcaatc | 3180 |
| cactcaaatt atttggagga ttccaatcac ttggtaatta ttaactagct tcttagtcta | 3240 |
| atctcatatt ccacaggtga tggtttcaca aaagctgcag acttcctcat atacataatt | 3300 |
| ggtcttatta ttcttatct tctaataacc aaattcatca ttccggtctg ccaggtcata | 3360 |
| tttactgata tatctcaagt tattgtacaa caggaaaaga tcgttagaga attagtgaag | 3420 |
| agtattcatt gaaaaatgtg ttctttcagt gttgtgtatg tcctcttctc gttgccaaaa | 3480 |
| taactcaatc tcaacgaaat cgatcacaaa cggaagttga aattgaagaa cgaaggcgaa | 3540 |
| aaatgaagag gaataatgat gttctacctg gagattatgt atga | 3584 |

<210> SEQ ID NO 2
<211> LENGTH: 2052
<212> TYPE: DNA
<213> ORGANISM: Artificial Sequence
<220> FEATURE:
<223> OTHER INFORMATION: Synthetic polynucleotide

<400> SEQUENCE: 2

| | |
|---|---:|
| atggaaccgc cgtttgagtg gtctcccccag tttattctgc ttctcctagc agttacaacc | 60 |
| tacggatttc cactcgagga gaaattcgat gggctcttcc gtgcagagcc accacactgt | 120 |
| tccaagacac caattgtccg tgctcaaaca tctcaaaatg cgatgtcatc aattgcaaga | 180 |

```
ggaatgcaaa tgcaattctc aattggtttg cacactgcag tctgcttcag attatatgaa    240
gacactcaac tcgcatccca agagatcaat gatgatgaaa atgctggaaa tcagacatca    300
cttcttcata ctattcgatt ggaaaagctt gaacatcacc atccgataac tcagcggtac    360
acttttggaa tccctgaagt tcatgccagt tgtatctgtg agtgtgatgc acatcttca     420 acatgtaccg cagaatctca tcagtttacc gcttgtccag agtctgataa gtctgatgaa    480
acatcttcat gctaccgcac gttcttccca aatcagacac caatcgggtg cagtgaagac    540
gacatcccca agctttgctg tgacgttcga ttcaagccat ataaaaatat gacattcctc    600
gcagtcaaac tagaacaacc tacaacgtat gcaacatttg tctacgcagc ttatgatttt    660
gtaaatggat attgggtgga aaagataaa  actaaaatcc gttctcaatt agatggtgga    720
acacaggata ggcatctcga ccaaaaacgt cgaatttcat tggctgtaac tgccggagga    780
cgagcatctc atcaactgga gacaggaatg tatttctcaa gaacaagtaa tggaggagaa    840
acagaagaac tgagaatgca accattgaat gagattacag caataacttt tgaccgtctt    900
ggatggtaca gaatggacga ttctggtcat tttcatgtga ataatggagt tgtgaaaatg    960
gatgatattc acaaggctaa agtgaaaaat tgcaaagagc aaacttataa atcaattctc   1020
tctgcaaatc attatatgcc aggacatttc aatttgactc gtccacttga agttatcaaa   1080
ccgtggattc aatctgctcg aatttttgat agttctctca gacaagctgt tgtaacacat   1140
gccgaaggaa ctaatcttca aatttcaatt cacttggatg acgaggtgga aagtcaaaac   1200
cttgtcttct tccataatgc atcaagaatt cgtgacttca gtggatccat catcgttgat   1260
tcaaaatcaa atcgattgtt caacttgaca gtatatgagg cttctggaaa aattgatgga   1320
tcagtgaaga tgtcaactgg atttggatct gatacaattc acacattcac tgcttatgtt   1380
agtgatcttc atgcttcaaa ccgttctatg attattccac tgccagccat cgttggacaa   1440
ggagccagag caatctgtct ccgagcagat tcaatggctg atattgacaa atttgtcat    1500 gtcattgagt atttcgagag cccttttggaa atcgatcttg ttgagggaaa atggcacgaa   1560
atgattggaa cctgcccaac ttgtaatcaa atcaatttca atggaatgat gaaatttctg   1620
aatccagctc attggatcaa aggaatcagt tcgattggtg acggcgttat gattgctacg   1680
gatattgttg tgtatctcgg agttttgtgt attctgtatc ttcttattac gaagattatt   1740
gttccgttgg ttcgttgctg ggtatgcccc atgtcgattt tctgcaatgg gtcctcttcg   1800
tcgtccaaaa acaaaaatga taagagaagg aaggagagag aggagaggcg cagaaaggac   1860
aaatttgtct cagaatccga agatggtgca agaagtagtt ccgagcccca cgacactttg   1920
gcgagatacc atggaaatca ctcggagcgg cactatagca gtagccagta cattggtcta   1980 gagggccccgc ggttcgaagg taagcctatc cctaaccctc tcctcggtct cgattctacg   2040
cgtaccggtt ga                                                        2052
```

<210> SEQ ID NO 3  
<211> LENGTH: 1806  
<212> TYPE: DNA  
<213> ORGANISM: Artificial Sequence  
<220> FEATURE:  
<223> OTHER INFORMATION: Synthetic polynucleotide

<400> SEQUENCE: 3

```
atgttctcac cacttttttg tcttcttctt ctgctcagct actgttcatc atcatcatca     60
tcatcagttc ttgcctctaa attacaaatc ccacaatgca gcagaacaag cttggttaca   120
```

```
ggtgtgatgc gttcggtcaa tctggacacc acagaaatga ccatgactac gacaatgcag      180
acacagattg gcttgcacga gacgggctgc ttttttgtca atctgcatcc ggataatcga      240
ctttcgctga acgacacggt ggaagagtcg attttgacaa gcaacaccag cttgttgcac      300
acgttgcgct acgaaagcac ccaccagttg tatcctgtcc gtcagcagta tattttgca       360
ataccggaaa ttgattccga ctgcatttgc gattgtccag gtggtgacga ccactgcgcc      420
gtggattatg cttacaaaaa ttgcaccggc gacaatcatt cggcattctg cgtgcacacg      480
tatcatccgc accagtcggc tgctggatgt caactggccg gcgaagcgga tatttgctgt      540
aaacttgtcg tcaaaccgta ccaaaatcga cgttacgttg ccgtccaaat cggccaaccg      600
ctgaccgtgg ctacttttca ctaccaactt tacagcaaac agcactacga ccagtggcaa      660
atgttacacg atcaacgttt tcaagcagtc agtggccaat cccaacgtgt gcaattggat      720
caggctggtt tgcagcttca gttgggcgat ttgaagccga tctggcagct caaagaaggc      780
atgtacgttt tcgatttgaa cgacgaaaat ttcaccctac gccacggggt tccgatcaac      840
cgtttccacg agtacagcgg tcacaagttg ggctggctgc gttggcagag tgcggacaag      900
cgttggaccg tacgaaatgg tcgcatcaag ctgcaagctg cccatttcgt ccagacggtc      960
aactgcctcg cccaagaata tgccgaaacg tacaacgccg attttacgt tccaagcaaa      1020
gagaacggcc agaagccgtt tttccttgga catccggtgg agcaaacgga acgctggatc      1080
cgcacggtga aactggtcga ccggagcagt acgtccagac aaattcaagt cgaacaaaac      1140
caatcgccac caataagcat cctgctcagc ttcaacagca ccgtaggcat gaccgtactg      1200
tatcacggct ccgagcttgg cgaatttgtc gccaccatac atttggatgc tcattccaat      1260
cgcttcatca acatcaccgc catgaattgc aaaggtacac tgattggtca gttgtaccgg      1320
tcgaacagac aagaaacaac ggaactggtg ttcagcagct acgtgggcgg tgaggatcgg      1380
ttgcaaaata gtactattcg aatcggcgcg ccggccacgg tcaacggatc ccggtggctt      1440
tgtttgcaac cgtacgaaaa gcccaagctg cagaaatgtc gatgggcaac gttcagcgcg      1500
cagccgttgc ccaaagtcga actaccccac agatggactc aagctcaggg tcactgtacg      1560
gattgtaatc aaatttcggt aaataatttt ctcaaatatc tcaatccggc caactggaca      1620
cagggtgtca acggctggtc cgaagcgatg gccgtcggtt tggaagtggc gttctatttg      1680
ttgttggcgg ttattttgtg cgcggttttgt cgacgtttga tctgcccgt tttacgttgg      1740
acaatttgtg gaaatggcag aacgaatgct aacaaattgg actacaagga cgacgatgac      1800
aaatga                                                                1806

<210> SEQ ID NO 4
<211> LENGTH: 1767
<212> TYPE: DNA
<213> ORGANISM: Artificial Sequence
<220> FEATURE:
<223> OTHER INFORMATION: Synthetic polynucleotide

<400> SEQUENCE: 4
atggtggtgc tgagggccgt gctgctgtgg gcctccatct ccggaatcca cggaaacagg      60
tgcaccaaga ccctgccaac caccggccac gtgaggtact cctccaggga gtccgctcag      120
gccctggtgg agaccttcat ccagtcctcc atcaagcccg cgagaccct gtgcttcacc       180
ctgcacgacg tgaccaacga cgcgccacc tccgacgcct ccatctccat ggccaccaac      240
ggctccgtgc cctgctgtg gcagctgacc tacgagggca tcgagatgga gtacggcgtg      300
aagaacaggt actccttcta caggcccaag tacgagtcca gtgcatctg cgactgcccc      360
```

```
cagtacggcg actactgcaa ctccaagacc aacaggtgta ccgagcacga gctggacttc        420
tgctacaaca cctacaggtc cgaccagacc gcccacggct gcctggccta ctggaactcc        480
gaggagtccg aggtgtgctg cgccctgtac gtgggcaagc accccgagtc ccccaagtac        540
gacgccgtgt acctgtcctc cgacggcaag cccatcgtga agctggccct gaaggtgtac        600
gactccagga ccgacgaggt ggtgtactcc taccccacct tcaccgtggc cctgaacgac        660
aggacccaca gggcccagca ctccgtgagg atggaggtga ccggcgacac ccccaccccag       720 atcgactccg gctactacta cgccacctcc gagggcaccc agctgtacac cgacgtgtcc        780
atcaacggcc tgaacgagtt cgaccccagg aagatgggat ggctgaaggt gagggacgac        840
ggcaccgtgg agaggccccc cgagaggacc gtgctggacg ctttccacct gaagacccac        900
aagtgccaca acaagttcga ctacaccgag acctggcaaa tctacggcga gggcgactgg        960
aagcactact ccggctccag ggtggagaac ttctacggct gggtgaggag ggtgtcctac       1020
taccccagda ggaggtccgt gaccgtggtg cccagatacg acaggctggt gaccgtgaag       1080
atcggcatca acaccaccac caacgtgctg ttcttctacc acgactccga cctgatcgac       1140
ttcaccgccg aggtgagggt ggacaagcac tccaacaggt tcgccaacat caccctggtg       1200
gctgctgtgg gatccctggt gggatccatc accccatact acggagctga cggagcctcc       1260
tccgctaccg tccacaggtt cgagctgcac gtggactccc caccagctgc caacaccatc       1320
aagaggatct ccctgcccaa gaccatcaac ggcacctcca ggatgtgcct gtcccccctg       1380
tccaagccca caacgaggt gtgcaagacc gtgcccttca tccaggaggc cctgcaggac        1440
ttcttcgtgc caccaacctg gagcccgggc aacccaggat ccgctggacc aggattcaac       1500
ttcaactggc tgttcgactt cttcggcttc ctgaacccog ccgagtggtt cgacggaatt       1560
cagggctggc tggagctgtt cgccatgctg ctggacatcg ccctgttcat cgccggcatc       1620
ttcctgttca tcaaggtctg cacctgcttc aacgtgttca ccaccaaggc ccccaagtgg       1680
gacgagggcg tggagatgtc cgtgctgagg aggaggaagg ccgagcccgg cgacgtctgc       1740
gactacaagg acgacgacga caagtaa                                          1767

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
atgatcttct cttctcttct actgtatac                                           29

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
tcatacataa tctccaggta gaacatc                                             27

<210> SEQ ID NO 7
<211> LENGTH: 36
<212> TYPE: DNA
<213> ORGANISM: Artificial Sequence
<220> FEATURE:
```

<223> OTHER INFORMATION: Primer

<400> SEQUENCE: 7
ttaattggta ccactatgga accgccgttt gagtgg                              36

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
aattaagcta gctcaaccgg tacgcgtaga atcgagacc                           39

<210> SEQ ID NO 9
<211> LENGTH: 42
<212> TYPE: DNA
<213> ORGANISM: Artificial Sequence
<220> FEATURE:
<223> OTHER INFORMATION: Primer

<400> SEQUENCE: 9
ttaattggta ccactatggt actgtggcaa tggtcaatag cc                       42

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
atgttctcac cacttttttg tcttcttctt ctgc                                34

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
aactgcctcg cccaagaata tgcc                                           24

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
atattcttgg gcgaggcagt tgacc                                          25

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
tcacaatttg ttagcattcg ttctgcc                                        27

<210> SEQ ID NO 14
<211> LENGTH: 46
<212> TYPE: DNA
<213> ORGANISM: Artificial Sequence
<220> FEATURE:
<223> OTHER INFORMATION: Primer

<400> SEQUENCE: 14
ttaattggta ccatgttctc accactttt tgtcttcttc ttctgc            46

<210> SEQ ID NO 15
<211> LENGTH: 69
<212> TYPE: DNA
<213> ORGANISM: Artificial Sequence
<220> FEATURE:
<223> OTHER INFORMATION: Primer

<400> SEQUENCE: 15
aattaagcta gctcatttgt catcgtcgtc cttgtagtcc aatttgttag cattcgttct      60
gccatttcc                                                             69

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
aattaaggat ccatggtgag caagggcgag gagctg            36

<210> SEQ ID NO 17
<211> LENGTH: 43
<212> TYPE: DNA
<213> ORGANISM: Artificial Sequence
<220> FEATURE:
<223> OTHER INFORMATION: Primer

<400> SEQUENCE: 17
aattaagaat tcttatacct ttctcttctt ttttggatct acc            43

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
tatgtcttag atctccaaag tctcatcagt acacagtact            40

<210> SEQ ID NO 19
<211> LENGTH: 38
<212> TYPE: DNA
<213> ORGANISM: Artificial Sequence
<220> FEATURE:
<223> OTHER INFORMATION: Primer

<400> SEQUENCE: 19
tgtatcatgg taccctctgt gaaatcccca ccatgagc            38

<210> SEQ ID NO 20
<211> LENGTH: 3584
<212> TYPE: DNA
<213> ORGANISM: Pristionchus pacificus

```
<400> SEQUENCE: 20
atgatcttct cttctcttct actgtataca atcatccttc ctcatctaat ctattcattc     60
cctcgttcat tcactcctca attcaaagta attcctcctc attgtatcaa gactccttcc    120
atcattgctc atccttccaa aggtattctc tatctttact ctcagatgtt agacagaatg    180
agatagaagg ggaataagag agacgcgtag gaagatgaag aggttcttca cactcttgtg    240
caatatcttc ggatatctca gctgatgaaa ctaactagag gatatttcac aagtgataag    300
atcaagtcta aaagaggaaa gatgtcatca atagttctcg tttctcacat tactcatctc    360
tctcattcct cattcctctc atcaactatc ctatcaatta cagtagttca acatgggca     420 gagtaatggg aatgggtgtca ttcataactg attcaggaga aggatcactc aaatctctcg    480
agatgcattt ctctattgga ttgcatacaa ctgtctgttt ccgattagag gatacaaatg    540
ataattcgac tcaatccaat caatcattac ttcatacagt tactctatct agtatagaac    600
atcatcatcc agtgagtatt ctacccaatc tccccttctc tgtcttcctc tttattttc     660 atcttctcag gtcacacaga aatacaactt cggtattcct gaagtaagtg cagattgttt    720
ctgtgaatgt gaatcaacag agagatgttc ttcttcctct tatgaattca ttaaatgtcc    780
agaggggaaa gatcaggtaa ttcatttctt tctctctttc atcataatca atcaatctcg    840
actcatggtt gctatcgaac attcttcccc aatcaatcca ataaatcatg cgaaagttca    900
tctccaatgg gatcgaatct ctgttgtgaa ctcaagttca atcccttga  ggtaggtcga    960 agagtatctt ccctctttct tctttcttta ctcattcact tctccgttcg aataaaaggg   1020
aggatgaatg gtcactccca ataggcgttt actcatcgtt cttcagtaat gaactcaata   1080
tactttcaga ataagacgta cactgcaatt agactgggag atccttccac attcgctatt   1140
ttcacttatg tttcctatga ttattctgga aattcatgga ttgagaggga taagaatacg   1200
attcgaattc aaatagatgg aagatctcag gaaaagtgag tcaatttcat gggaaatgga   1260
agagcttatc gggacttgga tcagtgcggt agattgtgag aaatgataag aataggaaga   1320
ttcccgcatt gagaaagagc taatttcaat ggaatgaaat ggttactgtc gatcgtattc   1380
tattcttgat tcttgcagta atcttgatag tagtggactt ctcaaattgg ttgtatctgc   1440
atggggaaga gtatcacatc aattggaaag tggaatgtat ttcactcaat caaatccagg   1500
aggagaaatg gaaggaataa gaaaggaaca aattaatgac atcaccgata ccaagtatgc   1560
ttttattgtc gttcattagc gctgattgat gtcaaatatg gctgctatta tttgtgaact   1620
tcgatgaatt ttgactaaaa atttttaatt tttgattgtt ttgaatagaa ttttaattaa   1680
ttaattaaat taagtgttta tcaattggga tggtatcgac aagacgagaa aagtggacat   1740
ttctacgtac aaaatggagc agttattgca aagaatctgc atggggcaaa agttatcgac   1800
tgcaaggaac agagatattc atcctctctt gctgctaatt tctatgtaag aataccatct   1860
tattcaattt atttatccct tgtcttgctt tgaaaataag tactaatgag atgaattaag   1920
atgccaggtc gatttactct tcctccttac gtcgaggaac gtcatcattg gattgaaaga   1980
gcggcattct atgatggatc aatgagacaa gtcatcgtat ctcattctga aggaactaat   2040
ctatatatcg gactccatgt aagcaattcc taattcctaa atctcgaacg tcaatgattt   2100 cccttttcttt ctctctaatt tgatgaggag tgaatagctg ctgtccatta tcttcactcc   2160
tttctctcat tatctcacta gaatcatgga gagaaagata gggaaagttc ctcaccgttc   2220
tctccttctt ttcttttgtc acagggaagg atttcgaaaa tagatgactc acttatccca   2280
taagatttac aaccatcctg atagtaaatc ttttctgata tgtaatctta tggaaccagc   2340
```

| | | | | |
|---|---|---|---|---|
| ttttgttgaa | taatcaagta | cttgaaggtg | tcgaaaggat | cagaaggaaa | tgttgtcttc | 2400 |
| cttcacaatt | catctcgaat | tgattcattc | gatggatcaa | ttcttgttga | ttctcattct | 2460 |
| cgtcattatc | tcaatctttc | actctccgaa | tcgactggca | aattgaatgg | actcattcat | 2520 |
| gctagtgaat | ccgttgcctc | tcctcaggta | aatacaaat | aagaataata | tttaaaatca | 2580 |
| ccgtatctcg | tccaaagtct | atctcttctc | cgttcccttta | gagggataaa | gttggccttg | 2640 |
| tgaaatgggg | acatcggctg | tcaataggtg | tcaatgagct | actcttttta | tcccccttaga | 2700 |
| cactcatcaa | gctctccctt | ctcttctaat | tgagtcgatc | acccttgagt | ataaatcact | 2760 |
| taatgggggtt | actctaagag | ggaagtaatg | aatgtgttca | gattcatatg | ttcacagtgt | 2820 |
| atgttcatga | ggttgtgtct | actaatcgat | ctcttctcgt | tccccttcct | gctactgttg | 2880 |
| ataaaggaag | gaaattagtt | tgtatgagag | cagaagaaga | aaggaagaag | attccatctg | 2940 |
| tgctgtactc | ccatatcatg | aagaagcact | tgaggttaca | caatttctaa | tttgcgttgg | 3000 |
| gatttaattc | aaaattaatt | aatgtatgaa | gaataagaag | ggacacacac | gaatgatgtt | 3060 |
| cacattatga | taaattgata | atttagattg | acgtggagaa | taattcgtgg | agggaattaa | 3120 |
| agggtcgatg | ccctgaatgt | aatcacatca | gttacaattc | attcatcgat | aatctcaatc | 3180 |
| cactcaaatt | atttggagga | ttccaatcac | ttggtaatta | ttaactagct | tcttagtcta | 3240 |
| atctcatatt | ccacaggtga | tggtttcaca | aaagctgcag | acttcctcat | atacataatt | 3300 |
| ggtcttatta | ttcttttatct | tctaataacc | aaattcatca | ttccggtctg | ccaggtcata | 3360 |
| tttactgata | tatctcaagt | tattgtacaa | caggaaaaga | tcgttagaga | attagtgaag | 3420 |
| agtattcatt | gaaaaatgtg | ttctttcagt | gttgtgtatg | tcctcttctc | gttgccaaaa | 3480 |
| taactcaatc | tcaacgaaat | cgatcacaaa | cggaagttga | aattgaagaa | cgaaggcgaa | 3540 |
| aaatgaagag | gaataatgat | gttctacctg | gagattatgt | atga | | 3584 |

<210> SEQ ID NO 21
<211> LENGTH: 3584
<212> TYPE: DNA
<213> ORGANISM: Artificial Sequence
<220> FEATURE:
<223> OTHER INFORMATION: Synthetic polynucleotide

<400> SEQUENCE: 21

| | | | | | |
|---|---|---|---|---|---|
| atgatcttct | cttctcttct | actgtataca | atcatccttc | ctcatctaat | ctattcattc | 60 |
| cctcgttcat | tcactcctca | attcaaagta | attcctcctc | attgtatcaa | gactccttcc | 120 |
| atcattgctc | atccttccaa | aggtattctc | tatctttact | ctcagatgtt | agacagaatg | 180 |
| agatagaagg | ggaataagag | agacgcgtag | gaagatgaag | aggttcttca | cactcttgtg | 240 |
| caatatcttc | ggatatctca | gctgatgaaa | ctaactagag | gatatttcac | aagtgataag | 300 |
| atcaagtcta | aaagaggaaa | gatgtcatca | atagttctcg | tttctcacat | tactcatctc | 360 |
| tctcattcct | cattcctctc | atcaactatc | ctatcaatta | cagtagttca | aacatgggca | 420 |
| gagtaatggg | aatggggtca | ttcataactg | attcaggaga | aggatcactc | aaatctctcg | 480 |
| agatgcattt | ctctattgga | ttgcatacaa | ctgtctgttt | ccgattagag | gatacaaatg | 540 |
| ataattcgac | tcaatccaat | caatcattac | ttcatacagt | tactctatct | agtatagaac | 600 |
| atcatcatcc | agtgagtatt | ctacccaatc | tccccttctc | tgtcttcctc | tttatttttc | 660 |
| atcttctcag | gtcacacaga | aatacaactt | cggtattcct | gaagtaagtg | cagattgttt | 720 |
| ctgtgaatgt | gaatcaacag | agagatgttc | ttcttcctct | tatgaattca | ttaaatgtcc | 780 |

```
agaggggaaa gatcaggtaa ttcatttctt tctctctttc atcataatca atcaatctcg    840
actcatggtt gctatcgaac attcttcccc aatcaatcca ataaatcatg cgaaagttca    900
tctccaatgg gatcgaatct ctgttgtgaa ctcaagttca atcccttga ggtaggtcga    960 agagtatctt ccctctttct tctttctttta ctcattcact tctccgttcg aataaaaggg   1020
aggatgaatg gtcactccca ataggcgttt actcatcgtt cttcagtaat gaactcaata   1080
tactttcaga ataagacgta cactgcaatt agactgggag atccttccac attcgctatt   1140
ttcacttatg tttcctatga ttattctgga aattcatgga ttgagaggga taagaatacg   1200
attcgaattc aaatagatgg aagatctcag gaaaagtgag tcaatttcat gggaaatgga   1260
agagcttatc gggacttgga tcagtgcggt agattgtgag aaatgataag aataggaaga   1320
ttcccgcatt gagaaagagc taatttcaat ggaatgaaat ggttactgtc gatcgtattc   1380
tattcttgat tcttgcagta atcttgatag tagtggactt ctcaaattgg ttgtatctgc   1440
atggggaaga gtatcacatc aattggaaag tggaatgtat ttcactcaat caaatccagg   1500
aggagaaatg gaaggaataa gaaaggaaca aattaatgac atcaccgata ccaagtatgc   1560
ttttattgtc gttcattagc gctgattgat gtcaaatatg gctgctatta tttgtgaact   1620
tcgatgaatt ttgactaaaa attttttaatt tttgattgtt ttgaatagaa ttttaattaa   1680
ttaattaaat taagtgttta tcaattggga tggtatcgac aagacgagaa aagtggacat   1740
ttctacgtac aaaatggagc agttattgca aagaatctgc atgggcaaa agttatcgac   1800 tgcaaggaac agagatattc atcctctctt gctgctaatt tctatgtaag aataccatct   1860
tattcaattt atttatccct tgtcttgctt tgaaaataag tactaatgag atgaattaag   1920
atgccaggtc gatttactct tcctccttac gtcgaggaac gtcatcattg gattgaaaga   1980
gcggcattct atgatggatc aatgagacaa gtcatcgtat ctcattctga aggaactaat   2040
ctatatatcg gactccatgt aagcaattcc taattcctaa atctcgaacg tcaatgattt   2100
ccctttcttt ctctctaatt tgatgaggag tgaaatagctg ctgtccatta tcttcactcc   2160
tttctctcat tatctcacta gaatcatgga gagaaagata gggaaagttc ctcaccgttc   2220
tctccttctt ttcttttgtc acagggaagg atttcgaaaa tagatgactc acttatccca   2280
taagatttac aaccatcctg atagtaaatc ttttctgata tgtaatctta tggaaccagc   2340
ttttgttgaa taatcaagta cttgaaggtg tcgaaaggat cagaaggaaa tgttgtcttc   2400
cttcacaatt catctcgaat tgattcattc gatggatcaa ttcttgttga ttctcattct   2460
cgtcattatc tcaatctttc actctccgaa tcgactggca aattgaatgg actcattcat   2520
gctagtgaat ccgttgcctc tcctcaggta aaatacaaat aagaataata tttaaaatca   2580
ccgtatctcg tccaaagtct atctcttctc cgttccttta gagggataaa gttggccttg   2640
tgaaatgggg acatcggctg tcaataggtg tcaatgagct actcttttta tccccttaga   2700
cactcatcaa gctctccctt ctcttctaat tgagtcgatc acccttgagt ataaatcact   2760
taatggggtt actctaagag ggaagtaatg aatgtgttca gattcatatg ttcacagtgt   2820
atgttcatga ggttgtgtct actaatcgat ctcttctcgt tccccttcct gctactgttg   2880
ataaaggaag gaaattagtt tgtatgagag cagaagaaga aaggaagaag attccatctg   2940
tgctgtactc ccatatcatg aagaagcact tgaggttaca caatttctaa tttgcgttgg   3000
gatttaattc aaaattaatt aatgtatgaa gaataagaag ggacacacac gaatgatgtt   3060
cacattatga taaattgata atttagattg acgtggagaa taattcgtgg agggaattaa   3120
agggtcgatg ccctgaatgt aatcacatca gttacaattc attcatcgat aatctcaatc   3180
```

```
cactcaaatt atttggagga ttccaatcac ttggtaatta ttaactagct tcttagtcta   3240
atctcatatt ccacaggtga tggtttcaca aaagctgcag acttcctcat atacataatt   3300
ggtcttatta ttctttatct tctaataacc aaattcatca ttccggtctg ccaggtcata   3360
tttactgata tatctcaagt tattgtacaa caggaaaaga tcgttagaga attagtgaag   3420
agtattcatt gaaaaatgtg ttctttcagt gttgtgtatg tcctcttctc gttgccaaaa   3480
taactcaatc tcaacgaaat cgatcacaaa cggaagttga aattgaagaa cgaaggcgaa   3540
aaatgaagag gaataatgat gttctacctg gagattatgt atga                   3584
```

<210> SEQ ID NO 22
<211> LENGTH: 4741
<212> TYPE: DNA
<213> ORGANISM: Artificial Sequence
<220> FEATURE:
<223> OTHER INFORMATION: Synthetic polynucleotide

<400> SEQUENCE: 22

```
gtcgacattg attattgact agttattaat agtaatcaat tacgggtca ttagttcata     60 gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atgggtcgag gtgagcccca cgttctgctt cactctcccc    420
atctcccccc cctccccacc cccaattttg tatttattta ttttttaatt attttgtgca    480
gcgatggggg cggggggggg ggggcgcgc gccaggcggg gcgggcggg gcgagggcg      540 gggcggggcg aggcggagag gtgcggcggc agccaatcag agcggcgcgc tccgaaagtt    600
tccttttatg gcgaggcggc ggcggcggcg gccctataaa aagcgaagcg cgcggcgggc    660
gggagtcgct gcgttgcctt cgccccgtgc cccgctccgc gccgcctcgc gccgcccgcc    720
ccggctctga ctgaccgcgt tactcccaca ggtgagcggg cggacggcc cttctcctcc     780 gggctgtaat tagcgcttgg tttaatgacg gctcgtttct tttctgtggc tgcgtgaaag    840
ccttaaaggg ctccgggagg gccctttgtg cggggggag cggctcgggg ggtgcgtgcg    900
tgtgtgtgtg cgtggggagc gccgcgtgcg gcccgcgctg cccggcggct gtgagcgctg    960
cgggcgcggc gcgggctttt gtgcgctccg cgtgtgcgcg aggggagcgc ggccggggc    1020 ggtgccccgc ggtgcggggg ggctgcgagg ggaacaaagg ctgcgtgcgg ggtgtgtgcg   1080
tgggggggtg agcagggggt gtgggcgcgg cggtcgggct gtaacccccc cctgcacccc   1140
cctccccgag ttgctgagca cggcccggct tcgggtgcgg ggctccgtgc ggggcgtggc   1200
gcggggctcg ccgtgccggg cggggggtgg cggcaggtgg gggtgccggg cggggcgggg   1260
ccgcctcggg ccggggaggg ctcggggag gggcgcggcg ccccggagc gccggcggct    1320 gtcgaggcgc ggcgagccgc agccattgcc ttttatggta atcgtgcgag aggggcgcagg   1380 gacttccttt gtcccaaatc tggcggagcc gaaatctggg aggcgccgcc gcaccccctc    1440
tagcgggcgc gggcgaagcg gtgcggcgcc ggcaggaagg aaatgggcgg ggagggcctt    1500
cgtgcgtcgc cgcgccgccg tcccttctc catctccagc ctcggggctg ccgcaggggg   1560
acggctgcct tcgggggga cggggcaggg cggggttcgg cttctggcgt gtgaccggcg     1620
```

```
gctctagagc ctctgctaac catgttcatg ccttcttctt tttcctacag ctccgggcaa    1680
cgtgctggtt gttgtgctgt ctcatcattt tggcaaagaa ttcgagctca tcgatgcatg    1740
gtacccgggc atgcctcgag ctagcagatc ttttccctc tgccaaaaat tatggggaca     1800
tcatgaagcc ccttgagcat ctgacttctg gctaataaag gaaatttatt ttcattgcaa    1860
tagtgtgttg aattttttg tgtctctcac tcggaaggac atatggaggg caaatcattt     1920
aaaacatcag aatgagtatt tggtttagag tttggcaaca tatgccatat gctggctgcc    1980
atgaacaaag gtggctataa agaggtcatc agtatatgaa acagccccct gctgtccatt    2040
ccttattcca tagaaaagcc ttgacttgag gttagatttt ttttatattt tgttttgtgt    2100
tattttttc tttaacatcc ctaaaatttt ccttacatgt tttactagcc agattttcc     2160
tcctctcctg actactccca gtcatagctg tccctcttct cttatgaaga tccctcgacc    2220
tgcagcccaa gcttggcgta atcatggtca tagctgtttc ctgtgtgaaa ttgttatccg    2280
ctcacaattc cacacaacat acgagccgga agcataaagt gtaaagcctg gggtgcctaa    2340
tgagtgagct aactcacatt aattgcgttg cgctcactgc ccgctttcca gtcgggaaac    2400
ctgtcgtgcc agcggatccg catctcaatt agtcagcaac catagtcccg cccctaactc    2460
cgcccatccc gcccctaact ccgcccagtt ccgcccattc tccgcccat ggctgactaa     2520
ttttttttat ttatgcagag gcgaggccgc ctcggcctct gagctattcc agaagtagtg    2580
aggaggcttt tttggaggct aggcttttgc aaaaagctaa cttgtttatt gcagcttata    2640
atggttacaa ataaagcaat agcatcacaa atttcacaaa taaagcattt ttttcactgc    2700
attctagttg tggtttgtcc aaactcatca atgtatctta tcatgtctgg atccgctgca    2760
ttaatgaatc ggccaacgcg ggggagaggc ggtttgcgta ttgggcgctc ttccgcttcc    2820
tcgctcactg actcgctgcg ctcggtcgtt cggctgcggc gagcggtatc agctcactca    2880
aaggcggtaa tacggttatc cacagaatca ggggataacg caggaaagaa catgtgagca    2940
aaaggccagc aaaaggccag gaaccgtaaa aaggccgcgt tgctggcgtt tttccatagg    3000
ctccgccccc ctgacgagca tcacaaaaat cgacgctcaa gtcagaggtg gcgaaacccg    3060
acaggactat aaagatacca ggcgtttccc cctggaagct ccctcgtgcg ctctcctgtt    3120
ccgaccctgc cgcttaccgg atacctgtcc gcctttctcc cttcgggaag cgtggcgctt    3180
tctcaatgct cacgctgtag gtatctcagt tcggtgtagg tcgttcgctc caagctgggc    3240
tgtgtgcacg aacccccgt tcagcccgac cgctgcgcct tatccggtaa ctatcgtctt     3300
gagtccaacc cggtaagaca cgacttatcg ccactggcag cagccactgg taacaggatt    3360
agcagagcga ggtatgtagg cggtgctaca gagttcttga agtggtggcc taactacggc    3420
tacactagaa ggacagtatt tggtatctgc gctctgctga agccagttac cttcggaaaa    3480
agagttggta gctcttgatc cggcaaacaa accaccgctg gtagcggtgg tttttttgtt    3540
tgcaagcagc agattacgcg cagaaaaaaa ggatctcaag aagatccttt gatcttttct    3600
acggggtctg acgctcagtg gaacgaaaac tcacgttaag ggattttggt catgagatta    3660
tcaaaaagga tcttcaccta gatcctttta aattaaaaat gaagttttaa atcaatctaa    3720
agtatatatg agtaaacttg gtctgacagt taccaatgct taatcagtga ggcacctatc    3780
tcagcgatct gtctatttcg ttcatccata gttgcctgac tccccgtcgt gtagataact    3840
acgatacggg agggcttacc atctggcccc agtgctgcaa tgataccgcg agacccacgc    3900
tcaccggctc cagatttatc agcaataaac cagccagccg aagggccga gcgcagaagt     3960
ggtcctgcaa cttttatccgc ctccatccag tctattaatt gttgccggga agctagagta    4020
```

```
agtagttcgc cagttaatag tttgcgcaac gttgttgcca ttgctacagg catcgtggtg   4080
tcacgctcgt cgtttggtat ggcttcattc agctccggtt cccaacgatc aaggcgagtt   4140
acatgatccc ccatgttgtg caaaaaagcg gttagctcct tcggtcctcc gatcgttgtc   4200
agaagtaagt tggccgcagt gttatcactc atggttatgg cagcactgca taattctctt   4260
actgtcatgc catccgtaag atgcttttct gtgactggtg agtactcaac caagtcattc   4320
tgagaatagt gtatgcggcg accgagttgc tcttgcccgg cgtcaatacg ggataatacc   4380
gcgccacata gcagaacttt aaaagtgctc atcattggaa aacgttcttc ggggcgaaaa   4440
ctctcaagga tcttaccgct gttgagatcc agttcgatgt aacccactcg tgcacccaac   4500
tgatcttcag catcttttac tttcaccagc gtttctgggt gagcaaaaac aggaaggcaa   4560
aatgccgcaa aaagggaat aagggcgaca cggaaatgtt gaatactcat actcttcctt   4620
tttcaatatt attgaagcat ttatcagggt tattgtctca tgagcggata catatttgaa   4680
tgtatttaga aaaataaaca aatagggtt ccgcgcacat ttccccgaaa agtgccacct   4740
g                                                                   4741
```

<210> SEQ ID NO 23
<211> LENGTH: 589
<212> TYPE: PRT
<213> ORGANISM: Caenorhabditis elegans

<400> SEQUENCE: 23

```
Met Arg Leu Trp Gln Trp Ser Ile Ala Val Ala Ile Cys Leu Val Met
1               5                   10                  15

Val Thr Glu Ala Arg Leu Arg Arg His His Arg Lys Arg Arg Phe Val
                20                  25                  30

Ser Ser Asn Phe Asp Glu Phe Tyr Cys Gly Glu Ser Ala His Ala Gln
            35                  40                  45

Ser Gln Phe Glu Glu Arg Glu Ser Asn Ser Ser Lys Val Ser Ser
        50                  55                  60

Val His Ser Thr Gln Phe Asn Trp Gly Leu Asp Asn Thr Ile Cys Ile
65                  70                  75                  80

Lys Leu Gln Asn Val Val His Val Leu Lys Tyr Glu Arg Leu Glu Gln
                85                  90                  95

Arg Tyr Pro Ile Glu Asn Ser Tyr Thr Phe Ser Val Pro Leu Ile Asp
            100                 105                 110

Thr Asn Cys Lys Cys His Cys Tyr Gly Phe Gly Thr Asn Asp Val Cys
        115                 120                 125

Asn Val Glu Lys Tyr Ala Asp Asp Arg Asn Cys Thr Thr Ser Ser Glu
    130                 135                 140

Phe Pro Thr Cys Tyr Thr Lys Tyr His Pro Ala Val Glu Pro Leu Asp
145                 150                 155                 160

Cys Pro Val Thr Ser Ile Pro Ala Lys Ala Cys Cys Asp Ile Lys Leu
                165                 170                 175

Lys Pro Arg Asp Gly Arg Met Phe Arg Ala Val Lys Leu Gln Gln Pro
            180                 185                 190

Ile Asn Asp Met Ile Ile Ser His Ser Ile Phe Ala Asn Asn Ser Gly
        195                 200                 205

Lys Met Met Lys Val Leu Gly Pro Asp Glu Phe Arg Ile Asn Leu Leu
    210                 215                 220

Lys Gly Lys Glu Gln Phe Glu Leu Thr Glu Tyr His Arg Ile Ser Val
225                 230                 235                 240
```

```
Gln Leu Val Ala Ser Ser Pro Gln Gln Leu Arg Glu Gly Met Tyr
            245                 250                 255

Tyr Phe Pro Glu Glu Asn His Asn Asp Leu Arg Glu Gly Lys Ile Asn
                260                 265                 270

Glu Ile Thr Glu Ser Asp Leu Asp Lys Leu Gly Trp Tyr Arg Arg Val
            275                 280                 285

Gly Asn Asp Trp Gln Val Ala Thr Ser Gly Leu Leu Arg Asn Ala
290                 295                 300

His Lys Val Val Ile Lys Asn Cys Lys Gly Gln Val His Met Asp Gln
305                 310                 315                 320

Phe Ser Gly Thr Lys Asn Phe Val Leu Arg Gly Thr Gln Tyr Asn Asp
                325                 330                 335

Thr Tyr Asn Glu Arg Arg Val Ser Asp Asn Asn Phe Val Arg Ser Val
            340                 345                 350

Lys Val Asp Glu Ser Ser Arg Glu Ile Thr Ile Val His Glu His Gly
            355                 360                 365

Thr Ala Ala Gln Val Ser Leu Lys Thr Asp Thr Arg Pro Asn Leu Thr
370                 375                 380

Lys Ser Gln Ser Leu Leu Ala Asn Phe Thr Gly Ser Ile Thr Leu Asp
385                 390                 395                 400

His Asp Gly Asn Arg Met Leu Asn Val Thr Phe Phe Gly Val Lys Gly
                405                 410                 415

Thr Val His Ile Lys Met Tyr Val Asn Asp Arg Lys Leu Ile Ala Thr
            420                 425                 430

Phe Ala Cys Thr Ala Gln Phe Gly Thr Ser Leu Lys Asp Asp Gly Ser
                435                 440                 445

Arg Ile Ser Leu Pro Ser Thr Ile Asn Gln Ala Gln Trp Val Cys Ile
450                 455                 460

Leu Pro Asp Glu Gln Pro Thr Lys Ser Glu Ile Cys Lys Trp Ile Pro
465                 470                 475                 480

Tyr Glu Glu Lys Ala Met Arg Thr Pro Arg Gln Glu Gln Ser Trp Ser
                485                 490                 495

Lys Gly His Ser Pro Cys Ser Gln Ala Glu Cys Asn Ser Leu Lys Ser
                500                 505                 510

Gly Val Ser Asp Leu Phe Pro Trp Ile Met Asn Phe Asp Tyr Phe Met
            515                 520                 525

Ala His Gly Gly Asp Phe Thr Glu Trp Leu Lys Ile Gly Ile His Ile
530                 535                 540

Val Ile Ala Val Gly Leu Leu Leu Leu Ile Leu Leu Phe Thr Lys
545                 550                 555                 560

Cys Leu Val Pro Leu Ala Cys Cys Ser Leu Ser Ile Pro Phe Lys Asn
                565                 570                 575

Arg Asn Lys Lys Lys Lys Lys Asn Ser Ser Asp Tyr
            580                 585

<210> SEQ ID NO 24
<211> LENGTH: 658
<212> TYPE: PRT
<213> ORGANISM: Caenorhabditis elegans

<400> SEQUENCE: 24

Met Glu Pro Pro Phe Glu Trp Ser Pro Gln Phe Ile Leu Leu Leu Leu
1               5                   10                  15

Ala Val Thr Thr Tyr Gly Phe Pro Leu Glu Glu Lys Phe Asp Gly Leu
```

-continued

```
                20                  25                  30
Phe Arg Ala Glu Pro Pro His Cys Ser Lys Thr Pro Ile Val Arg Ala
             35                  40                  45
Gln Thr Ser Gln Asn Ala Met Ser Ser Ile Ala Arg Gly Met Gln Met
 50                  55                  60
Gln Phe Ser Ile Gly Leu His Thr Ala Val Cys Phe Arg Leu Tyr Glu
 65                  70                  75                  80
Asp Thr Gln Leu Ala Ser Gln Glu Ile Asn Asp Glu Asn Ala Gly
                 85                  90                  95
Asn Gln Thr Ser Leu Leu His Thr Ile Arg Leu Glu Lys Leu Glu His
            100                 105                 110
His His Pro Ile Thr Gln Arg Tyr Thr Phe Gly Ile Pro Glu Val His
            115                 120                 125
Ala Ser Cys Ile Cys Glu Cys Asp Ala Thr Ser Thr Cys Thr Ala
            130                 135                 140
Glu Ser His Gln Phe Thr Ala Cys Pro Glu Ser Asp Lys Ser Asp Glu
145                 150                 155                 160
Thr Ser Ser Cys Tyr Arg Thr Phe Phe Pro Asn Gln Thr Pro Ile Gly
                165                 170                 175
Cys Ser Glu Asp Asp Ile Pro Lys Leu Cys Cys Asp Val Arg Phe Lys
            180                 185                 190
Pro Tyr Lys Asn Met Thr Phe Leu Ala Val Lys Leu Glu Gln Pro Thr
            195                 200                 205
Thr Tyr Ala Thr Phe Val Tyr Ala Ala Tyr Asp Phe Val Asn Gly Tyr
            210                 215                 220
Trp Val Glu Lys Asp Lys Thr Lys Ile Arg Ser Gln Leu Asp Gly Gly
225                 230                 235                 240
Thr Gln Asp Arg His Leu Asp Gln Lys Arg Arg Ile Ser Leu Ala Val
                245                 250                 255
Thr Ala Gly Gly Arg Ala Ser His Gln Leu Glu Thr Gly Met Tyr Phe
            260                 265                 270
Ser Arg Thr Ser Asn Gly Gly Glu Thr Glu Glu Leu Arg Met Gln Pro
            275                 280                 285
Leu Asn Glu Ile Thr Asp Asn Asn Phe Asp Arg Leu Gly Trp Tyr Arg
            290                 295                 300
Met Asp Asp Ser Gly His Phe Val Asn Asn Gly Val Val Lys Met
305                 310                 315                 320
Asp Asp Ile His Lys Ala Lys Val Lys Asn Cys Lys Glu Gln Thr Tyr
                325                 330                 335
Lys Ser Ile Leu Ser Ala Asn His Tyr Met Pro Gly His Phe Asn Leu
            340                 345                 350
Thr Arg Pro Leu Glu Val Ile Lys Pro Trp Ile Gln Ser Ala Arg Ile
            355                 360                 365
Phe Asp Ser Ser Leu Arg Gln Ala Val Val Thr His Ala Glu Gly Thr
            370                 375                 380
Asn Leu Gln Ile Ser Ile His Leu Asp Asp Glu Val Glu Ser Gln Asn
385                 390                 395                 400
Leu Val Phe Phe His Asn Ala Ser Arg Ile Arg Asp Phe Ser Gly Ser
                405                 410                 415
Ile Ile Val Asp Ser Lys Ser Asn Arg Leu Phe Asn Leu Thr Val Tyr
            420                 425                 430
Glu Ala Ser Gly Lys Ile Asp Gly Ser Val Lys Met Ser Thr Gly Phe
            435                 440                 445
```

-continued

```
Gly Ser Asp Thr Ile His Thr Phe Thr Ala Tyr Val Ser Asp Leu His
            450                 455                 460
Ala Ser Asn Arg Ser Met Ile Ile Pro Leu Pro Ala Ile Val Gly Gln
465                 470                 475                 480
Gly Ala Arg Ala Ile Cys Leu Arg Ala Asp Ser Met Ala Asp Ile Asp
                485                 490                 495
Lys Ile Cys His Val Ile Glu Tyr Phe Glu Ser Pro Leu Glu Ile Asp
            500                 505                 510
Leu Val Glu Gly Lys Trp His Glu Met Ile Gly Thr Cys Pro Thr Cys
        515                 520                 525
Asn Gln Ile Asn Phe Asn Gly Met Met Lys Phe Leu Asn Pro Ala His
530                 535                 540
Trp Ile Lys Gly Ile Ser Ser Ile Gly Asp Gly Val Met Ile Ala Thr
545                 550                 555                 560
Asp Ile Val Val Tyr Leu Gly Val Leu Cys Ile Leu Tyr Leu Leu Ile
                565                 570                 575
Thr Lys Ile Ile Val Pro Leu Val Arg Cys Trp Val Cys Pro Met Ser
            580                 585                 590
Ile Phe Cys Asn Gly Ser Ser Ser Ser Lys Asn Lys Asn Asp Lys
        595                 600                 605
Arg Arg Lys Glu Arg Glu Arg Arg Lys Asp Lys Phe Val Ser
610                 615                 620
Glu Ser Glu Asp Gly Ala Arg Ser Ser Ser Glu Pro His Asp Thr Leu
625                 630                 635                 640
Ala Arg Tyr His Gly Asn His Ser Glu Arg His Tyr Ser Ser Ser Gln
                645                 650                 655
Tyr Ile

<210> SEQ ID NO 25
<211> LENGTH: 567
<212> TYPE: PRT
<213> ORGANISM: Trichinella spiralis

<400> SEQUENCE: 25

Met Phe Ser Pro Leu Phe Cys Leu Leu Leu Leu Ser Tyr Cys Val
1               5                   10                  15
Met Arg Ser Val Asn Leu Asp Thr Thr Glu Met Thr Met Thr Thr Thr
                20                  25                  30
Met Gln Thr Gln Ile Gly Leu His Glu Thr Gly Cys Phe Phe Val Asn
            35                  40                  45
Leu His Pro Asp Asn Arg Leu Ser Leu Asn Asp Thr Val Glu Glu Ser
        50                  55                  60
Ile Leu Thr Ser Asn Thr Ser Leu Leu His Thr Leu Arg Tyr Glu Ser
65                  70                  75                  80
Thr His Gln Leu Tyr Pro Val Arg Gln Gln Tyr Ile Phe Ala Ile Pro
                85                  90                  95
Glu Ile Asp Ser Asp Cys Ile Cys Asp Cys Pro Gly Gly Asp Asp His
                100                 105                 110
Cys Ala Val Asp Tyr Ala Tyr Lys Asn Cys Thr Gly Asp Asn His Ser
            115                 120                 125
Ala Phe Cys Val His Thr Tyr His Pro His Gln Ser Ala Ala Gly Cys
        130                 135                 140
Gln Leu Ala Gly Glu Ala Asp Ile Cys Cys Lys Leu Val Val Lys Pro
145                 150                 155                 160
```

-continued

```
Tyr Gln Asn Arg Arg Tyr Val Ala Val Gln Ile Gly Gln Pro Leu Thr
                165                 170                 175

Val Ala Thr Phe His Tyr Gln Leu Tyr Ser Lys Gln His Tyr Asp Gln
            180                 185                 190

Trp Gln Met Leu His Asp Gln Arg Phe Gln Ala Val Ser Gly Gln Ser
        195                 200                 205

Gln Arg Val Gln Leu Asp Gln Ala Gly Leu Gln Leu Gln Leu Gly Asp
    210                 215                 220

Leu Lys Pro Ile Trp Gln Leu Lys Glu Gly Met Tyr Val Phe Asp Leu
225                 230                 235                 240

Asn Asp Glu Asn Phe Thr Leu Arg His Gly Val Pro Ile Asn Arg Phe
                245                 250                 255

His Glu Tyr Ser Gly His Lys Leu Gly Trp Leu Arg Trp Gln Ser Ala
            260                 265                 270

Asp Lys Arg Trp Thr Val Arg Asn Gly Arg Ile Lys Leu Gln Ala Ala
        275                 280                 285

His Phe Val Gln Thr Val Asn Cys Leu Ala Gln Glu Tyr Ala Glu Thr
    290                 295                 300

Tyr Asn Ala Asp Phe Tyr Val Pro Ser Lys Glu Asn Gly Gln Lys Pro
305                 310                 315                 320

Phe Phe Leu Gly His Pro Val Glu Gln Thr Glu Arg Trp Ile Arg Thr
                325                 330                 335

Val Lys Leu Val Asp Arg Ser Thr Ser Arg Gln Ile Gln Val Glu
            340                 345                 350

Gln Asn Gln Ser Pro Pro Ile Ser Ile Leu Leu Ser Phe Asn Ser Thr
        355                 360                 365

Val Gly Met Thr Val Leu Tyr His Gly Ser Glu Leu Gly Glu Phe Val
    370                 375                 380

Ala Thr Ile His Leu Asp Ala His Ser Asn Arg Phe Ile Asn Ile Thr
385                 390                 395                 400

Ala Met Asn Cys Lys Gly Thr Leu Ile Gly Gln Leu Tyr Arg Ser Asn
                405                 410                 415

Arg Gln Glu Thr Thr Glu Leu Val Phe Ser Ser Tyr Val Gly Gly Glu
            420                 425                 430

Asp Arg Leu Gln Asn Ser Thr Ile Arg Ile Gly Ala Pro Ala Thr Val
        435                 440                 445

Asn Gly Ser Arg Trp Leu Cys Leu Gln Pro Tyr Glu Lys Pro Lys Leu
    450                 455                 460

Gln Lys Cys Arg Trp Ala Thr Phe Ser Ala Gln Pro Leu Pro Lys Val
465                 470                 475                 480

Glu Leu Pro His Arg Trp Thr Gln Ala Gln Gly His Cys Thr Asp Cys
                485                 490                 495

Asn Gln Ile Ser Val Asn Asn Phe Leu Lys Tyr Leu Asn Pro Ala Asn
            500                 505                 510

Trp Thr Gln Gly Val Asn Gly Trp Ser Glu Ala Met Ala Val Gly Leu
        515                 520                 525

Glu Val Ala Phe Tyr Leu Leu Leu Ala Val Ile Leu Cys Ala Val Cys
    530                 535                 540

Arg Arg Leu Ile Cys Pro Val Leu Arg Trp Thr Ile Cys Gly Asn Gly
545                 550                 555                 560

Arg Thr Asn Ala Asn Lys Leu
                565
```

<210> SEQ ID NO 26
<211> LENGTH: 580
<212> TYPE: PRT
<213> ORGANISM: Branchiostoma floridae

<400> SEQUENCE: 26

```
Met Val Val Leu Arg Ala Val Leu Leu Trp Ala Ser Ile Ser Gly Ile
1               5                   10                  15

His Gly Asn Arg Cys Thr Lys Thr Leu Pro Thr Thr Gly His Val Arg
            20                  25                  30

Tyr Ser Ser Arg Glu Ser Ala Gln Ala Leu Val Glu Thr Phe Ile Gln
        35                  40                  45

Ser Ser Ile Lys Pro Gly Glu Thr Leu Cys Phe Thr Leu His Asp Val
    50                  55                  60

Thr Asn Asp Asp Ala Thr Ser Asp Ala Ser Ile Ser Met Ala Thr Asn
65                  70                  75                  80

Gly Ser Val Pro Leu Leu Trp Gln Leu Thr Tyr Glu Gly Ile Glu Met
                85                  90                  95

Glu Tyr Gly Val Lys Asn Arg Tyr Ser Phe Tyr Arg Pro Lys Tyr Glu
            100                 105                 110

Ser Lys Cys Ile Cys Asp Cys Pro Gln Tyr Gly Asp Tyr Cys Asn Ser
        115                 120                 125

Lys Thr Asn Arg Cys Thr Glu His Glu Leu Asp Phe Cys Tyr Asn Thr
    130                 135                 140

Tyr Arg Ser Asp Gln Thr Ala His Gly Cys Leu Ala Tyr Trp Asn Ser
145                 150                 155                 160

Glu Glu Ser Glu Val Cys Cys Ala Leu Tyr Val Gly Lys His Pro Glu
                165                 170                 175

Ser Pro Lys Tyr Asp Ala Val Tyr Leu Ser Ser Asp Gly Lys Pro Ile
            180                 185                 190

Val Lys Leu Ala Leu Lys Val Tyr Asp Ser Arg Thr Asp Glu Val Val
        195                 200                 205

Tyr Ser Tyr Pro Thr Phe Thr Val Ala Leu Asn Asp Arg Thr His Arg
    210                 215                 220

Ala Gln His Ser Val Arg Met Glu Val Thr Gly Asp Thr Pro Thr Gln
225                 230                 235                 240

Ile Asp Ser Gly Tyr Tyr Tyr Ala Thr Ser Glu Gly Thr Gln Leu Tyr
                245                 250                 255

Thr Asp Val Ser Ile Asn Gly Leu Asn Glu Phe Asp Pro Arg Lys Met
            260                 265                 270

Gly Trp Leu Lys Val Arg Asp Asp Gly Thr Val Glu Arg Pro Pro Glu
        275                 280                 285

Arg Thr Val Leu Asp Ala Phe His Leu Lys Thr His Lys Cys His Asn
    290                 295                 300

Lys Phe Asp Tyr Thr Glu Thr Trp Gln Ile Tyr Gly Glu Gly Asp Trp
305                 310                 315                 320

Lys His Tyr Ser Gly Ser Arg Val Glu Asn Phe Tyr Gly Trp Val Arg
                325                 330                 335

Arg Val Ser Tyr Tyr Pro Gln Arg Ser Val Thr Val Pro Arg
            340                 345                 350

Tyr Asp Arg Leu Val Thr Val Lys Ile Gly Ile Asn Thr Thr Thr Asn
        355                 360                 365

Val Leu Phe Phe Tyr His Asp Ser Asp Leu Ile Asp Phe Thr Ala Glu
    370                 375                 380
```

Val Arg Val Asp Lys His Ser Asn Arg Phe Ala Asn Ile Thr Leu Val
385                 390                 395                 400

Ala Ala Val Gly Ser Leu Val Gly Ser Ile Thr Pro Tyr Tyr Gly Ala
            405                 410                 415

Asp Gly Ala Ser Ser Ala Thr Val His Arg Phe Glu Leu His Val Asp
            420                 425                 430

Ser Pro Pro Ala Ala Asn Thr Ile Lys Arg Ile Ser Leu Pro Lys Thr
            435                 440                 445

Ile Asn Gly Thr Ser Arg Met Cys Leu Ser Pro Leu Ser Lys Pro Asn
450                 455                 460

Asn Glu Val Cys Lys Thr Val Pro Phe Ile Gln Glu Ala Leu Gln Asp
465                 470                 475                 480

Phe Phe Val Pro Pro Thr Trp Arg Pro Gly Asn Pro Gly Ser Ala Gly
            485                 490                 495

Pro Gly Phe Asn Phe Asn Trp Leu Phe Asp Phe Gly Phe Leu Asn
            500                 505                 510

Pro Ala Glu Trp Phe Asp Gly Ile Gln Gly Trp Leu Glu Leu Phe Ala
            515                 520                 525

Met Leu Leu Asp Ile Ala Leu Phe Ile Ala Gly Ile Phe Leu Phe Ile
530                 535                 540

Lys Val Cys Thr Cys Phe Asn Val Phe Thr Thr Lys Ala Pro Lys Trp
545                 550                 555                 560

Asp Glu Gly Val Glu Met Ser Val Leu Arg Arg Lys Ala Glu Pro
            565                 570                 575

Gly Asp Val Cys
        580

<210> SEQ ID NO 27
<211> LENGTH: 1713
<212> TYPE: DNA
<213> ORGANISM: Artificial Sequence
<220> FEATURE:
<223> OTHER INFORMATION: Synthetic polynucleotide

<400> SEQUENCE: 27
atggtactgt ggcaatggtc aatagccgtt gccatatgtc ttgtgatggt tacagaagct    60
cgtctcagaa gacatcacag gaaacgacga tttgtatcta gtaattttga tgaatttttat  120 tgtggagaaa gtgcacatgc tcagtcacag tttgaagagg agcgagaatc aaattcctca  180
aaagtctcat cagtcacag tactcaattc aattggggac ttgataatac aatttgtata  240
aaactccaga atgtggttca tgttttaaaa tacgaacgcc tcgaacaaag atatcctatt  300
gaaaactcct acacattttc ggttccatta ttgacacaa actgtaaatg tcattgttat  360
ggttttggga caaatgacgt ttgcaatgtg aaaagtacg ctgacgacag aaattgtacg  420
acgagctcag agtttcctac atgttacacc aaatatcacc cagcagttga gccactagat  480
tgtccagtta caagtattcc tgccaaggca tgctgcgaca tcaagttaaa ccacgcgat  540 ggcagaatgt tccgagctgt gaaacttcag caaccaatca atgacatgat aatttctcat  600 tctattttg caaacaacag tggaaaatg atgaaagttc tgggaccaga tgaatttagg  660
ataaatcttc tgaagggaa ggaacaatt gagttaactg aataccacag aatatccgtt  720
caattagttg catcttctcc tcaacaacaa cttcgcgaag ggatgtatta ttttccagag  780
gaaaaccaca acgatctgcg tgagggtaaa attaatgaaa taactgaaag tgatttggat  840
aaacttggat ggtatagaag agttggaaat gattggcaag ttgctacaag tggattacta  900

```
cttagaaatg cacataaagt ggtgataaaa aattgcaaag gacaagttca tatggatcaa      960
ttttccggaa ccaaaaactt tgttttacgt ggaactcagt ataacgatac ttacaatgaa     1020
cgaagagtat ctgacaataa ttttgtaaga agtgtgaaag ttgacgagtc ttctcgagaa     1080
attacaattg ttcatgaaca tggaaccgct gcacaagttt ctctgaaaac tgacactcgt     1140
ccaaatctaa caaaaagtca atcacttttg gcaaacttca ctggaagtat cacgttagat     1200
catgatggaa atcgaatgct taatgtcact ttctttggcg tcaaaggaac tgttcatatc     1260
aaaatgtatg tcaacgatcg aaagctcatc gcgacttttg catgtactgc tcaatttgga     1320
acgtctctga aagatgatgg tagtagaata agtcttccat cgactataaa tcaagctcaa     1380
tgggtgtgta ttcttcccga tgagcagcca acaaaatcag aaatatgcaa atggattcca     1440
tatgaggaaa aagcaatgag aactccgaga caagaacaaa gttggtcaaa aggacattca     1500
ccgtgctcac aagcagaatg taatagtctg aaaagtggag tgagcgactt gttcccatgg     1560
attatgaatt ttgattattt tatggctcat ggtggggatt tcacagagtg gctaaaaatt     1620
ggaatccatg ggcccttcga aggtaagcct atccctaacc ctctcctcgg tctcgattct     1680
acgcgtaccg gtcatcatca ccatcaccat tga                                 1713
```